United States Patent
Hucul et al.

(10) Patent No.: US 7,341,861 B2
(45) Date of Patent: *Mar. 11, 2008

(54) NON-RIBOSOMAL PEPTIDE SYNTHETASES AND ASSOCIATED BIOSYNTHETIC GENES

(75) Inventors: John A. Hucul, New City, NY (US); Nathan Magarvey, Minneapolis, MN (US); Michael Greenstein, Suffern, NY (US)

(73) Assignee: Wyeth, Madison, NJ (US)

(*) Notice: Subject to any disclaimer, the term of this patent is extended or adjusted under 35 U.S.C. 154(b) by 41 days.

This patent is subject to a terminal disclaimer.

(21) Appl. No.: 11/357,566

(22) Filed: Feb. 17, 2006

(65) Prior Publication Data

US 2006/0269994 A1 Nov. 30, 2006

Related U.S. Application Data

(62) Division of application No. 10/402,842, filed on Mar. 28, 2003, now abandoned.

(60) Provisional application No. 60/368,713, filed on Mar. 29, 2002.

(51) Int. Cl.
*C12N 1/20* (2006.01)
*C12N 15/00* (2006.01)
*C07H 21/04* (2006.01)

(52) U.S. Cl. .............. 435/252.3; 435/252.35; 435/252.33; 435/325; 435/410; 435/320.1; 536/23.2

(58) Field of Classification Search .............. None
See application file for complete search history.

(56) References Cited

FOREIGN PATENT DOCUMENTS

| EP | 1262562 | 12/2002 |
|---|---|---|
| WO | WO 00/40704 | 1/2000 |
| WO | WO 00/20601 | 4/2000 |
| WO | WO 02/24736 | 2/2002 |
| WO | WO 02/077179 | 10/2002 |
| WO | WO 02/101051 | 12/2002 |

OTHER PUBLICATIONS

Marahiel et al., Chem Rev. 1997; 97: 2651-73.
Stachelhaus et al., Chemistry and Biology 1999; 6:493-505.

*Primary Examiner*—Nashaat T. Nashed
(74) *Attorney, Agent, or Firm*—Darby & Darby

(57) ABSTRACT

The present invention describes the identification of novel non-ribosomal peptide synthetases and associated biosynthetic genes from *Streptomyces hygroscopicus*. The present invention further provides methods for generating novel compounds, such as antibiotics, from these synthetases and associated genes.

13 Claims, 8 Drawing Sheets mmpA Module 1 Adenylation domain:
Two-Dimensional Representation of Binding Pocket L-Serine Activation mmpA Module 2 Adenylation domain:
Two-Dimensional Representation of Binding Pocket Glycine Activation mmpA Module 3 Adenylation domain: Two-Dimensional Representation of Binding Pock Phenylalanine Activation mmpB Module 1 Adenylation domain:
Two-Dimensional Representation of Binding Pocket

Tyrosine Activation mmpB Module 2 Adenylation domain:
Two-Dimensional Representation of Binding Pocket Cyclo-arginine Activation

SEQUENCE LISTING

<160> NUMBER OF SEQ ID NOS: 53

<210> SEQ ID NO 1
<211> LENGTH: 47988
<212> TYPE: DNA
<213> ORGANISM: Streptomyces hygroscopicus

<400> SEQUENCE: 1

```
agatcgcgtg tacgccgtcg ccgggatcat gcgtgcgccg tcgccaaggt gccggatttg      60
cggtaagtag tgggcgatgt ccgccacgcc gcgcccgcga cccgttctac ggccgttccg     120
ccccggagac ggccgctcgc tgctggcggc ctggtgccgc agcgccccgg acgatccgat     180
caccgccgcc cgcttccgga cgctgatcct gctcgacccc aatttcgacc cagagggggtt    240 acgggtggcc gatctcgacg ggcaggtggt gggcgccgtc tacgccgtgc gccgccgtac     300
cccgctggcc ggcaccgacc tggagccgga cgtcggctgg atcctgttct tcttcgtcga     360
tccgccgcac cgccgtacgg gcctcggccg ccggctgctc accgatgccc tcgactggct     420
gcgcggacac ggccgcaccc gggtcgactt cgccccgtac gcccccccact acgtgctccc     480 cggcctggac cgggccgcgt accggaggc cgcccggctg ctggcgagcc tcggcttccg     540
tccccgctac gaggccgcgg cgatggaccg cggcctggtc ggctaccgca tgccggacga     600
ggtacggcgg cacgaggcgg ccctgacggc gcgcggccac cgattcggca ccccgtccga     660
cgacgatctg gtggacctgc tcgggctggc cgaggagttc acccccgact gggcgcgggc     720
gatccggcag tgcctgaccg gcggcgcccc tctggaccgc atcgtcagcg cccgcgcacc     780
cgacgggcgg atggcgggct gggccatgca cggcgcgtac gacggtacgg ccgagcggtt     840 cggcccccttc ggcgtacgga aggagctgcg cggcgccggt ctgggcaagg tgctgctgca     900
```

-continued

```
tctgacgctg gagcggatgc gggcgctcgg cgtgcacggg gcgtggttcc tgtggacggg      960
cgagcagagc ccggcggggc atctctaccg cgcgagcgga ttcaccacga cccggaggtt     1020
cacggtgctg cggtgggagg cgggatgagg cgccgtacat tcacggccgg ggccgcggcg     1080
ggggccgccc tgttggccgg ggccggatgc gacgcgcccg gtggcgccgg gcacggagac     1140
ggagagcacg gagacggaga cggcggtgac ggccggggca gcggcggccg tcgcggcgcc     1200
cccgtcaccc tgaccgtcct cacgcactac gcgagcgaac cgctcgcctc ggcgctgcaa     1260
accgtcgtcg acgcctggaa cgcgacgcac cggcgcatca cggtgcgcac ggccgcggtc     1320
aagttccccg atctgctgac gacttacatg gtgcggcagg ccgcgggcca gggcgccgac     1380
atcatccatc cgtactgcct gtggaccggc cagctggtgc gggccggagt actgcgcccg     1440
gtgccgccca cggccacgcg gcagatccgc cgggacttca ccccggcggc cgtggcggcg     1500
tcgtccgtgc acggcacgct ctacggctac cccacggagg tgcagaccta cgcgctctac     1560
tacaacaagc ggctgctgcg gcaggccggt atcgacggac cgccgggtac ctggcaggag     1620
ctggaggacg cggcgtaccg caccgcccgc cgcgaccgcc acggcaacat gctggtgcag     1680
ggcttcgggc tgtcacgggc cgacgatgcg agcgtcgtgg ggcagacgct ggccctgctg     1740
gccgcgcgcg gcggcacatt cctcacctcc gacggacggc ggaccgccat cggctcggcg     1800
gccgggcggg atgtgctcga cctggagcgc cggctcatcg accgcggcgc cgccgactcc     1860
ggtatctcgc tcctgagggc cttttccgtcc ggccaggtgg cgatggcgat caacgccggc     1920
tggtggacgg cgagtctgcg cggcgcgatg ggggcggact accgcgaggt cggggtggcg     1980
ccggtgccgg ggcccgcacc ggacgaccgc ggcacgctcg ccacgggctt cctgctcggc     2040
gtgaacgcga agagcagata tccgggggag gcctgggagt tcctgcactg gctcaacggt     2100
gtgcgggcgc cggccgcccg gccggggcgc agcgcgggag gaggcgtccc ggtgtccagg     2160
atgagcgcgc tccaggtgtc ggtcggttcg atgaccgggc gggcggacga tatgcgggcg     2220
ctgctgggag gcgacggcga gagggacgcc gacggccgtg gtggcggcga ccggaacctc     2280
ggccccttcc tggacgcgct gcgctacgcc gtcccggaaa cgaacggtcc gcgcgcgcag     2340
caggccaaat cgctgctgcg caagaacatc gaggacgtct ggacgggccg ggcctcggtc     2400
gatgccgcgc tgcgcaccgc cggccggcag atcgaccagg aactgtcccg gccctactga     2460
gccactcccc catgtcgtcg agaggtggtg ccgaatggct tcagccggcg gtggtcccgt     2520
cagggcggcc cggcggcggc agaccgccgt cgcctatctg ttcctgaccc cggccctgct     2580
gttcttcgcg gtcttcctcg ccctgccgct gctgttcgcc gtgctgctcg cgcagtcgcg     2640
ctgggccggc ttcgaccctg ccgatatcga gccggtcggg atggccaact tcaccgacct     2700
cttcgcccgc ggctcgacct tcctgacgcc cgtcctcacc aatacgctgc tgtacgccgt     2760
cggcaccgtc gcgatcgccc tcatcggcgc gctcaaccctc gcgacctgca tcgacaacct     2820
tcgtttccag gggctttggc ggaccctcta tttcctcccg atcgtgacga ccgtggtcgc     2880
cgtcggcaac gtatggaagt acatgtacgc accgggcggg ctgatcaacg gagtgctcaa     2940
cggtctgggt ctgcattccg tggcctttct ccaggacccc ggcacggcgc tgccgtccgt     3000
cgtcgtggtg caggcatggg cctccatggg aaccgcgatc ctgattctca ccgcgggcct     3060
gaagtcgatc cccgaggcct attacgaggc cgccgagctg gacggtgccg gcgccggcac     3120
cgttttccgg cgcatcaccc tgccgctgct ccggccgtcc ctgctcttcg tctgcatcac     3180
ccaattcatc accggattac agtcgttcgc cctgatcaat gtcatgacgg acgacgcgg      3240
accgggcgat gcgacgaatg tcgcggccct ggagatgtat cagcaggcgt tcaggtacgg     3300
```

-continued

```
cgactgggga atcgccagtg ccgccgcctt tgtgctgttc ctggtcattg tcgcgatcac    3360
ggtggggcag ctctggctgt tccgccggaa aggcggggaa tcgtgagccg gtccgctcgt    3420
cggcgcccgg gccgtcgccg cccctggggc tcgtacgccg tggtcgtcgc cggggccgcc    3480
ctcaccctcg tcccgttcct cgacatgctg ctgacctcgt tcaaggggcc cggcgaatac    3540
gggaaactcc cctaccgatt cctccccag gcgttcgacc tttccaacta ccgtgccgcg    3600
atggagcagc tggatctgcc cctgcttttc cgcaacagcg tcatcgccac cgccgtcatc    3660
accggatcca tcctggtgac ctccgcgctc gccggatacg cgctggccaa gctgcgcttc    3720
cccggccggg aggtgatctt ccgcctggtc ctgtccacga tgatgttccc gccgttcctc    3780
ttcttcatcc cgcactttct gatcctggtg cactggcccg cgccggcgg caacgacctg    3840 ctgggccgcg gcgggcggg cctcaccgtg agccttgcgg cgctggtcat gccgttcctc    3900
gtatccggtt tcgggatctt tctgatgcgg caattcatgg tctccatccc ggacgaactg    3960
ctggaggcgg cccgtatcga cggcgccggc gaattcgccc tctggtggcg catcgtgctg    4020
ccccagacga aaccggtggc ggtcaccctc gcgctgctca ccttcgtcaa cgcctggaac    4080
gaatacatct gggcgctgct gatctccacc gccaatccgc ggctgatgac gctgccggtg    4140
ggcatccaga tgctgcagag ctatctcgac cccgaccgta tggtcccggt catgatggcc    4200
ggcctggtgc tgagcatcct gccggtcctg ctgctcttcc tgctgctcca gaagcactac    4260
ctgcgcgggg tgatgctcag cggcctcaag tgacgtgcgt cctgggccga tgtggtcccg    4320
cggtgcaccc gccgaggttg acttctccgt aaaacatgat gagttccggt ttctcctggg    4380
ctgttgtggc aactgtggtg agagtttctg acccctcagg aggaaccatg gcttccgact    4440
cgtcgtcccc gacgccgatg ccggccgtgt cgttgatcgt gccgacgttc aacgaggcag    4500
cgaacattga tgagttgctc gacggcgtgt gtgcggcgat cccggcgggt ctggaggtcg    4560
aggtgctgtt cgtcgacgac tcgacggatg acacaccgga agtcatcgag aaggcggccg    4620
cgcgctgtcc gatgccggtg tcggtgctgc accgggaggt tcccgaaggg gggctcggcg    4680
gagcggtggt ggccgggatc gcccgtacga gtgcgccgtg gatcatggtg atggacgccg    4740
atctgcagca tccgccggag ctgctgccgc agttgatcga ggctggtgag cgcgcggcgg    4800
ccgagttggt ggtggccagc agatacgcgg agggcgggag ccgtggcggg ctggccggcg    4860
ggtaccgggt ggccgtgtcg ggggcgtcga ccgcgctgac caagtcgctg ttcccccggc    4920
tgctgcgcgg ggtctccgac ccgatgagcg ggtgcttcgc catccggcgg gaggcggtcg    4980
accgcgccgt acaggagggc gagacccggc aggaaggggg gctgcggccg ctcggctaca    5040
agattctgct ggagctcgcg gtgcgctgcc ggccgcgcgg ggtggtggag gtgccgtacg    5100
agttcgggga gcggttcgcc ggcgagtcga agtcgacggt gcgcgagggg ctgcggttcc    5160
tgcggcatct ggcggagctg cggaccagcg acaagcgggc ccggatggtg gccttcgggc    5220
tgatcggggt gtcgggcttc gtaccgaatc tgctggcgct gtgggcgctg accggtgcca    5280
cgaccctgca ttacgcggtg gcggaggtgc tggccaatca gctcggggtg ctgtggaact    5340
tcgccctgct ggacttcctg gtctaccgga gcgggaaacc ggggcgcggg gccggccggc    5400 tgctgggggtt cgcggcgctc agcaacgcgg atctgctggc gcggatcccg ttgatgatgc    5460
tgttcgtgga gcaggccggg atggggccgg tgccggcgac cgtgatcagt ctcgtggtgg    5520
tgttcgcgct gcggttcctg ctggtcgaca cgttgatcta ccggcgcaag ggcggctg    5580 ccaagcgcgc ggcggacgcg gcggtcaccg gcgggcaggg cgagcgcgct gcttagctga    5640
```

```
caaggcaaac tcgtggcggc ccgccccggc cggacagcag actccgagcg atgatctcgc      5700
cggattccac ctggacggac agaggcggag aaacgtgctg acagctcccg ttggtgtgga      5760
aacggatccg cgttcggcgg tacgccggc ccggcggccg gcggccgtcg tcgcgggcgc       5820
cgtgaccgtc gtgctgctcg ccctgtccga caggtacggc tacaacgtcg acgagctgta     5880
tttccggctg ctcggcgaac acggctgggc ctggggctac accgaccagc cgccgctggt     5940
gccggcgctg gtgcacgcca ccgcccaggt cctcggcgac tcggtgtggg cgatccgggt     6000
gccggcggcg ctgtgcgcag gggcgtggt gctgctcggg gcgctgatca ccgccgaact      6060
cggcggcacc cgccgggcac agactctttc cgccctgggt ctgggcagct cgttcctggt     6120
gctcagcgtc ggccacatca tggtgaccac caccctggac atgctcgcct gggccgcggt     6180
gctgctcttc gtcctgcggg cgctgctgcg ctcggagggc aagtggtggc tgtgggcggg    6240
ggtggtgctg ggcctggcgc tgtacgccaa gtacatcgtg gcgctgctgc cggtggcgct    6300
gctggccggc ctcgcgctgg tcggtccgcg gaaggtgttc cgtgaccggt ggctgtacgc    6360
ggggatcgcg ttggcgctgg ccatcggctc gccgaacctg atctaccagg ccacccatga   6420
cttcccgcag ctgcagatgg ccgatgcgct gggtgccacc gacggcccga tgaaccgggt   6480
catcttcgtg ccgagcctgg tgatcctgct cggtccggtg ctgaccgtgg tgtgggtcgc   6540
ggggctggtg aagctgctgc gtgaccggc atggcggccg gtgcgggcgc tggcaccggc    6600
gttcgtggtc ggggtggcgc tgaccctcta cggcggtggc cggcccgact acgtcggcgg   6660
gttcctgatc gggctgttcg cggccgggc ggtggccgcc gaccggtgga tggggcggcg    6720
tacgtcccgg cgggtgctgc tgtgcgccgg actggccgcc agtgcggtgc tccaggtgct   6780
gatgcgcctg ccggtgctgc cgcagagctc cccgttcgtg ccgctgaaca acatctccct   6840
ggagagcgtc ggctggccgc ggctcgccga gcaggtgcgc acggcgtacg aggcgctgcc    6900
gcggcagcag cgggagcggg ccgtggtgct cgccgacaac ctcggggaga tcggcgcgct   6960
ggaccgctac gggcacgggc tgcccgcggt gttcagcggc cacaacgaac tgcacaagtg   7020
gggcccgccg ccggagcgcg ccgatgtggt ggtcgcggtg ggcgtgcccc ggtcccggct   7080
ggccgcgggg ttcacctcgt gcaccgtcgt gggacgggtc gacaacggcg tcggcgtcga   7140
gaacgccgag cagggcagac cgatcacggt gtgccacggc cgcaaggctt cctgggcccg   7200
actgtggccc tcctaccact acttgagcgg ctgatgtgcc cctgcacccc gggccgtgtg   7260
cgaatcgaca actcagcggg aagtgaggcg tgatgacgac atccctcgac agggattcca    7320
gggcggccgc ggccgggccg ggggtgttcc gcccggcgcc gatggcgtgg cggccggtcg    7380
ccgtggtggt ggccgcgctg gccgtgctgt tgttcgcctt cgccggcgaa tacggctacc    7440
acgccgacga gttgtacttc cggctgctcg gggtgcacgg cttcgcctgg ggctatgtgg    7500
accagccgcc gctgctgcca ctggccgtac ggacctcgat ggagatcttc ggcgacagca    7560
tgtgggcgat ccgggtgccc gccgtgctgt gcgcggcggc cgtgaccgcg ctcggcgcga    7620
tgatcgccgc cgagctgggc ggttcccggc gggcccagac gctgaccgcg ttcggggtgg    7680
ccacctcgac gatggtgctc agcttcggcc actggatcct caccaccagc ttcgacaccg    7740
tggcgtgggc cgcggtgctg ctgttcgtga tgcgggtgct gctgcgcggc gagagcaagt    7800
ggtggctgtg ggccggggtg gtggtcggtg tcgcgctgta cgccaagtac atcgtgctgc    7860
tgctgccggt ggcgctgctg gtggggctgg cgctggtcgg tccgcggaag gtcttccgcg    7920
acgggaagct gtacgcgggc acggcgctgg cgctggtcat cggctcgccg aacctgatct    7980
accaggccac ccatgacttc ccgcagctgc agatggcgga ggggctggcg ggcaccgacg    8040
```

-continued

```
gcgaggcgaa ccgcgccatg ttcgccacga acctgatcct gctgttcggc cccgcgctgt   8100
tcgtgctgtg catgatcggg ctggtcaagc tgttccgggt gccggagtgg aagcccgtac   8160
ggacactggc cgtcggctat ctccggccca ccgcggcgtc gtacctcatc gagggcggcc   8220
ggccggacta caccggcgga ctgctgatcg cgctgctggc cgccgggtgt gtgacggccg   8280
accggtgggc gggcgcccgc aagctgcggc tctcggtgct cgcggtctcg ctgacgctca   8340
gcaccgcggt gcagatgctg ctgtcgctgc cggtgatccc caagagctcg ctgcgcgact   8400
tccagatcgc cagcatggcg ctggagacgt gggctggcc ccgtctggtc cagcagaccg    8460
aggcggccta ccgcgcactg ccggccgcgg accgcgaccg cgcgatcgtg ctcaccgaga   8520
acttcggcga ggcgggcgcc ctggaccact acgggcacgg gctgccgaag gtgtacagcg   8580
gccacaacga gctgtaccac tggggcccgc cgccgcagcg cgccgaggtg gtggtcgcgg   8640
tgggcatcga ccggaaccgg ctgtccgccg acttcaccag ctgcaaggtc gtcgaccaca   8700
tcgacaaccg cctgggcatc gacaatccgg aacagggcgt gccgatcacg gtgtgccacg   8760
gccccaagaa gccctggtcc gcgctgtggc cgacctaccg gcactacaac gcctatctgt   8820
agcgcgcctc tcgtccccca ccccgcggcc cggtccgaag caccttcgga ccgggccgtc   8880
cgccgacctg cttcgctgca cggtaaaagt cgtggatcag ccgcggagtt cacccgagac   8940
tggaaatcgc tggactgtgt acgcccatcc aatcgacttc cggacgaccc ctttcggggt   9000
ggaggcgtga tatgagtacc gaggtttccg aggcgcaggc gcgacgcgcc gtggcagaca   9060
tcttcaactc gacgctggct tcttcggcca tcggcgccgc gtgggagctc ggagctcttg   9120
acgagctgcg ggagaacggc aagttggatg tctccgattt cgccgtacgc catgatctgc   9180
acgagccggc ggtggtcggc atgttcaccg cgctggcgag tgtgggaatc gtgcggcgcg   9240
agggcgccac cgtcgtcgtc ggcccgtact tcgacgaggc caatcaccac cgttcactgt   9300
tccactggct caatcagggc agcggcgagc tcttccgccg catgccgcag gtgctgccga   9360
acgagaaccg cacaggaaag ttctaccagc gggacgcggg ggcgatcagc tacgcgtgcc   9420
gcgagatcag cgagcgctat ttcgacccgg cgttctgggc cgcggtcgac ggtctgggtt   9480
acaccccccac caccgtcgcc gacctggggt ccggcagcgg tgagcggctg atccagatcg   9540
cccgcggtt ccccggcgtc ccggcctcg gcgtggacat cgccgacggc gcgatcgcca    9600
tggcggagaa ggaggtggcc gccaagggat tcggcgacca gatctccttc gtgcggggcg   9660
acgcgcgcac catcgaccag gtctcggcgc gcggggaatt cgccgaggtc gatctgctca   9720
cctgcttcat gatggggcac gacttctggc cccgcgagaa ctgtgtgcag acgctgcgaa   9780
agctgcgcgc ggcattcccg aatgtgcgcc ggttcctgct cggcgacgcc acccgcaccg   9840
tcggtatccc cgaccgcgaa ctccccgtat tcaccctggg attcgagttc gggcacgaca   9900
tgatgggcgt ttacctgccg accctcgatg aatgggacgg ggtattcgaa gagggtggct   9960
ggcgctgtgt gaagaagcac gccatcgact cgctgtcggt ctccgtggtc ttcgaactcg  10020
agtaaccgca cacgcgcata tcgatcacgt cggcagaggg ggttttccat gggtgagtgg  10080
cgcgatcgcc gcctggacga attgttcgcc gagcaggccg cgagaacacc ggagcgtacc  10140
gcggtggtct tcgagggccg ggcggtgagt tatcgggaac tcgacgcccg cgccgagcgg  10200
ctggccgctg tgctggccgg ccgcggcgcg ggacccgagc ggttcatcgc gctgctgctg  10260
ccccgctccg ccgaactgat cgtgccatcc ctcgccgtac tgaagtccgg cgccggatac  10320
atcccgatcg acccggagta cccggccgac cgcatcgcct acatcctcgg cgacgcgcgc  10380
```

```
ccggtggcga cgatcaccac cgccgaggtg cgggacggtc tgccggaccc ggacaccggc    10440
tccgggaccg actggctgat cctggacgag tccgggtacg agcaggagcc ggccggggcg    10500
cgcccgcagc ccgccccggc cgcccgcgcg tccgcggaga accccgccta cgtcatctac    10560
acctccggct cgaccggccg gcccaagggc gtggtgatcc cgcacagcaa tgtgggacgg    10620
ctgctgtcgt ccaccgccca ctggtacggc ttcgacgagc aggacgtctg gccgctgttc    10680
cactccttcg ccttcgatgt ctcggtctgg agatctgggg cgcgctgct gcacggcggc     10740
aagctggtcg tcgtcccgca tgccgtcacc cgcgccccgg ccgacttcct gcggctgctg    10800
gtcgaggaac gggtcaccgt cctgaaccag acgccttcgg cgttctacca gctgatggcc    10860
gccgaccggg agaaccccgc gctcggcgcc caactcgccc tgcgttatgt ggtgttcgcg    10920
ggtgaggcgc tggacctggg caagctcgcc gactggtacg agcggcacga tgaccgggcg    10980
ccgacgctgg tcaacatgta cggcatcacc gagaccaccg tgcactcctc gttcctcgca    11040
ctggacaagg agggcgcggc cggcgccacg ggcagcgccg tcggcgtcgc cctccccgac    11100
ctgaccttcc atgtcctcga cgaggacctg cggcccgtcc cggtcggcgc ggagggcgag    11160
ctgtatgtgg ccgggcccgg gctggcacgg aactacgcgg gccggccggg gctgaccgcg    11220
gagcgcttcg tggcctgccc gttcggcccg ccgggggccc gtatgtaccg ctcgggcgac    11280
ctggtgcggc cgctgccgga cggcggcctc gaataccgtc ggcgcagcga cgaccaggtc    11340
aagatccgcg gtttccggat cgaactgggt gagatctcgc acgcactggc ccaggacccc    11400
tcggtcgacc aggccacggt ggtggtccgc gacgaggcgt cgggcgagcg caggctggtg    11460
gcgtacgtcg ttccggccgg ctccgcccgt cccacccctg cccggctgcg tgccgcgctg    11520
gccaccgcc tgcccggcta catggtcccc accgccttcc acgtcatgcc ggccttcccg     11580
ctgaccgcca acggcaagct ggaccgcagg gcgctgcccg cgcccacccg ccaggacagc    11640
gtcgacgccg actacgccgc ccccgagggc gccaccgagg aggcgctggc cgccatctgg    11700
cgcgaggtgc tcggcgtcga acagatcggt gccgacgacg acttcttcga gctcggcggt    11760
gactcgctgt ccgtggtgcg ggcgctgtcg cggatgcgga ccggcctggg gctgcgcctg    11820
acggccgcgg agttcttcgc cacccccacc gtccgggcac tggccgcgcg ccgcgagcgg    11880
ggcacgatcg gcgcgccgga gcagataccg gccgcgccgc gtaccggcgc gctgccgctg    11940
tccttcaccc agcagcggtt ctggctcttc cacgaactcg accccggcga ggtcgagtac    12000
aacgtccact ccgcgctgcg gctgcgcggc accctcgacc tccccgcgct gcgcaccgcg    12060
ctcggcgggc tgatcgcccg ccatgagccg ctgcggacga ccgtggtctc cgacgacggc    12120
cgccccaccg cggtcatcgc cccgcccgag ggcttcccgg tcccgctcac cgtcgaggat    12180
ctctccgcgc tgaccggcga cgaccaggag gccgcccagc ggcgactgct ggccgaggag    12240
gtcgcccggc ccttcgacct ggccgccggc ccggtgctgc gggtgctggt gatccgccgc    12300
ggcgagcgcg atcacgccct ggtgatcggg gtgcatcacc tcgccaccga cggctggtcg    12360
atggggctgc tcaccgacga gctgagcgcg cgctacgacg ccgcgcgccg cggggtgccc    12420
gccgcgctga gccgctgcc ggtccactac agcgactacg ccgcctggca gcgcgccacc     12480
gtggacgacg gccggctggt gccccagatc gactactggc gcgaccggct ggcggatgtg    12540
gcaccgctgc aactgcccac cgaccggccc cggcccgcgc tgaagacctc ggccggtgcg    12600
gcgcaccgct tcaccctcga ccgccggctg gtccgcgccc tcaaggagct gagcgccgcc    12660
catggcgcca cgctcttcat gaccctgacc gccgcgttgc aggtgctgct cgcccgctac    12720
tccggacagc aggacatcgc gctgggcacc gccgtctccg gccgggacca cccgcaggtg    12780
```

```
gagcggctgg tcggcgcgtt catcaacacc gtggtgctcc gctccgacgt gcgcggcgag   12840
ctgcccttcc acgaattcct cggggaggta cgggagacgg tgctgggcgc cttcgcgcac   12900
caggaccttc cgttcgaccg gctcgtggac gcgctgggcg ccgagcgcga cccgagccgt   12960
accccgctgg tccaggcgat gctgctgctg cagaacgccc cggccggtgc ggaggagttc   13020
gccgggctgc gcaccgagac cgtcgcgctg ccgcgcccgg ccgcgatctt cgacctgacg   13080
gtggactgca cggagcgggc cggggcgctg gaggtgatgg tcgagtacaa caccgatctg   13140
ttcgacgcga cgaccatcga gcggctctcg ggccatctgc gggtgctgct ggacgccgta   13200
tgcgcggcac cgcggcgcca ggtgcgcgat ctgccgctgc tgccggcggc cgaacgcgac   13260
acgctgctga ccggctggaa cgacaccgcc gccgcactgc cgacgacgct cggggtgcac   13320
cgccagttcg ccgagcgggc ccgcaccacc ccggacgcgc tcgccgtcac acactgcgga   13380 cagacccctca cctacgccca actcgacgcg cgcgccaacc agttggcgca ctacctgggc   13440
gctctcggcg tcggccgggg cacccccgtg gtgctgaacc tggcgcgcaa gccgcagctg   13500
atcgtgcgca tgctcgcggt gctcaaggcc ggcggcgcgt acgtaccgac cgcgctggac   13560
accccggcgg cacggctcgg gcatctcctg gaggagaccg gcaccccgt gctgctgacc   13620 accgcgcggc aggccggagc gctgcccccg accgaggcga gcgtcatcga cctcgacgcg   13680
gccgggccgg acatcgcccg gcatccggag cacgaccccc aggtggcgac ccggcccgag   13740
gacctcgcgt acatcgtcta cacctccggg tccaccggcc gccccaaggg cgtcgcggtg   13800
ccgcacagcg cgctgaccga ctactgcgcc tggcacaacg acgcgctgga cgtcggcccc   13860
gaggaccgcg ggtcgtccgt ggtcggcctg gccttcgacg tcgcggtcgg cgaggtgtgg   13920
ccgtatctgt gcgcgggcgc ccgcgtggac cagcccgacc aggagacgct ggacgatccg   13980
acggcgctgg tggagtggtt cgccgagaac ggcaccacgg tcgcctatct gccgaccccg   14040
cgcatcgaat ccctgctgga cgtagcgcg atcaccacca cccggctgcg caccgtcctg   14100
gtcatcggcg actcgctgcg ccgcaggccg cagcccggac tgccgttcac cctgctcaac   14160
gcctacgggc ccgcggaggc gacggtggcc gccacccagg cggtggtcga gcccctggga   14220
cccgacgcgc ccgccgggct gccgtccatc ggcgccccgc tgtacaacac cgccgcctat   14280
gtcctcgacg accggctgtg cccggtcccc gtcggggtgc ccggcgagct gtacctcgcc   14340
ggcgcgggtc tggcgcaggg ctatcagggc cgccccgacc tgaccgcgga gcgcttcgtc   14400 ggctgccccct tcgggccgcc cggaaccccgg atgtaccgca cgggtgacat cgtgcgatgg   14460
ctaccggacg gcaccctgga cttcctcggc cggatcgaca accaggtcaa actgcgcggc   14520
taccgcatcg aactcggcga gatcgagagc gtgctggccc gccgcgagga gctctcgcag   14580
gtgttcgtca cggtccgcga gccgtccccc ggccgccggt ccctggtcgc ctacctcgtc   14640
gccgaccggg gcaccgcgcc cgacccggag gagctcgccg gatacatcgc ctccgtactc   14700
ccggagtaca tggttccgtc ctccttcgta ctgctcgacg cgctgccgct gaccgcgaac   14760
ggcaagatcg accggcgggc gctgcccgag ccggagccgg ccggcggcga gggcgccgcg   14820
tatgtcgcgc ccggcaacga ggtcgaggag accctggccg ccatctgggc cgaggtgctc   14880
ggcgtcgaac gggtcggcgt gcaggacaac ttcttcgccc tcggcggcga ctcgatcagc   14940
ggtctgcaga ccgccgtacg ggcccgccgg gccgggctgc gactggcctc caaggacctc   15000
ttccagcgcc agaccatcgc ggcgctgagc ccgtggtga cggtggagcg gaccacggcg   15060
gacgccgacc ccgcaccgtc cgaccggccg accgcgccgt tcgcgctcag cggtctggac   15120
```

-continued

```
cgggtcggtg tggagcggct gaccgcggac ggcggcccgg ccgaggacgc ctacccgctg   15180
accccgatgc agagcgggct gctcttccac accctgatgc acgccgaacg cggcatgtac   15240
atcgagcagt tccacttcgc cctgcacagc atccgcgagc cggagctgct ggccaccgcc   15300
tggcagcggg tcgtcgaccg cacccctgtg ctccgtacgt cactggcctg ggacggcctc   15360
gccgaaccgc tccaggtcgt gcgcaccggc gtccggatac cggtggcaca gctcgactgg   15420
acggcactgg acgaggccgg acagcggcag gccctggagc ggtatctgac cgaggaccgc   15480
acgcgcgggc tcgatctgca caccgcgcca ctcgcccgga tcgccgtcgc ccgcctgggc   15540
ggcgaccagg tccggctggt gtggacgttc caccatctgc tgctggacgg ctggagcgtc   15600
gtacaggtgc tgtccgaggt gctcggcgag tacgccgcgc tcgccgacgg catcccgtac   15660
accccgcaac tgcggcacac ctacgccgag ttcgtcggcc agctggcggg gcaggaccac   15720
accgccgccg agaagtactg gcgtgccgcg ctcaccggcc gtgagtcgcc caccccgctg   15780
ccgtacgacc ggccgcgccc cgacgccat caggccgccc ccgacgccga gctgaagctg   15840
cggctgccgg ccgcggtgac cggccgactg ggcaccgcgg cgaagcgggc cggggtgacg   15900
atgaacaccg tggtgcaggg cttgtgggcg ctgctgctgg cccgccacag cggtgagcgg   15960
gacgtactgt tcggcgccac ggtcgccggc cggcccgacg atctggcggg cgcggaatcg   16020
gtgatcggcc tgttcatcaa caccccttccg gtgcgcgtcg acgtcgatcc ggacgccggt   16080
ctgctgagct ggctgcgccg ggtgcaggac gagcaggccg aggcgcgcgc ccatgagcag   16140
gtctcgctcg cccaggtgca gggctgggcg ccggagcggg cgcacggcgg actgttcgac   16200
agcgtgctgg ccttcgagaa cttcccggcc gacctcggtc ccgccgggaa ctacgggctg   16260
cggctcgacg ccatcgaggc cagcaacacc tccaactacc cgctcaacgc catcgttcag   16320
ctcaacgaag agctgaccgt gctgctgcgc tacgacaccg cgctgttcga cgcggacacc   16380
gtggcgcggc tggccggcca tctgcacacg ctgctggagg agaccgccga gaaccccgac   16440
cgccgggtcg gcgagctgcc cctgctcacc gccgccgagc ggcacaccat cgtgcacacc   16500
tggaccgaca ccgcctcgga ctactcggtc gaccgccggc tggacgcggt catcgccgaa   16560
caggccgcgg cccggccgac cgcgatcgcc gtcgtcgacg gtgaacggca gctgagttac   16620
ggcgagttgg accgccgcgc caaccagctg gcacaccatc tgcgcgccgc gggcgtgggc   16680
cgggacgccc tcgtcgggat cgccgtcgag cgcagcgcgg aggtcgtcgt ggccatcctc   16740
ggcacgctca aggcgggcgc cgcgtatgtg ccgctcgacc ccgaattccc cgcgcagcgg   16800
ctcgccacca tgctgtccga gtcccggccc gcggtcctgc tcacccagga acacctgctg   16860
gcggggctgc cgccgacgga cgcccgggtg gtgtgcgtgg accgggacct ggcggccatc   16920
gaggcgcacc ccaccgccgc gccggtctcc ggcggcgacg ccggcgacct ggcctatgtc   16980
acctacacct cgggctccac cggccgcccc aagggcgtca tggtcgagca ccgctcgctg   17040
ttcaacatca tcaccgaggc cggacggctc tacgacctgg ccccgacag ccggatgctg   17100 cagttctaca caatgagctt cgacggcggc gtctgggagg tcttcctgac gctgaccgcc   17160
ggcgccaccc tcgtcatcgc ggaccccgag gccgccaga gccggcccca cctcgccgag   17220
cagctgcgcg cggagtcgat caccgcgctg acgctgccgc ccgcggtggc ctcggtgctg   17280
gacgcggcct cgctgcccgg catacgcagc ctggggctcg ccggggatgt gctcgcgccc   17340
gaactcgccc gggagtgggc gcggggggcgc cggctgttca acatctacgg gcccagcgag   17400
gcgaccctgt ccgtcgccct gcaccgcgtc gaccccgggg ccgccgggcg ccaggtccgg   17460
ctcggaccgc cggtgcccaa cacccgtttc catgtgctcg acgagcggct ggccgtggtc   17520
```

-continued

```
ccggtcgggg tgaccggcga gctctacatc ggcggtgcgg gcctggcccg cggctacctg    17580
ggccgccccg acctgaccgc gcagcgcttc gtcgccgacc cgttcggacc gccgggatcc    17640
cgtctctacc gcaccggtga cctgatccgc tggaccccgc aggggcggct ggagttcgcc    17700
gggcgggtgg acaaccaggt caagatccgc ggctaccgtg tcgagcccgc cgaggtggag    17760
agcgcactgc tgcggcagcc cggcgtcgcg gaggcgtgg tgatcgcccg ggacgacgac    17820
accggccaca gcggctggt cgcctatgtc gtaccggacg ggagcggaac cgccccggaa    17880
cgcgccgccc tgctgcgcgc cctgggcggc caactccccg gctacatggt gccgtcggcc    17940
ctcgtcaccc tgcccgagct accgctcgga ccgaccggca aggtcgatgt gcgggcgctg    18000
ccggcaccgg atccggccgc cggcggcacc gccgaccgca tcccgccccg cacccccacg    18060
gaagaggcac tggccctcat ctgggtggag ctgctcgggc tcgaacacgt cggcgtcgag    18120
gacaacttct tcgacctcgg cggcgactcc atcaccagcc tgcggttgat gtcgcggatg    18180
ggcggcgcgt tcggtgtgga cgtctcaccc cgcgacttct tcgacgcccc caccatcgcc    18240
gcccttgccg agcgcctaga ggaaaagatc ctggcgcagt tggaagaagc cgtcggaggc    18300
ggcgccctat gaccagctct gcagcggacc agcccgacaa cccgaacacc accacccccgg    18360 cgtcgcgtgc cgagcgcacc gccgcgctgc cggcccatgt gcaggagctg ctgcgcgccc    18420
ggctggccgg ccgggccgcc gcgacgggcg gcgcggacac catcccgcgc atcgggcacg    18480
acggccccgt cgcgctctcg cccgcccagg aacgcctctg gtacctgcat gagctcgaac    18540
cggagagcaa cgagtacaac accctgcgcg tcctgcggct gcgcggcgac ctcgaccccg    18600
gcgcgctgtc cgcggcgctg agcgagatcg tcgcccggca cggcgcgctc cgcaccacct    18660
tcggctcccg cgaggggcac gccgagcaga ccgtgcatcc gcccgtaccg acaccgctgc    18720
cgctcgtcga cctgtcggcg gcggacgacg gcgagcggga cgacgcgctg cggaccctgc    18780
tgcagtacga ggcccggcgc cccttcgacc tgcgccgcgg cccggtgctg cgggcgcagc    18840
tgatccggct ggcggccgac gaccatgtcc tcgcgctggc cctgcatcac atcgtcaccg    18900
acggctggtc gatgggcgtg ctcaccggcg agctcaccgc ccactacgcc gcgacgctgc    18960
gcggtgcgcc cgccgtactg cccgaacttc cggtgagcta cctcgatgtc gccgtctggc    19020
agcgtgacca gctgagctcc gcgcggctgc gcgaggggct cgaccactgg cgccgggagc    19080
tggccgggct ggtcccgctc gatctgccga cgacctggca gcggccgccg gtccgcacca    19140
gcgccggagc gctgcactcc ttcgagatcc ccccggcggt cgccgcacgc cttcgggagc    19200
tgggccggga acagggcgcc acgctgttca tggcgctggt cgccgcggtc cagctgctgc    19260
tgtcgcgctg gtcggggcag cgggacatcg cggtgggcac cgccgcggcc gggcgcggcc    19320
ggaccgagac cgagaatctg atcggcttct tcgtcaacaa tctggtcctg cgctcccgga    19380
tcgatgagac gcggtcgttc accgagctgc tgcgggcggt acgcgcgacg gtcctggacg    19440
ccttcgccca cgaggatgtg ccgttccagc gggtcgtcga ggcgctgcat ccggagcgcg    19500
acctcagccg gccgccgctg gccgaggtcg cggtgaatct gcacaacacc ccgcggaccg    19560
acacggagct gcccgggctg cggatcgagg agatgccgcc gccggtgttc gcctccagca    19620
tggacctctc gttcgacttc accgagcgcg acgaccggct cgaagggcac ctcacctaca    19680
acaccgatct gttcgccgcg gacgccgccg cgcggatggc cgcgcagctg gtcaccctgc    19740
tcgaggacct caccgccgg ccccgcggtcc ggtggccgg gctggccgtg ctgcggccg    19800 ccgagcaccg tcgggtgacc gaggagtggc cgcactccgg gcccggccgg gagccgcgta    19860
```

```
ccgcaccgga gttgttcgcc gcgcaggtcg cgcggacccc tgatgcggat gcgctggtct   19920
ccgacgagga gacgctcagc tatgccgagc tggacggccg tatcaaccag tgggcgcggc   19980
tgctactggc ccggggtgcc gggccggaga cgctggtggc ggtggcgctg ccccgctccg   20040
cgcagatggt cacggcgatc ctggcgatcc agaagaccgg tgccgcctat ctgccgctgg   20100
acccgaagag ccccgcggaa cgcaaccggc tgatgatcga ggacgcccgc cgctgctgg    20160
tgctgacctc ggccgggttc ggcgacgcg cggaactcgg cgcgcccgca ctgttcctgg    20220
acgacccgga cacccgcgcc gccgcaggcg agctgtccgc cggcccgctg gcggccgccg   20280
agctgccccgc cccgctgctg cccggccacc cggcctacgt catctacacc tccggttcca  20340
ccggccgccc caagggcgtg gtggtcaccc acaccggtgt gcacggcctc gtggcggcgc   20400
agtcggcgca cttccgtacc gggcacgcg cgcgggtgct gtcgttcgcc tcgctcggct    20460
tcgacgcggc cttctccgag ctgggcatgg cgctgctgtc cggcggtgcg ctggtcgtcg   20520
tcgaccagga gcggatcctg cccggacagc cgctggccga cgtgctggcc gagcaccggg   20580
tcacccatgt gacgctgccg cccagcgcgc tgtccgcgct gaccccgggg acgctgccga   20640
aggacctcac cctggtcgtg gccggcgagg cctgccccgcc cgcggtgcc cgcacctggt    20700
ccgcccatca ccgcatgatc aacgcctacg gccccaccga gtccacggtc tgcgccagca   20760
tgagcgccgc gctgaccccg gacaccgtca gcggcgactc ggtccccatc ggccgcccgc   20820
tctccggcgt ccgggtcagc gtcctggacg accggctgcg cccggtgccg gccggcgtcc   20880
ccggcgaggt gtatctctcc ggcgccgcgc tggcccgcgg ctacctcggg cggctcgcgc   20940
tgaccgcgga gcggttcgtc gccgacccgt acggtccgcc gggaagccgg atgtaccgca   21000
ccggcgaccg cgcccgctgg ctggccggcg gcgacctgga ctacctgggc cgcaccgacg   21060
accaggtcaa actgcgcggc ttccggatcg agctcggcga ggtcgaggcc gtactgtcgc   21120
gccacgacgg ggtcggcgcg gtggccgcca cggtgcacaa ggacgagcgg ggcacccgcc   21180
gcctggtggc gtacgtcgtc ccggcgcggg aggacgcggc cgacccggcg cggctgcgcg   21240
agttcgcccg cgaggtgctg cccgagcaca tggtgccctc ggtcttcgtg ccgctggacc   21300
ggctgccgct gaacgccaac ggcaaggtcg accggcgggc gctgcccgca cccgacatcc   21360
ggcgcgacga gggcagcgcc cgtatcgcgc gcgcaccccc ggcggaggag acgctggcgc   21420
gcatctggtc ggaggtgctg ggcgtcacgg acatcggcgt cgaggacaac ttcttcgacc   21480
tcggcggcga ctccatcctc agccttcagg tggtggcgcg ggcccgggcc gccggactgc   21540
ggctgaccgc caagcagacc ttcctgcggc agaccatcgc cgatctcgcc gccgacgccg   21600
tcgccgagac cgaccccgcc gcgcacggtg cggccaacga cggcccggtc accggcgagc   21660
tgccgctcac ccccatccag cactggttct tcaactccct cggcgacagc ctggagcagt   21720
tcaaccagtc gctgtatctg gagctggccg agggccccga cctccccggcg ctgcgcgccg   21780
cactggccgc gctgaccgaa cagcacgacg cactgcggct ccgcgccgta tccgaggacg   21840
ggcagtggcg gctgcaccac gcgcccgccg agaccggtca actcctcgaa cacctcgatc   21900
tgtccggcgt ctcgcccgac gagcaggacg ccgcgatggc ggccgccgtc gacgcggcgc   21960
agcgggactt ccggctgtcc gaggggccgc tgctgcgggc ccggctgttc accctcggcg   22020
acgcccggcc gccccggctg tacctcgtcg cgcaccacct cgtcatcgac ggcatgtcct   22080
ggcgcatcct gctggcggac ctggagaccg gctaccgcct ggcggcggac ggccggccga   22140
tcgacctggg gccccggacc acctcgttcc gcgactggtc gcgccggctg tcgcgccatg   22200
tcgcggacgg cggcctggac gccgaactgc cgtactggaa gggcgtacag gacgcggcgc   22260
```

-continued

```
gcgagaccgc cccgctcccc gtcgacaccg gcgggctccc cgaccgccag ggcgcccagg    22320
aggagcccgg cgagaacacc gccgggtcgg cccgcaccgt ctccgtacag ctgtccgccg    22380
cgggcaccga ggcgctgctg cggcaggtgc ccgaggccta ccgcacccag atcaacgacg    22440
tcctgctcag cgcgctgggc cgggtgctga ccgactgggc gggcggcgag cgggtgctga    22500
tcgccctgga gggccacggc cgcgaggagc tcttcgacga ggtggacctc acccgcaccg    22560
tcggctggtt caccacccte ttcccggtcg ccctgcggat gccggccgac cgggactggg    22620
gaacggtcct caagagcgtc aaggaacagc tgcgggcggt gccccacaac ggactcggcc    22680
atggcgcgct gcgtcatctg gcagggccca actcccctct ggaggacggt ccggagcccg    22740
aggtcagctt caactacctc ggccagctgg acgtgtccgc cgaccgcacc ggcctcgccc    22800
gcgccatgct caccagcgag ggcgccgagc gggccgccgg ccagcaccgt gcgcagctgc    22860
tggagatcaa cggcgtggtc accggcgcc ggctggagtt ccactggacg tactcggtga    22920
accggcaccg cgcagagacc gtcgaacggc tcgccgcggg cttcatgacc gcgctggaag    22980
cgatcgtggc gcactgcgcc gccccggtt ccggcggcgc caccccgtcc gacttcccgc    23040
tggccgccct cgaccaggcc accgtcgaca agatcgccgg cgacggccgc acggtcgagg    23100
acatctaccc gctcaccgcg atgcagagcg gcatgctctt ccacgcgctg agcgagtccg    23160
gacgcgaccc gtacaccggg cacttcggcg tccgcgtgga cggcatcacc gacccggggg    23220
cactggccgc ggcctggcag caggtcgtcg accggacccc cgccctgcgc accgccatcg    23280
tctggcagga cgtcgcggaa ccccttcagg tggtgcacgc ggccgcccgt gtgccggtca    23340
cccatcacga cctgcggtcc ctgaccgagc aggaacggca ggccgccctg gaccggctgt    23400
gggagcggcg cgaggagacc gtcatcgatc tccgctcgc cccgcgctg cggctgaccc    23460 tcgtccggct caccgacagc gccgtccaga tgttctggac ctcgcaccac atcctgatgg    23520
acggctggag cttcgccggg ctgctgtcgg aggtgtgcgc ccagtacacc gcgctgaccg    23580
gcggcccccg cgtggcggcc ccggcccgcc gcccgtaccg cgactatgtc ggctggctgg    23640
ccgaacagga ccagccggcc gccgaggcgc actggcgctc ggtggtcgac gggttcacgg    23700
tgccgacgcc gctgccctac gaccggcagc cggtgaaggc acacggcacc cggtcctcgc    23760
gtgaggtgcg gctgcagctg tccgccgagc gctccgggcg gctgtccgag gccgccggt    23820 cggcgcggct gaccgtcaac acgctggtgc agggcgcctg ggcgatcctg ctggcgcgct    23880
acggcggggt gcgcgacgtc tgcttcggca ccaccgtctc cggccgtccc gccaccctgc    23940
ccggcgccga gtcgatggcc gggctgttca tcaacaccgt gccggtacgg gcgaccatcg    24000
acggtgccgg tgccggcgac ggcgccgcca ccggcaccgt cgagtggctg cggcggctgc    24060
agagcgagca gctcgactcc cggcagcacg agcatgtctc gctggcgcag atccagcgct    24120
ggagcggcgt accggccggc accaacctct tcgacagcat cgtcgtcttc gagaactacc    24180
cctacgacag cgatgcggcc gccaagtacg ggctgaccct cggcacgttc cagggcgacg    24240
aggtcaccaa ctacgccctc accctgaccg cgtacgtggc cgacgagctg catctcaacc    24300
tcggctacga cccggatctg ttcgacgagg cgaccgtcga gcggatggcc gggcatctgg    24360
cgacgctgct cgacgccgtc gccgccgccc gcacaccccc ggtggacgac ctcccgctgc    24420
tcgatgcggc cgaacaccac cggcttctca ccgagtggaa cgacaccgcc gccggcttcc    24480
cgccgccgcg gccggtccat gagctcttcg ccgagcgggc cgcccgtacc ccggacgcgg    24540
tggcggtcag cgacgccacc cggcagctga ccttcgccga gctggagacc cgcgccaacc    24600
```

-continued

| | |
|---|---|
| aactggcgca ccacctggcc ggtctgggcg tggcgcccgg cacgctggtc ggggtgtgcg | 24660 |
| ccgaccgcgg ggtggacgcc gtggtggcgc tgctgggcgt gctgcgggcc ggcggtgcct | 24720 |
| tcgtaccgct ggaccccgcc tatccggcgg agcggctcca ggtcatgctg gaggacgccg | 24780 |
| cggtgccggt cgtggtgacc gaggagcggc tgctggaccg gaccgccggg cacgacgcga | 24840 |
| cgacggtgtg cctggaccgc gatctgccgc tgctggagga gctgccggcc cgcccgccgt | 24900 |
| acaccgccgt ggcaccggac gacctggcgt atgtcgtcta tacgtcgggc accaccgggc | 24960 |
| gccccaaggg cgtgatggtc gagcaccggc acgtccacca catggtgcac gcctgggacc | 25020 |
| ggcgctacgg gctcgccgcg ctgcaaccgc gcgcgctgtc cgtctccagc atctccgtcg | 25080 |
| acctgttctt cagcgacttc ctgctctccg ccctcttcgg cggcacgatg gtgatctgtc | 25140 |
| cgcaggacgc cgtcgccgac caggtggcgc tgaccgatct gctgctcaag agccgggccc | 25200 |
| agctgatggt gacggtgccg acgctggccc gcgcggtggt cgccgagctc gcctggcgcg | 25260 |
| gtgtgacacc ggaggcgctg cgggtgctga tggtgggctc cgagggctgg ccggccgatg | 25320 |
| ccgcggccga gatcctggcc ggtctcgcgc cgggcacggt gctggtcaac gcgtacggat | 25380 |
| cgaccgagac cacggtcgac tccacggtct tccagctcgg ccgcgacccg ctgggcgacg | 25440 |
| ccgccttcgt accggtcggc aggccgctcg ccaacacccg gatctatgtg ctggacgagc | 25500 |
| ggatgcgccc ggttcccacc ggcgtcgtcg gcgagtgcta catcggcggc gacggagtgt | 25560 |
| cgcgcggcta tctgggccgc ccggagctga ccgccgagcg tttcctcgac gacccgttcg | 25620 |
| cgccggagcc gggcgcccgg atgtaccgga ccggtgacct cgcgcgctgg cgggccgacg | 25680 |
| gcaacctcga atgcctcggc cgggtcgacg accaggtcaa gatccgcggc ttccgggtgg | 25740 |
| aactcggcga ggtggaggcc gcgttggccc gccacccggc gatcgactcg gcggccgccg | 25800 |
| cgatccgcaa ggacgacggt gggccggccc gtctggtggg ctatgtcgtg cccgccgccg | 25860 |
| gccacacccc cgacctggcc gagctacggg ccttcgccgc cgaacggctg ccgtcgcccg | 25920 |
| ccgtccccac cgcgtacatg gtgctggacg cgctgccgat gacgccgagc ggcaccgtcg | 25980 |
| cccggcgtgc gctgccggcc ccggccgggg cgcaggacgc cgcccggccc tacaccgcgc | 26040 |
| cgggcagcgc caccgagctg ctgctctgcg gtatctggca ggaggtcctg ggcgtcgaac | 26100 |
| gggtcggcgt gcacgacaac ttcttcgacc tgggcggcga ctcgatcctc agcatccggg | 26160 |
| tcatctcccg gatccgggcc acgctgggcg tcgccccgtc gccccgccag ctcttcgaca | 26220 |
| ccccgacggt ggccggtctc gccgccaccc tcggccggga cgaccctcg gcggccgccg | 26280 |
| acgtccccct ggagccggcc gaccgcggcg caccgctgcc gctgtcgtcc gcccagcaac | 26340 |
| gccagtggtt cctgcacaac ttcgacccgg acagcagcga gtaccacatc gtcaccgggc | 26400 |
| tccggctcga cggtgatctg gacgtcgcgg cgctgcgagg ggcctgaac gggctcgtcg | 26460 |
| cccggcacga ggcgctgcgt accacctacg cggccaccgg cgagggcgcc gagcagatcg | 26520 |
| tgcaccccgc gggcgaggtg gtctgcgagc gtacggatct gtccgaggtg cccgaggacc | 26580 |
| agcgcgagga caccctgcgc gggcacatcg accgcgccgc cgcccggccg ttcggcctca | 26640 |
| ccgagggccc ggtcctgcgc gccgaactgt tccggctcgg cgcccgtgac catctgctgc | 26700 |
| tgctcgtcat ccaccacatc gccaccgacg gtgtctcgat gcaggtgctc accgaggagc | 26760 |
| tcggcgtcca ctacgccgcg gcgctcgacg gcacaccgcc cgccctgccg gcgctgccgg | 26820 |
| tctcctacgc cgactacgcg gcctggcagc gccggatgct gtccggcccg gcgctggacg | 26880 |
| gccatctcgc ctactggcag gagcggctgg ccggtgtccg gccgctggag ctgcccaccg | 26940 |
| accggccccg gccggcggtc cgcagctccg cgggccggat gctgctgatc gagatcgagc | 27000 |

```
cgcgggtggc cgcgggcctc aaggaactgg cccgccgcca tgacgccacc ctgttcatgg   27060
cgctcaccgc ggcggtccag ctgctgctgg cccgctacac cggacagccg gacatcgtcg   27120
tgggcacccc ggccgccggc cggggccggc aagaactcga ggggctcgtc gggctgttcg   27180
tcaacacggt ggcgctgcgg tccaccgtcg acgagagcgg gaccttcgac gccttcctcg   27240
gtgcggtgcg cgacaccgtc ctcgaagcgt tgtgcacga ggacgtgccg ttcgaccggc    27300
tggtcgaggt gctgcgaccg cgccgcgacc ccagccgtaa cgcactggtg gaggtgttcg   27360
tcggactgga gacggaccgg tcggcgccgc cggcgctgcc cggactgacg gtgaccgagg   27420
tcccgttcgt cagcggcgag gtcagccatg acctcagctt cgacttcgtc gacgggcccg   27480
acggcctgaa ggcggccatc ggctacagca ccgcgctgtt cgacgacggc accgtcgagc   27540
ggatggccgg ccagttccag cgcgctgctcg ccgcggtcct ggaggaccat cgcgcgctcg   27600
ccgacatcgc acccgcggac gaggccgagt gcggcggct cgccgaactg cggcaggccg    27660
cgccctcgga gcccgacgcg tcggaaaccg acggcgcgcc ggccgcctac cgcgcgcccg   27720
ggaccgctgc cgagcgggcc ctggcggaga tctgggccgc cgtgctgggg gtgccgcggg   27780
tcgggaccga cgacaacttc ttccagctgg gcggcgactc cctgctcagc atccaggcgg   27840
tgcagcggat gcggcaggcc ggcctggcgg tgaccaccaa ggatctgttc gtccaccaga   27900
gcatcgcccc gctggcggcc ctcgccgagg aacgggcggc ggaccggccg gaggcccccc   27960
aggcgcagca cgacgatgcc gggacggcgg gcgagatacc gctcaccccg atccagcgcg   28020
actacttcgc ggccgggccg ctcgccccgc accacttcac ccagtcggtg ttcctcgaac   28080
tgcacgccga tctcgacgag ccggcgctgc ggcacgcact ggccgcgctg atcggccacc   28140
acgacgccct gcggacccgc ttcgtacgcg aagacgcga ctggcggcag tacgccaccc    28200
cgccggagcc ggtggacatc ctgcgccggc acgacctgtc cgggctgccg gaggctcaac   28260
gggccgccgc catggacgag ttggcggcct cggccgacgc cgggctcgat ctggcggccg   28320 gccgccggc cgcggcgctg ctgttcgtct cgggcccgg ggagcggccg gcgctgttcg     28380
tgaccgcgca ccatctcgtc gtcgacggcg tctcctggcg gatcctgctg gaggacctgg   28440
aagccggcta cgtccaggcc cgcgacggga agccggtgtc cctgggcgcc aaaagcacct   28500
cgttcgggca gtgggcgcac cggctcgccc ggcacatcgc cgacggcggc ctcgccgagc   28560
aggccgccta ctggcaggcg ctgcccgacg gcaccgaggt cccgcacgac ggctcggggc   28620
ccgcggtggt ggagtccgtg cagaccgtca cggtggagct gccggaggac accagcgagg   28680
tgctgctgcg ccggtccgcc ggggtcttcc ggacccgctt ccacgaggtg ctgttcgccg   28740
cgctcgccgg caccctggcc cggtggacgg gcgaacgcca ggtcgtgttc gacaccgagg   28800
gccacggccg ggaggacctc ttcgacgacg tcgatctctc ccggaccgtc ggctggttca   28860
ccaccgagta cccccgtcgcc cttgaggtgg ccggcgaccg gacgactgg ccggcgctca    28920 tcaggtcggt acgcggacag ctgcggtcgc tgcccggcaa cggcttcggt tacggcgcgc   28980
tgcggcatct gagcccggcc ggcacccccg gtgccgcact cgccgaacgg gcccggccc   29040 aggtggtgtt caactaccac ggccaggccg acgaggcgca gcgcgcggcg gagagcgacc   29100
tctaccacgc gttcggcgac ccgatcggcc gggagcagcg gcccgacgag ctgaccggcc   29160
acccggtgga ggtggtgggc gccgtgcact ccggggcggct ccgcttcacc tggtacttct   29220
cgcgcaatgt tcatcacagg gccaccatcg acaaggtggc cgaggacttc gccgacgcgc   29280
tgcgcgccat cgcccggcac atcacggagc ggtgagccat ggaccacgaa agcctgcaca   29340
```

-continued

```
gcaccctgac cgaactggcg gcccgccatc gggtgcccgg cgcgcagctc gccgtcatcc   29400
acgaggggga acggttcctg gtgcacaccg gagtgtgtga caccgcctcc ggagcccccg   29460
tggagcggca caccgccttc cccgtcggct cgctgaccaa gccgttcacc gccgccctcg   29520
cgatgatcct ggtggccgac ggggacgtgg acctggacga gccgctgagg gggcagctgc   29580
cggagttcgg ggcgggcgaa ctcgtcaccc tccggcagtt gctcagccac acctcgggcc   29640
tgccctccga tgtgccggag ggcagcgacg aggccggcgg cggcgaccgt gcccgctggg   29700
tggcccggta ctgccgtacg gcggatctca cgcatgcgcc cgggacggtc ttctcgtact   29760
ccaacatcgg ctatgtcgtc gtgggccggc tcatcgaggc ggtcaccggc atgagctggc   29820
aggaggcgat cagcgcgatc ctgctcgaac ccctgggcac ccggcccgcg ttcgtcgtcg   29880
gagcccccgc caccgtccg gtggccaccg ggcacgccgt ccaggcggtc cgcgaccggg   29940
tggtgccgat accggaccag gatcttcccg aggtcgagat gcccaacggg gcgctggcgc   30000
tgagcgccga ggacctggtc ggcttcgccc ggctgtactt cgccggctgc ccggaccctc   30060
agccgctgga ccgggcgacc gccgacgaca tgtgcttcga ccagctggcc tcgatcgcca   30120
tcggcccgta cggcatggcc gacggctggg gcctgggctg ggcgaggttc gacgacggtg   30180
cggcggacgt ctacggccac aacggcaccg gcgacggcac ctcctgtcat ctgcgcttcg   30240
acccggccaa cggctccgcg gtcgcgctga ccgccaacgc caacaccggc gcccagctgt   30300
gggacgccct ggtgccccgg ctgcgggcca tgggtctggc ggtcggcgac cgcccggcgc   30360
ccgagccgcc caccaccccg ccgccggtcc ggacgactg tccgggccgc tacaccaacg   30420
gcgacaccga gttcgtggtg cagcccggcg ccgacggcgg gctgctgctg agcttcggcg   30480
gggcgccgca ctcggagctg ctgtgctccc ccgatctgcg cttcaccatg cgggagctgg   30540
gcagcggtgc ccggtccccg ggccgcttcg tgaccgatcc cgccaccggg cggatcggct   30600
acctccagat caccgggcga ctcgcccccc gacgctgaga cagggacggc cccgggatg   30660 accacggccc ccacggacgc ggagacggca cgcggcagcg cggccgtccc gctgtcccgc   30720
aaccgcgact acaacatcct gtggtccagc cagctgatgt ccgaactcgc catggagatg   30780
gccgcggtag ccgtgccgct gctgatcctc gcccggcacg gctcaccgct ccagctgggc   30840
ctggcctcct ccgcgatggc ggccgcgcac atgatctcgg tggtgccggc cggggtgatc   30900
gcggaccgct gggaccgccg ccggctgatg ctgggctgcc aggtgctacg ggtgctgggc   30960
atggtgagcc tggccggcgc gctgctgctg gaccggtacg cgttctggca tgtgctgctg   31020
gtcgtggtgc tggagggctt cctcggctcg gtcttcgacc ccgcggaaca tgccgcgctg   31080
ccccaggtgg tgccgcccga ccagctctcc acggcggtgg ccagaaacgc ggcgcgcccc   31140
tacatcgcca ccctcgtggg gccgggcgtc gccggtttcc tcttcagcgc cctgccgctc   31200
gggccgttcg cgaccaatgc ggtgatgttc gcgctgtcgt ccgtggcgct gtgctttctg   31260
cggctgcccc gggggcggtc cgccgtggtc cggaccggcg acgggcccga cagcgccgga   31320
gcggaccacg acaggccgga ccacgacgga cgggacgacg cgaacgacga cactgcgccg   31380
cggcccgggg gcgccgccca ggacttcgct gccggcttcc gctgggtgct ggggcagccg   31440
gtgatccgca ccacgatggc ctggatgatg atcacgaacc tggtcttcag ctcgctgctg   31500
atcgtgctgc tcgcgctctc gggcgaggac aaggtcggcg ccggtgagct gggtctgacg   31560
atggcctgct tcggcgccgg cggactgctc ggcgggctct tcgcggcccg gatgcacgcc   31620 gccgccggc caccggtgat cctcctcggc ttcacctgga ccgccgccct gggcgccgcc   31680
ctgatggcgg tggtgcccac cggtctgccc cagggagcgc tgctcggcct gatggcgctc   31740
```

```
ttcgccccgc tcgccaacac caccgtgctg acctaccagt tgaccgtcac cccggacgag    31800
ctgcggggcc ggatgagcgg cgtcgccggg ttctgctcgg ggggcgccgg tgtcctgggg    31860
cccgcgctcg gcggtgcgct gacggggcg ccggcgggg gcgtgacccc cgtactcatc     31920
tgcgccggct gcctggtcct ggtcgctgtc gcggccaccg cgagcccac gctgcggcgg     31980 tttcccgaca tcgcggaccg gcagccctga cctgctgcga cacggcccgt gaccggccaa    32040
cttaactcca cagtcaagga catggaacgc ccggacgaat ccgacgatgc tcgtgtatca    32100
actggagatt tccgcgcgtc ctcggtgcgg gggctggtgc ctgtccggcg gtgtgccgcg    32160
cggtcggcga aggtcccgt atgcagaccc cccacacacc gagccaggca cagtcccagc     32220
cacggcaaaa gccgcagccg ccgtcgcagt cgcagtcgca gtcgcagccg aatctgaggt    32280
ccctgaccgg attacggttc ctgggcttat tacccgtctt cctcacccat gccgcgttcg    32340
agggcgtctt cagcgacgcg gacgtgagct ggggcttcct cgacgcgatg gggaacaccg    32400
gctatgccgc ggtctcgttc ttcttcgtgc tgagcggctt tgtgatcacc tggtcctacc    32460
gctcccgcga caccacccgc acgttctggc gccgacgcgc cttccgggtc ttccccaacc    32520
atctcgtggc ctatgtgttc gcgctggctc tgatgctcgc ggcgggcgcc gccttcgacg    32580
cccccgccct gatctcccag atgttcctgg tgcacgcatg ggtgcccgac ccgctgttca    32640
tcgacaccgg caacacggtg acctggtccc tcggggtcga tgtggtgttc tacgggctct    32700
tcccggtgct gctcgtgctg gtgaacaaga tcaagccaac ccgtttgtgg tactgggccg    32760
gtgctgccgt gctcatggtg atcgccatcc ccacagtggc gctgaccctg ctcccggaca    32820
ccccggccat gtcggtgggc gatgtctccc gcagccagta ctggttcacc tacttcttcc    32880
cgctctcccg aaccgtggag tgcgtgctgg gcatgctgat ggcgcggatc gtgctgtccg    32940
gcaagtggat aggcctgcgg gtgctgcccg cctcggccct ggtggtcgtg gggtatgtcg    33000
tcgcacagca actccccttc ctctaccggc tcagcgcgt gctgatcgtg ccgatcgtgc     33060
tgctcaccgc ctccgtggcg gtggccgacg ccgagggccg ggggaccccg ctcggcggca    33120
aggtcatggt ccggctcggt gaactctcct tcgccttcta cctcgtgcac caggcgctcc    33180
tggcgtacgg gcacatcctg atcagcccga agaacgccca gggcgaggtg ctgccccgta    33240
cctgggacac gcctggcggc atccggtga tcgtcctgtc gttcgtggtg tccctgggac     33300
tcgcgtggct gctgcacaac ggggtggaga agccggtgat gcgccgttgg tcccggtcca    33360
ggcgccgcgt cacccagcag ccgccggcaa aggtgccggc aacttagctg cgaagtgaaa    33420
cgtgtggagt gcgcgaaaga tctcggccaa actccggcgc aacggggag taaggctgac     33480 cgctgccaga agtccgcgcg cgccgtggat gtccggtgcc ggcgaccacg cccggatcat    33540
ccatcagccg acagtggtgc ggccgccgtt gcggcgcacc gagccgcacc gcctgtcgcg    33600
catctggcga gaggtccgca tgcagacaag acaatccaac ccgaacctga tccctgac     33660 cggtttgcgg ttcgtggcga tgctgccggt cttcctcacc catgcggcgt tcgagggcgt    33720
cttcagcgac gcgaaggtga gctgggcgtt cctcgacgcg atggggagca ccggctatat    33780
ggccgtctcg ttcttcttcg tgctcagcgg ctttgtgatc acgtggtcgt accggcccac    33840
cgacaccgcg cgcaagttct ggcgccggcg cttcttccgg gtcttcccca accacgtcgt    33900
gacctatgcg ctcgccctcg ggctgatcgc tgcggtgggg ctgagtgtcg gcgtactgcc    33960
ctcggtcacc cagctcttcc tcgtccagtc ctgggtgccc gacccggcgt tcaccgacac    34020
cggcaacagc gtgagctggt cgctcgcggt ggatgtggtg ttctacgcgc tcttcccggt    34080
```

```
gctgctcacg ctggtgaaca agatcaagcc gaatcggctc tggtactggg tcggtggctc   34140
cgtcatcggt gtggccgtgg taccggccat cgcgctcgcc gcgctcccga gcaccccga    34200 gatgccgctc ggcggggtgt ccgtcagcca gtactggttc acctacttct tcccgctctt   34260
ccggctgctg gagtgtgtgc tcggcatgct gatggcgcgg atcgtgctgt ccggcaagtg   34320
gatacgcctg cgggtgctgc ccgccgccgt cctcgtggtg atcgcgtact acttcgccca   34380
gcaggtcccg tacctctacc ggctgagtgc ggtgacggtg ctgccggtcg cgctgctgac   34440
ggcggcggcc gcggtggcgg actccgaggg ccggggcacc ctgttcggca gcaaggtcat   34500
ggtctggttc ggcgaactct ccttcgcctt ctacctgctg cacaacctcg tcctgaagta   34560
cggccatctg ctgctcggcc acaccgagga ggagggcgag ctggtgggcc acacctgggg   34620
cgtgcccgag ggaatcgccc tgatcgccgc cgccttcgcg gtgtccctgc tgctggcctg   34680
gctgctgcac aacggagtgg agaagcaggc gatgcgccgc tggtcccgac gcaagccggc   34740
tccagtggct gaagtaacca gtgggttcta tgcgaaggac ggggcaattt agctaggaag   34800
taaaggttat ggaacgggct gtcgaaagac ggcaagatct ccactgatca ggcgttcggc   34860
accggattcg atcaatcagg tgccctatct ggagggacgt gtacgtgctg acgctccacc   34920
tgcaggatga cgacgtcgcc gcgatcgacg ctgtggctga cgaactcagc cggcgatacg   34980
actccgtgga gtccacggag ttccaggccg agagccgcct ctacgcggac gagttgccac   35040
gtcgcgtgcg acgagcgctg cacgaatacc gcagcaccga gaagtccggc atcctggtcg   35100
tcaccggcct gcccgtggac gactcggcgc tcggggcgac cccggccgac cgccggcaca   35160
agccggtgcc gtccacgtca ctgcgccagg acatcgcctt ctacctcata gccaatctgc   35220
tgggcgaccc catcggctgg gccacccagc aggacggctt catcatgcat gacgtctacc   35280
ccgtccaggg cttcgagcac gaacagatcg gctggggcag cgaggagacg ctcacctggc   35340
acaccgagga cgccttccat ccgctgcgca cggactatct cggactgatg tgtctgcgca   35400
atccggacgg cgtcgagacc accgcctgcg atatcgccga tgtcgagatc gacgacgaga   35460
cccgggagac cctctcgcag gagcgcttcc ggatcctgcc ggacgacgcg caccgcatcc   35520
acggcaaggc cccgggggac gagagcgcac gcgagagtgc gctgcgtgag cgcagccggc   35580
agcgggtggc ctcggccctg gagtcgcccg accggtggc cgtgctcttc ggggaccgcg    35640
acgacccgta tctgcggatc gacccgcact acatgcaggg cgtccaggc gagaccgagc     35700 agcgggcgct ggagaccatc ggcgccgcga tcgacgacgc catgtccggt gtcgtgctca   35760
gccccggtga catcgttttc atcgacaact accgcgtcgt ccacggacgt aagccgttcc   35820
gtgcccgctt cgacggtacg gaccgctggc tgcggcggct caacatcgcc cgggacctgc   35880
gcaagtcgcg cgaggccagg ctcgccgcca ccacccgcgt catctactga ccggctgccg   35940
ccgatcagtt agcgcaggca ccggccgaac caccgggcgc ctgcgcccag atcgcgccgc   36000
tcaacacacg gcaccgacgg ggaccgccgt catggcggtc ggccgctgtg tgcccatgcc   36060
ctcccgcatc tggggaaccc tttacgtctc tgcgaggtac ctgtgtccgg aacgcagcaa   36120
gtaaaagccg ctttggggga ttccgaaggt gacaccggaa acctcaccca actggagttc   36180
ctggctctga acagcgagtt caacatcgct gacggccacg cccggcaggc gctcacgccg   36240
ggccaaagca agatcgtcga cgatctgccg ctgctcttcg ccgagggcga gaagcggccc   36300
gtcgaagagc tcgaacgcga ggcgcaccac gccttcttca cctgccctcg gccagcacag   36360 ctaccccteg gccccggcc gggtgctgag ctgctactcc tcctcggtcg cgatggagat   36420
cctctcccgc tcgctgtccg agacgatcga gtcggtggcc ctggtccacc cgaccttcga   36480
```

-continued

```
caacatcgcc gacctgctgc gcggcaacgg cctgaagctg gtgccgctgg cggaggaccc    36540
gctgcacggc gacgacctcg acgtgagcct gctgaagtcg gtgggctgtg tcttcctcac    36600
cacgcccaac aaccccaccg gcaaggtcgt ctcccgggag cggctgaccc ggctggccga    36660
gcagtgcgcc gagcacggcg tcatcctcgc gctggacacg tccttccgcg gcttcgacac    36720
ccgcgcccac tacgaccact acgaggtgct caacgccagt ggtgtgcgct gggtggtgat    36780
cgaggacacc ggcaagctgt ggccgaccct cgacctcaag gtcggcatgc tcgtccactc    36840
cgagaacctc gcgctgccgg tcgagaagat ctactccgac atcctgctcg gtgtctcccc    36900
gctgatcctc gcgatggtcc gccgcttctc cgaggacgcc gcggccggcg gtctggagga    36960
tctgcaccgg ttcatcgccg ccaaccgtgc catggtgcgc gcggaactcg ccggtctgcc    37020
gggcgtcacg gtccccgacc ccgacagccg ggccagcgtc gagcgggtcg ccatcgatga    37080
cctgacgggc acgcaggtct gggcgaagct gcgggagcac aacgtctacg cgctcccgtg    37140
ccgcccgttc cactgggcca acccgtccga gggtgaccac accctgcggc tcgcgctggc    37200
ccggtccacg gacccgctcg cccagtccgt gcgcgcsctg cgccacgtgc tgaaacagcg    37260
ttgatgacgc ctgtcgcaga aggaggactc ccgcacggct ccgtgccctc gctgtcgcac    37320
acgcggcagt ggcggcccgg ggtcgtgcag gaggtcgccc cggccggcgt cctcgacctg    37380
ggccccggct acatcgagcc ggcactcctg cccgtacgcc tgctgcgggg cgcgtacgag    37440
caagcgctgg cggagtacgg cgccgcggcg ctgggctacg gtcacgaccc gggcgcgcag    37500
ccgctgcgcg accggctggc cgcccgcgcc ccgcggcgg acggcctccc ctgcgacccg    37560
gaccaggtgc tgctgacctc cggcacgtcc caggccctct atctgctggc gacctcgctc    37620
gcggccccgg gcgacacagt gctgacggag gagctctgtt acgacctggg acagcggata    37680
ttccgggact gctcactgcg gctccgccag gtcgccatgg acgggtcggg gatgctgccc    37740
gacgcgctgg accgcgccct gaccgagggc gcgcagcgg gcgcgaaaac cgctttcgtc    37800
tacctcaccc ccacccacca caaccccacg gccacacga tgccgctggc gcgccgccgc    37860
ctgctgctcg aagtggccgc ccggcacgat gtgctgatcg tggaggacga cgcctacacg    37920
gaactgtccc tgatccctga ccgcactccc ccgccctcgc tggccgccct ggccggctac    37980
cggcgggtgg tgcggctgtg cagcttctcc aagaccctcg gccccggact gcggctgggc    38040
tggctgctcg ccgaccggga actggccggc cggctggcca cgcacggcct gttcgtcagc    38100
gggggttcgc tcaaccacac cacctcgctc gccgtgagca ccctgctcgc gagcggcgcg    38160
tacgaccgtc atctcgacgc gttccgggcg cagttgcgtg ctcgtaggga cgcgctcgtg    38220
ggcgctctac gcgcgatgct ggacgacggg gtggagctgc gcaccccgga gggcggattc    38280
ttcctgtggc tgcgggccgg ggacggggcc gacgagcgtg agctgctcga cggcgccgcc    38340
cgggcgggcg tcaggatcgc cgccggatcg cgcttcggca caaccaggg ggccggcttg    38400
cgcctggcct tcagcttcaa cccgcccgcg ttactggagc aggccgccaa gcggctgacc    38460
accgcatggt ccggcagcac gccggacctc gagatcggag tgagatcgtg acgaccagca    38520
ccgggaccaa cggccggcac acggtggccg gtccaggcag cgccggtccc gtcgggtaca    38580
gcctgccgct ctcgccgacg ggcgagtcgg cgatgctcac accaccgccg tggcacttct    38640
ccggcgaggt cgtcatggtc gactaccgcg tcgacccgga cgcggcccga cggttcctgc    38700
cgccgggcct ggagccgggt gccgacccgg gcgccgcggc ggcggtgttc gcgacctggc    38760
agtggtgttc gcaggacgga gcggagctga ccgaccccgg tcgctgccag ttcggggagt    38820
```

```
tcctgatcct gctcagctgc gagttcgagg gccgtccat ggcgcgctgc ccgtacgcct    38880
gggtggacca ggccgtgccc atgatgcgcg gctgggtgca ggggatgccc aagcagttcg    38940
gcgtgattca ccagagccgg cccgtcacgg tcggcaaggc gggctcccgg ctggcgcccg    39000
gcggtcgttt cgacggcgcg ctgtccgtgc acggacgacg cgtcgtggag gcctcggtca    39060
ccgtggacag gtcgacggac cagccgccgg cgctgcacga tgttcccctg gcgcacaccc    39120
tggtgttccc ggagtgggtg ccctccgcg gcgggccgca ccacggctg gtcgcctccg    39180 aggtaagcga tgtggaattc tccccgatct ggaccggatc gggtgatctc acgttctttg    39240
acggactggg ggatgatttc ggggcgctcg caccgttgga agtaggtagc ggccacgtgt    39300
tctcgtacgg ggagaccttg cacggcggcc ggctgctcag cgactactcg gtatcagaac    39360
gacatcagcc atgaccacgg gggacaaagt gctgaggatc cacttcacag ttgaggacat    39420
agcaaatacg cgcatgctgg cgaccctcgg gccgctggcc gagagcgctt tcgcgctcta    39480
tctgttcggc cgtaacggcg atgtcgcctt tcacgagtgg cgtcgcagtg tccgcgccga    39540
actcggcaag gacgcggccc gcttcacggc cttgtcccag cagttccgga ccctggagga    39600
attacctgcc gccttcgccg acgccttcac gccggggcg gaccccgacc aggttccgtc    39660
cggcgaggac cggcgcggcg ccaggctgct ggccgacctg tgccgggtgg ccgtgctgcc    39720
gcactggagc ctgatccgca gtcatctcga cggtgcgcgc gagggctggg gcaggtggc    39780 catctcgcac ggtgtcgagc ggctgctggg ctccgtgcac cccaaggtcc gctggcgggc    39840
gccggtcctc gaactgcggc acgggcccaa ccgcgacatc catctggacg gtcgcgggtt    39900
gctgctgtgc ccgtcgttct tcctgtcgga gcagtcctgt tcgttcgtga cggcggtcgg    39960
caaggacgcc atgcccgccc ttgtcttccc cgtgaaggcc tcgtccaggg tggacatctg    40020
gggtacctcg gaacacgacg agcaggcgct gggcgcactg gtcgggcaca ccagggcggc    40080
cgccctggaa gcgctcgccg agggctgctc cacgggcgaa ctcgccgacc ggctggggat    40140
ctcgctggcc ggtgccagca agcatgccgc ggtgctgcga cgatccgggc tggtgaccac    40200
ctcccgtaac cgcaacaccg cgctgcacgc gctcaccct ctgggcaccg ccctgctccg    40260
cagcagcgac cgcttcatct cgccgcctac cgccccggta tcgcgcgtgc cggcgcaacg    40320
catgcggccc ttgcagctca acggcatcgg ccccggcacc aaccgggcgg cggtctgacc    40380
gcccccgcgg acgccaccg ccacgactta cggcaccct gacaggagag gacacgacag    40440
tgggcacaaa ccccttcgac gaccccgacg gccggtatct ggtgctggtc aacgaggaag    40500
accagcattc actctggccg gctttcgccg aggtgccca gggctggacg gtggcgctcg    40560
cggaaaccga ccgtcagtcc gcgctcgact tcatcaccga gcactggacc gacatgcggc    40620
cgcgcagcct ggtgcgggcg atggaagagg cttagaccag ccttgccgta tcaggcgatt    40680
tctccgggac cggcggttct ttctcaaaga tcgctgccgg ccccggggaa gaagcccca    40740 cccgcccccg ccgtacggca gaattccggc cgcataatac gactcactat agggatctcc    40800
ggcatcagga ccatgccgat cccggccgcc cggtgctcat cggtggcgag cgggagccgg    40860
gcgacccatg cgcggggcgaa cgcgcccagg gcttcctggg cggtgcggcc ggacgccggg    40920
ggcggcggct gggggtgcg ctcggcgagg ccggccagga cttcgcacac ggcccgcact    40980
tctgcctcgg ggccgcactc gccgcgtac agacggacgt tgcccctgtg acggacgtgc    41040
gccccgacca gggacggggg gcacctggtc ggggctgtct gggggtgggg ggagtgggt    41100 cagagggcgt tcaggtcgac ggcggaggcg agggccaggt agccggcgtc gctggggtgg    41160
aggccgtcct gggagatgta gccggggcgg gggcggttgg ggttcgcggg gtcggtcagg    41220
```

```
acgcggtcgg cgtcgaggac ggcgtcgtag gtgtggctgg tgcggatcca gtggttgagc   41280
tgccggcgga tcttgtcacc ggcggggtg gtgaagggga agacggcgct cctgaggggg   41340
aggatcgtca caccgatggc cttgataccg cgggcgtggg ccgcgcggac cagggcgcgg   41400
tggccgtcga tgagctgttg ggcggtcacc gggggcggt tcctggtgca ggggtcgtcc   41460
tgctgggact gggcgaggtc attggcgccg aggtggatga agacggtgcg cagggcggcg   41520
cgatcgcgca gttccttggc gaagcgggcg gtgcccttct cgccgaagca gggggaatcg   41580
tgcagcaggg ggtcacccgc caggccgcg ttggtcattc cctggggcg gccggcggcg   41640 atgaggcgtt cggcgagttt gtcggagaag cggttgtcgg tgtcggggct ggtgccgacg   41700
ccgtccatga gggagtcgcc gaagaccatg agggagtcgg ccgaacgggg cggctcctgg   41760
gtcacatcga cggccgtcag gtagtaccag gcgtgcgagg cacggcggtt gaagtcatcg   41820
gcggcggggc tgcgtagccg gtcgccgggg gcgcggtagg acgtggccgt ggtgaagcgg   41880
tgcatggtgg ccgggccggt gggggcggtg aagcgcaggg tgacggtgag ttttcgagg   41940 ttggcggtcg gcatgccac cgcgtcgctg acggtgtcgc ggcccgcggg gatggtgagg   42000
gcgggcgcat ggcggaaggt gagggtgcgt acggtgccgg ggcgcgcctt ggcctcgccg   42060
tcggacctgg cgacggtggc gccggcgatg tggaggggct tggtgccgta ggcgttggag   42120
aggcggatac ggagctcggg gccgccgacg ctgagccgga tcacctggcg cagggtctcg   42180
ttcttgaatc cctgccggga ccagttcggg gtgtcctccg tggcctcgtt cgtcgcctgc   42240
tgcatggcgg ctccccaggt ggctgtccac tgggggagt gggggcggc ggggcggcc   42300 ttctcgctcc tgagggacgg gcgggcgggg gcgaacgccc cggtcagcgc cgcggtcagg   42360
gtcacggcca gggccacgga cagcgtcatg acgatcgtcg cggggagcga gcgcgggctc   42420
cccttcgtgg tgcggccggg tgcgggccgg ccggcctcgg gtgcgtcggc cgtgtgctgc   42480
tcggccgtgt gcgggtcggt ttcgtgccgg tcggtttcgg gtcggccggc tttgtgccgg   42540
ggccacagtc gcataggagt tcctcgggtc tgttcggatc gagtcggtgc ttcaccccg   42600 ttggctttgt gtgtgccggg gcgcttacgt cgggcgtcag cgctcggcgg cgggtgggcc   42660
gggtatcccc ggccgggtgg gcaggacgtt ggcctggccg aagtaggtgg ccaccgataa   42720
gaggatctcg ttggcgctgc gcagctcgtc caactcgttt tccagttccg cgatccggcg   42780
ctcggcctgc agcggccgtg tgtgccgggt gtggtcgacg gcgagcgtgt cgggggttcg   42840 gatgggtcg gtcatggcgt gttcctctct cgggggcacc ggtgccgcgc ggccccgaac   42900
ccgtcggcag ccgcggcgcc gacggggtcg gtgggtcagt cgcggccgaa gcggcggagt   42960
acgccggtca tgaagacgat ggccatcagg gccgcggaaa ccacgacggt caccgacggc   43020
tgcacggcgg ccagttcgct gctgtcgcgc agcgcgccca tgaagtcgaa gatcggcagt   43080
ccgttggcga cgcctgtacca gagcggcagg tagaccgcct ggaagaggcg atgggtacgg   43140
ctgagcgtgc ccagggtgag ggccagggac gggatgaaca gggccccgcc gacccagccg   43200
gccagaccga accagtcggc ggcggccacc aggcggatca ggggaccgat gccggccacg   43260
gcggtgatgg tcaggcccgc ggcccattcg gcgaagaccc ggcggcgcac cgcggggtag   43320
gcgccgagca tgccgtcgac gtggtactcg tggcgctggg tgcccagccg cgaccagatc   43380
agcaccggcc agatccagga cagcggcagc atcacgcgga tgatgccgtg gatccccggg   43440
gaggagagcg cggcgatcat gaggaatgcg gcaccggtcc accaccacca gcgcacacct   43500
tgcagcagga tgcggacctc gccggcccag acgcgcaggg tcacgcgcc cggctccggg   43560
```

```
cggggtgcgca gcagcgtggc gacggtgggc cgggacgggg aagctccccc atggccctga   43620
acggacagcg gaggcgtccc cgggccgacc tcgtcgatga agaccggctg gacgacaccg   43680
tcggccgggg cctgctcggg ggtgcgcccc tggcccagcc aggttcgcgc ggggtcgaag   43740
cggccgaacc acagcgcggg gagcatggcg atcacgacgg cgatcagcag cagcgtcacc   43800
cggccgagga catagccggc ggtgggcgtg aagccgtccc aggtgaagag cccgaggggc   43860
ttgtcgaggt aggtcagacc gaggctgaac gcgccggtga catcgatgtg ctgggcgacc   43920
atgtcgtcat acatcgaccg gacgacgctg ttgacgccga tgccgtcgag gggcagaccg   43980
gggccctggc cggccgtcga gacgaccatc cagatgcaga accacaggat gttgcccagg   44040
ccggtgcgca gcagcggcag cgattcgaag aggagcgcga gggcggcggt cagcgcgacc   44100
agcggcagcg cgatgaggag gaagggctgc cagagggcga tcaggtcgat gtcgtgcgac   44160
tcgccgcggg ccagttgcat gaccagggcg gtgagcgcga gcaccacgag catggaggac   44220
agcagcatga ggttgctgag gaacttgccg agcatgtacg cggtggtgcg cagcggggtg   44280
gcggcgagca gctggccgac gcgggtgctg cggtcgcgtt cgatggagtt gcggacgatg   44340
tagaagccgc cgagggtgat ccacagaccg ctggccaggg ccgtcaccat gccgactag   44400 gcgctgttgt agatcccgcg gtgatcaccg atctgcatga tcatccattt ggcgtccgag   44460
tcgggcaccg ccacgtaacc gagggcgacg gccgcggcca ggatcacgac atacgcgggc   44520
cggcgtaccc ggtcgcggaa gtcggccacc gcaagaccgg tgagcatgcg catcattgcc   44580
tcacaccacc cgtgcctgga gcggccgttc gccgaagccc tggcggccc ggccgccgtc   44640 gaccccacgg atgatggcga ggtaggcgtc ttccaggtcg ggcgtcagct ggacggcgcc   44700
ctcgtacggc agctcgcgcg agagcagccg gatacggacg ccctcggtcg tgcggaccag   44760
gcggctgacg gtgtactgcg cctgcaccgc cgctacggac gaggggtcga ccagcacctc   44820
ccacacctgg ccgtccaccg agcgcagcag gtcctcgggg gtgccgcggc gctgcagccg   44880
gccgccggcc atcaccgcga tgtcggaggc caccgactcg acgtcggaga cgatgtgggt   44940
ggagagcatc acgaccttgt cggccgccag atcgctgagc agattgcgga acctgacccg   45000
ctcctcgggg tccagccccg cggtcggctc gtccacgatg atcacctgcg ggtcggcgag   45060
cagcacctgg gcgatgccga cccggcgcag catgccgccg gagtacttgc ccaggggacg   45120
cttgaccgct tcggtgaggt tgacgagctc caggagctca tcgatacggg ccttggcggt   45180
cttggccgag acgcccttgg ccgccgccag atacctgagg aactcgcggg aggtcaggtt   45240
cgggtagacg ccgaagtcct gcgggaggta accgagggcc cggcgcagcg cgtgggctt   45300 ggcgaccgcg tcctctccgt ggaagaggac ctttccgctg gtgggccggg tgaccgtgga   45360
ggcgatccgc atgagggacg acttgccggc gccgttgggg cccagcaggc cgagcatgcc   45420
gggttccaga cgcatcgtca ggtcgtccac ggcgtgcttg ccgcccttgt agaccttggt   45480
gatgttgacg aggtcgagca cggtcagctc ttcccggtca ggtcggtctt ctcgccgtcc   45540
ttggtcaccg cgatgccctt ggggacctcg accttgaact tggcgtcgca gatcgcgata   45600
ccgctgcagc cggcgtcgat gtccaggggt tcgcccttga ggtccactt caggtgctcg   45660 gtgcccgcgg ccgagtcgaa ccagcgggtg accttgatgt ccttgcggtc ggcggcgacc   45720
accttggtgg cgacctcgtg cgtcgtcacc ttcagggact tgcccgagta cgtgaacgac   45780
ttcgattcgg gcttcgcctt cgaggcgtcc acggagcagc cggagaggcc gagggtggcg   45840
gcgacggccg ccaccgcgac gacgagtgtg gcgggccgct tcgagatggt gcctgagaac   45900
atcggttcct ccagagtcac ggggtggtgc actcctatga ggatcccggg cccgggcggc   45960
```

```
cggcacatct gccgatcggc agatatccgc tcagcggatg gcgggcgccg gcagcaggca    46020
cctgacccgc cacccgttct cgtacgggcc cgcctccagg gagccgccca gggcgctgac    46080
gcgttcgccg aggcccgcca ggcccgtacc gccgccctgc cgggtgccgg cggacgcccc    46140
cggccctgcg ttgtcggcga ccgagacctc cacggcccgg tcggcggtcc gtccggcgaa    46200
cacctggacc cggccggcct gcggcgcatg ccgacggaca ttggtcaacg attcaagtac    46260
cacccggtac gcggtgtcct cggcctcccg cgagagggtg ccggcgacct cgtcctccag    46320
ggacagcgcc acctcggcgg cggccatgga ggagaagcgg ccgacgagct cggggaggtc    46380
ggccaagccg tagagccggg tgggcggcgg ctcgcccacc ttgcggccgt ccgcctcgcg    46440
cagcgtcgtc accgtctggt ccatggagtc cagcgcccgt agcccggcct tctcgatgcg    46500
ctgcagaagg gcgcggtgct cctcgggccc ggcgtcctcg ctgacttggg cggcctgggc    46560
ctccagaacg atgccggtca cctcgtgggc gacgaagtca tgcagatcgc gggcgacttc    46620
gaggcgctgt tcacggcgcg ccagcaccac ggcatacgcc cggcggttgt ccagcgaccg    46680
cagatagagc cccacacccg tcgcgcaggc cgccgggatc agggccagca aggccgcgaa    46740
gaccgattcc ttgagcccgg cggtggggc gtgcagggtg aagcgcaggg gcagcaggat    46800
gacggctgcg ccggtcagcg gggcgacgat gcccacccgg gggctgggca catgacgtac    46860
cacccgctcc aggagaacga gcagcgcgac cgtctcgaac gggtaccaga ggatcaccag    46920
gccgggctgc ccgaagtagc cgacgtccgc ggcgagggag agcagcgcga cgccgcccgc    46980
cgcctgggcc agggagatcc ggccggtcgg ccagcaagt atcgatacgg ccagcgtcaa    47040
tgcggccatg accgccagca gataggcgct cggtggcgct atgacggcgg gggcgagcat    47100
cattgccgcg gccaccccgc accaccggcg gcgcttttgc cggggaggaa cgtcgtaatc    47160
catgagggcg aggctacgca cattccccgg gttgcgcggc ggcaagcaca gcgcggaaat    47220
taccgcatct gccggacggc agatttccgc gggacggcat cggggtttct gccgggtggc    47280
gtgctgcccg atgccggccg cgggttttca ccccggggtc tgcccggtgg catatccgag    47340
ctcccaggcc cgcaccgcga ccccgacgcg attgcgtacc tgtagctttc gctgaatgct    47400
cgcgacatgg gtcttgaccg tgccgcggga gatgaacaac tcgcgggcga tatcggaatt    47460
ggtcttgccc tcggcgacct tcccggcgat ctccacctcc cgctcggtca gcaccgagtc    47520
acggcggcgg gggcggcggc cggtcgtggg gccggtgaca tgctggagca gccggacagt    47580
gatcgacggg ctgatcaggc tgtcgccggc catcgccgcc cggaccgcct cgaccagcag    47640
cgtcggcccc gagcgcttga gcaggaaccc cgaggcgccg aagcgcagcg cggggtacac    47700
gtactcgtcc aggtcgaagg tcgtcaccac gacgacccgg accgggttgg ccgcggcggg    47760
gtcggccagc aggcgggtca cctccaggcc gtccatccgc ggcatccgga tgtcgaccag    47820
cgccacatcg ggtttgagcg tgcgccccat ctccaccgcg tccacgccgt ttgccgcctc    47880
gccgaccact tccatgtcgg gctggctctc cacgatgcgg cgtattccgc ggcggaccat    47940
ctcctggtcg tcggcgatca gcaagcgaat agtcacgggc aggaattc    47988
```

<210> SEQ ID NO 2
<211> LENGTH: 2747
<212> TYPE: PRT
<213> ORGANISM: Streptomyces hygroscopicus

<400> SEQUENCE: 2

```
Met Gly Glu Trp Arg Asp Arg Arg Leu Asp Glu Leu Phe Ala Glu Gln
1               5                   10                  15
```

-continued

```
Ala Ala Arg Thr Pro Glu Arg Thr Ala Val Val Phe Glu Gly Arg Ala
            20                  25                  30

Val Ser Tyr Arg Glu Leu Asp Ala Arg Ala Glu Arg Leu Ala Ala Val
        35                  40                  45

Leu Ala Gly Arg Gly Ala Gly Pro Glu Arg Phe Ile Ala Leu Leu Leu
    50                  55                  60

Pro Arg Ser Ala Glu Leu Ile Val Ala Ile Leu Ala Val Leu Lys Ser
65                  70                  75                  80

Gly Ala Gly Tyr Ile Pro Ile Asp Pro Glu Tyr Pro Ala Asp Arg Ile
                85                  90                  95

Ala Tyr Ile Leu Gly Asp Ala Arg Pro Val Ala Thr Ile Thr Thr Ala
            100                 105                 110

Glu Val Arg Asp Gly Leu Pro Asp Pro Asp Thr Gly Ser Gly Thr Asp
        115                 120                 125

Trp Leu Ile Leu Asp Glu Ser Gly Tyr Glu Gln Glu Pro Ala Gly Ala
    130                 135                 140

Arg Pro Gln Pro Ala Pro Ala Ala Pro Arg Ser Ala Glu Asn Pro Ala
145                 150                 155                 160

Tyr Val Ile Tyr Thr Ser Gly Ser Thr Gly Arg Pro Lys Gly Val Val
                165                 170                 175

Ile Pro His Ser Asn Val Gly Arg Leu Leu Ser Ser Thr Ala His Trp
            180                 185                 190

Tyr Gly Phe Asp Glu Gln Asp Val Trp Pro Leu Phe His Ser Phe Ala
        195                 200                 205

Phe Asp Val Ser Val Trp Glu Ile Trp Gly Ala Leu Leu His Gly Gly
    210                 215                 220

Lys Leu Val Val Val Pro His Ala Val Thr Arg Ala Pro Ala Asp Phe
225                 230                 235                 240

Leu Arg Leu Leu Val Glu Glu Arg Val Thr Val Leu Asn Gln Thr Pro
                245                 250                 255

Ser Ala Phe Tyr Gln Leu Met Ala Ala Asp Arg Glu Asn Pro Ala Leu
            260                 265                 270

Gly Ala Gln Leu Ala Leu Arg Tyr Val Val Phe Ala Gly Glu Ala Leu
        275                 280                 285

Asp Leu Gly Lys Leu Ala Asp Trp Tyr Glu Arg His Asp Asp Arg Ala
    290                 295                 300

Pro Thr Leu Val Asn Met Tyr Gly Ile Thr Glu Thr Thr Val His Ser
305                 310                 315                 320

Ser Phe Leu Ala Leu Asp Lys Glu Gly Ala Ala Gly Ala Thr Gly Ser
                325                 330                 335

Ala Val Gly Val Ala Leu Pro Asp Leu Thr Phe His Val Leu Asp Glu
            340                 345                 350

Asp Leu Arg Pro Val Pro Val Gly Ala Glu Gly Glu Leu Tyr Val Ala
        355                 360                 365

Gly Pro Gly Leu Ala Arg Asn Tyr Ala Gly Arg Pro Gly Leu Thr Ala
    370                 375                 380

Glu Arg Phe Val Ala Cys Pro Phe Gly Pro Pro Gly Ala Arg Met Tyr
385                 390                 395                 400

Arg Ser Gly Asp Leu Val Arg Pro Leu Pro Asp Gly Gly Leu Glu Tyr
                405                 410                 415

Leu Arg Arg Ser Asp Asp Gln Val Lys Ile Arg Gly Phe Arg Ile Glu
            420                 425                 430
```

```
Leu Gly Glu Ile Ser His Ala Leu Ala Gln Asp Pro Ser Val Asp Gln
        435                 440                 445

Ala Thr Val Val Arg Asp Glu Ala Ser Gly Glu Arg Arg Leu Val
    450                 455                 460

Ala Tyr Val Val Pro Ala Gly Ser Ala Arg Pro Thr Pro Ser Arg Leu
465                 470                 475                 480

Arg Ala Ala Leu Ala Thr Arg Leu Pro Gly Tyr Met Val Pro Thr Ala
                485                 490                 495

Phe His Val Met Pro Ala Phe Pro Leu Thr Ala Asn Gly Lys Leu Asp
            500                 505                 510

Arg Arg Ala Leu Pro Ala Pro Thr Arg Gln Asp Ser Val Asp Ala Asp
        515                 520                 525

Tyr Ala Ala Pro Glu Gly Ala Thr Glu Ala Leu Ala Ala Ile Trp
    530                 535                 540

Arg Glu Val Leu Gly Val Glu Gln Ile Gly Ala Asp Asp Phe Phe
545                 550                 555                 560

Glu Leu Gly Gly Asp Ser Leu Ser Val Val Arg Ala Leu Ser Arg Met
                565                 570                 575

Arg Thr Gly Leu Gly Leu Arg Leu Thr Ala Ala Glu Phe Phe Ala Thr
            580                 585                 590

Pro Thr Val Arg Ala Leu Ala Ala Arg Arg Glu Arg Gly Thr Ile Gly
        595                 600                 605

Ala Pro Glu Gln Ile Pro Ala Ala Pro Arg Thr Gly Ala Leu Pro Leu
    610                 615                 620

Ser Phe Thr Gln Gln Arg Phe Trp Leu Phe His Glu Leu Asp Pro Gly
625                 630                 635                 640

Glu Val Glu Tyr Asn Val His Ser Ala Leu Arg Leu Arg Gly Thr Leu
                645                 650                 655

Asp Leu Pro Ala Leu Arg Thr Ala Leu Gly Gly Leu Ile Ala Arg His
            660                 665                 670

Glu Pro Leu Arg Thr Thr Val Val Ser Asp Asp Gly Arg Pro Thr Ala
        675                 680                 685

Val Ile Ala Pro Pro Glu Gly Phe Pro Val Pro Leu Thr Val Glu Asp
    690                 695                 700

Leu Ser Ala Leu Thr Gly Asp Asp Gln Glu Ala Ala Gln Arg Arg Leu
705                 710                 715                 720

Leu Ala Glu Glu Val Ala Arg Pro Phe Asp Leu Ala Ala Gly Pro Val
                725                 730                 735

Leu Arg Val Leu Val Ile Arg Arg Gly Glu Arg Asp His Ala Leu Val
            740                 745                 750

Ile Gly Val His His Leu Ala Thr Asp Gly Trp Ser Met Gly Leu Leu
        755                 760                 765

Thr Asp Glu Leu Ser Ala Arg Tyr Asp Ala Ala Arg Arg Gly Val Pro
    770                 775                 780

Ala Ala Leu Glu Pro Leu Pro Val His Tyr Ser Asp Tyr Ala Ala Trp
785                 790                 795                 800

Gln Arg Ala Thr Val Asp Asp Gly Arg Leu Val Pro Gln Ile Asp Tyr
                805                 810                 815

Trp Arg Asp Arg Leu Ala Asp Val Ala Pro Leu Gln Leu Pro Thr Asp
            820                 825                 830

Arg Pro Arg Pro Ala Leu Lys Thr Ser Ala Gly Ala Ala His Arg Phe
        835                 840                 845

Thr Leu Asp Arg Arg Leu Val Ala Ala Leu Lys Glu Leu Ser Ala Ala
```

-continued

```
            850                 855                 860
His Gly Ala Thr Leu Phe Met Thr Leu Thr Ala Ala Leu Gln Val Leu
865                 870                 875                 880

Leu Ala Arg Tyr Ser Gly Gln Gln Asp Ile Ala Leu Gly Thr Ala Val
                885                 890                 895

Ser Gly Arg Asp His Pro Gln Val Glu Arg Leu Val Gly Ala Phe Ile
                900                 905                 910

Asn Thr Val Val Leu Arg Ser Asp Val Arg Gly Glu Leu Pro Phe His
            915                 920                 925

Glu Phe Leu Gly Glu Val Arg Glu Thr Val Leu Gly Ala Phe Ala His
930                 935                 940

Gln Asp Leu Pro Phe Asp Arg Leu Val Asp Ala Leu Gly Ala Glu Arg
945                 950                 955                 960

Asp Pro Ser Arg Thr Pro Leu Val Gln Ala Met Leu Leu Gln Asn
            965                 970                 975

Ala Pro Ala Gly Ala Glu Glu Phe Ala Gly Leu Arg Thr Glu Thr Val
                980                 985                 990

Ala Leu Pro Arg Pro Ala Ala Ile Phe Asp Leu Thr Val Asp Cys Thr
                995                 1000                1005

Glu Arg Ala Gly Ala Leu Glu Val Met Val Glu Tyr Asn Thr Asp
            1010                1015                1020

Leu Phe Asp Ala Thr Thr Ile Glu Arg Leu Ser Gly His Leu Arg
            1025                1030                1035

Val Leu Leu Asp Ala Val Cys Ala Ala Pro Arg Arg Gln Val Arg
            1040                1045                1050

Asp Leu Pro Leu Leu Pro Ala Ala Glu Arg Asp Thr Leu Leu Thr
            1055                1060                1065

Gly Trp Asn Asp Thr Ala Ala Ala Leu Pro Thr Thr Leu Gly Val
            1070                1075                1080

His Arg Gln Phe Ala Glu Arg Ala Arg Thr Thr Pro Asp Ala Leu
            1085                1090                1095

Ala Val Thr His Cys Gly Gln Thr Leu Thr Tyr Ala Gln Leu Asp
            1100                1105                1110

Ala Arg Ala Asn Gln Leu Ala His Tyr Leu Gly Ala Leu Gly Val
            1115                1120                1125

Gly Arg Gly Thr Pro Val Val Leu Asn Leu Ala Arg Lys Pro Gln
            1130                1135                1140

Leu Ile Val Ala Met Leu Ala Val Leu Lys Ala Gly Gly Ala Tyr
            1145                1150                1155

Val Pro Thr Ala Leu Asp Thr Pro Ala Ala Arg Leu Gly His Leu
            1160                1165                1170

Leu Glu Glu Thr Gly Thr Pro Val Leu Leu Thr Thr Ala Arg Gln
            1175                1180                1185

Ala Gly Ala Leu Pro Pro Thr Glu Ala Ser Val Ile Asp Leu Asp
            1190                1195                1200

Ala Ala Gly Pro Asp Ile Ala Arg His Pro Glu His Asp Pro Gln
            1205                1210                1215

Val Ala Thr Arg Pro Glu Asp Leu Ala Tyr Ile Val Tyr Thr Ser
            1220                1225                1230

Gly Ser Thr Gly Arg Pro Lys Gly Val Ala Val Pro His Ser Ala
            1235                1240                1245

Leu Thr Asp Tyr Cys Ala Trp His Asn Asp Ala Leu Asp Val Gly
            1250                1255                1260
```

-continued

```
Pro Glu Asp Arg Gly Ser Ser Val Val Gly Leu Ala Phe Asp Val
    1265                1270                1275
Ala Val Gly Glu Val Trp Pro Tyr Leu Cys Ala Gly Ala Arg Val
    1280                1285                1290
Asp Gln Pro Asp Gln Glu Thr Leu Asp Asp Pro Thr Ala Leu Val
    1295                1300                1305
Glu Trp Phe Ala Glu Asn Gly Thr Thr Val Ala Tyr Leu Pro Thr
    1310                1315                1320
Pro Arg Ile Glu Ser Leu Leu Asp Val Ala Ala Ile Thr Thr Thr
    1325                1330                1335
Arg Leu Arg Thr Val Leu Val Ile Gly Asp Ser Leu Arg Arg Arg
    1340                1345                1350
Pro Gln Pro Gly Leu Pro Phe Thr Leu Leu Asn Ala Tyr Gly Pro
    1355                1360                1365
Ala Glu Ala Thr Val Ala Ala Thr Gln Ala Val Val Glu Pro Leu
    1370                1375                1380
Gly Pro Asp Ala Pro Ala Gly Leu Pro Ser Ile Gly Ala Pro Leu
    1385                1390                1395
Tyr Asn Thr Ala Ala Tyr Val Leu Asp Asp Arg Leu Cys Pro Val
    1400                1405                1410
Pro Val Gly Val Pro Gly Glu Leu Tyr Leu Ala Gly Ala Gly Leu
    1415                1420                1425
Ala Gln Gly Tyr Gln Gly Arg Pro Asp Leu Thr Ala Glu Arg Phe
    1430                1435                1440
Val Gly Cys Pro Phe Gly Pro Gly Thr Arg Met Tyr Arg Thr
    1445                1450                1455
Gly Asp Ile Val Arg Trp Leu Pro Asp Gly Thr Leu Asp Phe Leu
    1460                1465                1470
Gly Arg Ile Asp Asn Gln Val Lys Leu Arg Gly Tyr Arg Ile Glu
    1475                1480                1485
Leu Gly Glu Ile Glu Ser Val Leu Ala Arg Arg Glu Glu Leu Ser
    1490                1495                1500
Gln Val Phe Val Thr Val Arg Glu Pro Ser Pro Gly Arg Arg Ser
    1505                1510                1515
Leu Val Ala Tyr Leu Val Ala Asp Arg Gly Thr Ala Pro Asp Pro
    1520                1525                1530
Glu Glu Leu Ala Gly Tyr Ile Ala Ser Val Leu Pro Glu Tyr Met
    1535                1540                1545
Val Pro Ser Ser Phe Val Leu Leu Asp Ala Leu Pro Leu Thr Ala
    1550                1555                1560
Asn Gly Lys Ile Asp Arg Arg Ala Leu Pro Glu Pro Glu Pro Ala
    1565                1570                1575
Gly Gly Glu Gly Ala Ala Tyr Val Ala Pro Gly Asn Glu Val Glu
    1580                1585                1590
Glu Thr Leu Ala Ala Ile Trp Ala Glu Val Leu Gly Val Glu Arg
    1595                1600                1605
Val Gly Val Gln Asp Asn Phe Phe Ala Leu Gly Gly Asp Ser Ile
    1610                1615                1620
Ser Gly Leu Gln Thr Ala Val Arg Ala Arg Arg Ala Gly Leu Arg
    1625                1630                1635
Leu Ala Ser Lys Asp Leu Phe Gln Arg Gln Thr Ile Ala Ala Leu
    1640                1645                1650
```

-continued

Ser Pro Val Val Thr Val Glu Arg Thr Ala Asp Ala Asp Pro
1655            1660            1665

Ala Pro Ser Asp Arg Pro Thr Ala Pro Phe Ala Leu Ser Gly Leu
1670            1675            1680

Asp Arg Val Gly Val Glu Arg Leu Thr Ala Asp Gly Gly Pro Ala
1685            1690            1695

Glu Asp Ala Tyr Pro Leu Thr Pro Met Gln Ser Gly Leu Leu Phe
1700            1705            1710

His Thr Leu Met His Ala Glu Arg Gly Met Tyr Ile Glu Gln Phe
1715            1720            1725

His Phe Ala Leu His Ser Ile Arg Glu Pro Glu Leu Leu Ala Thr
1730            1735            1740

Ala Trp Gln Arg Val Val Asp Arg Thr Pro Val Leu Arg Thr Ser
1745            1750            1755

Leu Ala Trp Asp Gly Leu Ala Glu Pro Leu Gln Val Val Arg Thr
1760            1765            1770

Gly Val Arg Ile Pro Val Ala Gln Leu Asp Trp Thr Ala Leu Asp
1775            1780            1785

Glu Ala Gly Gln Arg Gln Ala Leu Glu Arg Tyr Leu Thr Glu Asp
1790            1795            1800

Arg Thr Arg Gly Leu Asp Leu His Thr Ala Pro Leu Ala Arg Ile
1805            1810            1815

Ala Val Ala Arg Leu Gly Gly Asp Gln Val Arg Leu Val Trp Thr
1820            1825            1830

Phe His His Leu Leu Leu Asp Gly Trp Ser Val Val Gln Val Leu
1835            1840            1845

Ser Glu Val Leu Gly Glu Tyr Ala Ala Leu Ala Asp Gly Ile Pro
1850            1855            1860

Tyr Thr Pro Gln Leu Arg His Thr Tyr Ala Glu Phe Val Gly Gln
1865            1870            1875

Leu Ala Gly Gln Asp His Thr Ala Ala Glu Lys Tyr Trp Arg Ala
1880            1885            1890

Ala Leu Thr Gly Arg Glu Ser Pro Thr Pro Leu Pro Tyr Asp Arg
1895            1900            1905

Pro Arg Pro Asp Ala His Gln Ala Ala Pro Asp Ala Glu Leu Lys
1910            1915            1920

Leu Arg Leu Pro Ala Ala Val Thr Gly Arg Leu Gly Thr Ala Ala
1925            1930            1935

Lys Arg Ala Gly Val Thr Met Asn Thr Val Val Gln Gly Leu Trp
1940            1945            1950

Ala Leu Leu Leu Ala Arg His Ser Gly Glu Arg Asp Val Leu Phe
1955            1960            1965

Gly Ala Thr Val Ala Gly Arg Pro Asp Asp Leu Ala Gly Ala Glu
1970            1975            1980

Ser Val Ile Gly Leu Phe Ile Asn Thr Leu Pro Val Arg Val Asp
1985            1990            1995

Val Asp Pro Asp Ala Gly Leu Leu Ser Trp Leu Arg Arg Val Gln
2000            2005            2010

Asp Glu Gln Ala Glu Ala Arg Ala His Glu Gln Val Ser Leu Ala
2015            2020            2025

Gln Val Gln Gly Trp Ala Pro Glu Arg Ala His Gly Gly Leu Phe
2030            2035            2040

Asp Ser Val Leu Ala Phe Glu Asn Phe Pro Ala Asp Leu Gly Pro

-continued

```
             2045                2050               2055
Ala Gly Asn Tyr Gly Leu Arg Leu Asp Ala Ile Glu Ala Ser Asn
         2060                2065               2070

Thr Ser Asn Tyr Pro Leu Asn Ala Ile Val Gln Leu Asn Glu Glu
         2075                2080               2085

Leu Thr Val Leu Leu Arg Tyr Asp Thr Ala Leu Phe Asp Ala Asp
         2090                2095               2100

Thr Val Ala Arg Leu Ala Gly His Leu His Thr Leu Leu Glu Glu
         2105                2110               2115

Thr Ala Glu Asn Pro Asp Arg Arg Val Gly Glu Leu Pro Leu Leu
         2120                2125               2130

Thr Ala Ala Glu Arg His Thr Ile Val His Thr Trp Thr Asp Thr
         2135                2140               2145

Ala Ser Asp Tyr Ser Val Asp Arg Arg Leu Asp Ala Val Ile Ala
         2150                2155               2160

Glu Gln Ala Ala Ala Arg Pro Thr Ala Ile Ala Val Val Asp Gly
         2165                2170               2175

Glu Arg Gln Leu Ser Tyr Gly Glu Leu Asp Arg Arg Ala Asn Gln
         2180                2185               2190

Leu Ala His His Leu Arg Ala Ala Gly Val Gly Arg Asp Ala Leu
         2195                2200               2205

Val Gly Ile Ala Val Glu Arg Ser Ala Glu Val Val Val Ala Ile
         2210                2215               2220

Leu Gly Thr Leu Lys Ala Gly Ala Ala Tyr Val Pro Leu Asp Pro
         2225                2230               2235

Glu Phe Pro Ala Gln Arg Leu Ala Thr Met Leu Ser Glu Ser Arg
         2240                2245               2250

Pro Ala Val Leu Leu Thr Gln Glu His Leu Leu Ala Gly Leu Pro
         2255                2260               2265

Pro Thr Asp Ala Arg Val Val Cys Val Asp Arg Asp Leu Ala Ala
         2270                2275               2280

Ile Glu Ala His Pro Thr Ala Ala Pro Val Ser Gly Gly Asp Ala
         2285                2290               2295

Gly Asp Leu Ala Tyr Val Thr Tyr Thr Ser Gly Ser Thr Gly Arg
         2300                2305               2310

Pro Lys Gly Val Met Val Glu His Arg Ser Leu Phe Asn Ile Ile
         2315                2320               2325

Thr Glu Ala Gly Arg Leu Tyr Asp Leu Gly Pro Asp Ser Arg Met
         2330                2335               2340

Leu Gln Phe Tyr Thr Met Ser Phe Asp Gly Gly Val Trp Glu Val
         2345                2350               2355

Phe Leu Thr Leu Thr Ala Gly Ala Thr Leu Val Ile Ala Asp Pro
         2360                2365               2370

Glu Ala Arg Gln Ser Pro Ala His Leu Ala Glu Gln Leu Arg Ala
         2375                2380               2385

Glu Ser Ile Thr Ala Leu Thr Leu Pro Pro Ala Val Ala Ser Val
         2390                2395               2400

Leu Asp Ala Ala Ser Leu Pro Gly Ile Arg Ser Leu Gly Leu Ala
         2405                2410               2415

Gly Asp Val Leu Ala Pro Glu Leu Ala Arg Glu Trp Ala Arg Gly
         2420                2425               2430

Arg Arg Leu Phe Asn Ile Tyr Gly Pro Ser Glu Ala Thr Leu Ser
         2435                2440               2445
```

```
Val Ala Leu His Arg Val Asp Pro Gly Ala Ala Gly Arg Gln Val
    2450                2455                2460

Pro Leu Gly Pro Pro Val Pro Asn Thr Arg Phe His Val Leu Asp
    2465                2470                2475

Glu Arg Leu Ala Val Val Pro Val Gly Val Thr Gly Glu Leu Tyr
    2480                2485                2490

Ile Gly Gly Ala Gly Leu Ala Arg Gly Tyr Leu Gly Arg Pro Asp
    2495                2500                2505

Leu Thr Ala Gln Arg Phe Val Ala Asp Pro Phe Gly Pro Pro Gly
    2510                2515                2520

Ser Arg Leu Tyr Arg Thr Gly Asp Leu Ile Arg Trp Thr Pro Gln
    2525                2530                2535

Gly Arg Leu Glu Phe Ala Gly Arg Val Asp Asn Gln Val Lys Ile
    2540                2545                2550

Arg Gly Tyr Arg Val Glu Pro Ala Glu Val Glu Ser Ala Leu Leu
    2555                2560                2565

Arg Gln Pro Gly Val Ala Glu Ala Val Val Ile Ala Arg Asp Asp
    2570                2575                2580

Asp Thr Gly His Lys Arg Leu Val Ala Tyr Val Val Pro Asp Gly
    2585                2590                2595

Ser Gly Thr Ala Pro Glu Arg Ala Ala Leu Leu Arg Ala Leu Gly
    2600                2605                2610

Gly Gln Leu Pro Gly Tyr Met Val Pro Ser Ala Leu Val Thr Leu
    2615                2620                2625

Pro Glu Leu Pro Leu Gly Pro Thr Gly Lys Val Asp Val Arg Ala
    2630                2635                2640

Leu Pro Ala Pro Asp Pro Ala Ala Gly Thr Ala Asp Arg Ile
    2645                2650                2655

Pro Pro Arg Thr Pro Thr Glu Glu Ala Leu Ala Leu Ile Trp Val
    2660                2665                2670

Glu Leu Leu Gly Leu Glu His Val Gly Val Glu Asp Asn Phe Phe
    2675                2680                2685

Asp Leu Gly Gly Asp Ser Ile Thr Ser Leu Arg Leu Met Ser Arg
    2690                2695                2700

Met Gly Gly Ala Phe Gly Val Asp Val Ser Pro Arg Asp Phe Phe
    2705                2710                2715

Asp Ala Pro Thr Ile Ala Ala Leu Ala Glu Arg Leu Glu Glu Lys
    2720                2725                2730

Ile Leu Ala Gln Leu Glu Glu Ala Val Gly Gly Gly Ala Leu
    2735                2740                2745

<210> SEQ ID NO 3
<211> LENGTH: 8244
<212> TYPE: DNA
<213> ORGANISM: Streptomyces hygroscopicus

<400> SEQUENCE: 3
atgggtgagt ggcgcgatcg ccgcctggac gaattgttcg ccgagcaggc cgcgagaaca      60
ccggagcgta ccgcggtggt cttcgagggc cgggcggtga gttatcggga actcgacgcc     120
cgcgccgagc ggctggccgc tgtgctggcc ggccgcggcc gggacccga gcggttcatc      180 gcgctgctgc tgccccgctc cgccgaactg atcgtggcca tcctcgccgt actgaagtcc     240
ggcgccggat acatcccgat cgacccggag tacccggccg accgcatcgc ctacatcctc     300
```

-continued

| | |
|---|---|
| ggcgacgcgc gcccggtggc gacgatcacc accgccgagg tgcgggacgg tctgccggac | 360 |
| ccggacaccg gctccgggac cgactggctg atcctggacg agtccgggta cgagcaggag | 420 |
| ccggccgggg cgcgcccgca gcccgccccg gccgccccgc ggtccgcgga gaaccccgcc | 480 |
| tacgtcatct acacctccgg ctcgaccggc cggcccaagg gcgtggtgat cccgcacagc | 540 |
| aatgtgggac ggctgctgtc gtccaccgcc cactggtacg gcttcgacga gcaggacgtc | 600 |
| tggccgctgt tccactcctt cgccttcgat gtctcggtct gggagatctg gggcgcgctg | 660 |
| ctgcacggcg gcaagctggt cgtcgtcccg catgccgtca cccgcgcccc ggccgacttc | 720 |
| ctgcggctgc tggtcgagga acgggtcacc gtcctgaacc agacgccttc ggcgttctac | 780 |
| cagctgatgg ccgccgaccg ggagaacccc gcgctcggcg cccaactcgc cctgcgttat | 840 |
| gtggtgttcg cgggtgaggc gctggacctg ggcaagctcg ccgactggta cgagcggcac | 900 |
| gatgaccggg cgccgacgct ggtcaacatg tacggcatca ccgagaccac cgtgcactcc | 960 |
| tcgttcctcg cactggacaa ggagggcgcg gccggcgcca cgggcagcgc cgtcggcgtc | 1020 |
| gccctccccg acctgacctt ccatgtcctc gacgaggacc tgcggcccgt cccggtcggc | 1080 |
| gcggagggcg agctgtatgt ggccgggccc gggctggcac ggaactacgc gggccggccg | 1140 |
| gggctgaccg cggagcgctt cgtggcctgc ccgttcggcc cgcccggggc ccgtatgtac | 1200 |
| cgctcgggcg acctggtgcg gccgctgccg gacggcggcc tcgaatacct gcggcgcagc | 1260 |
| gacgaccagg tcaagatccg cggtttccgg atcgaactgg gtgagatctc gcacgcactg | 1320 |
| gcccaggacc cctcggtcga ccaggccacg gtggtggtcc gcgacgaggc gtcgggcgag | 1380 |
| cgcaggctgg tggcgtacgt cgttccggcc ggctccgccc gtcccacccc gtcccggctg | 1440 |
| cgtgccgcgc tggccacccg cctgccggc tacatggtcc ccaccgcctt ccacgtcatg | 1500 |
| ccggccttcc cgctgaccgc caacggcaag ctggaccgca gggcgctgcc cgcgcccacc | 1560 |
| cgccaggaca cgtcgacgc cgactacgcc gcccccgagg gcgccaccga ggaggcgctg | 1620 |
| gccgccatct ggcgcgaggt gctcggcgtc gaacagatcg gtgccgacga cgacttcttc | 1680 |
| gagctcggcg gtgactcgct gtccgtggtg cgggcgctgt cgcggatgcg gaccggcctg | 1740 |
| gggctgcgcc tgacggccgc ggagttcttc gccaccccca ccgtccgggc actggccgcg | 1800 |
| cgccgcgagc ggggcacgat cggcgcgccg gagcagatac cggccgcgcc gcgtaccggc | 1860 |
| gcgctgccgc tgtccttcac ccagcagcgg ttctggctct ccacgaact cgaccccggc | 1920 |
| gaggtcgagt acaacgtcca ctccgcgctg cggctgcgcg caccctcga cctccccgcg | 1980 |
| ctgcgcaccg cgctcggcgg gctgatcgcc cgccatgagc cgctgcggac gaccgtggtc | 2040 |
| tccgacgacg gccgcccac cgcggtcatc gccccgcccg agggcttccc ggtcccgctc | 2100 |
| accgtcgagg atctctccgc gctgaccggc gacgaccagg aggccgccca gcggcgactg | 2160 |
| ctggccgagg aggtcgcccg gcccttcgac ctggccgccg gccggtgct gcgggtgctg | 2220 |
| gtgatccgcc gcggcgagcg cgatcacgcc ctggtgatcg gggtgcatca cctcgccacc | 2280 |
| gacggctggt cgatggggct gctcaccgac gagctgagcg cgcgctacga cgccgcgcgc | 2340 |
| cgcggggtgc ccgccgcgct ggagccgctg ccggtccact acagcgacta cgccgcctgg | 2400 |
| cagcgcgcca ccgtggacga cggccggctg gtgcccaga tcgactactg gcgcgaccgg | 2460 |
| ctggcggatg tggcaccgct gcaactgccc accgaccggc ccggccgc gctgaagacc | 2520 |
| tcggccggtg cggcgcaccg cttcaccctc gaccgccggc tggtcgccgc cctcaaggag | 2580 |
| ctgagcgccg cccatggcgc cacgctcttc atgaccctga ccgccgcgtt gcaggtgctg | 2640 |
| ctcgcccgct actccggaca gcaggacatc gcgctgggca ccgccgtctc cggccgggac | 2700 |

```
cacccgcagg tggagcggct ggtcggcgcg ttcatcaaca ccgtggtgct ccgctccgac    2760
gtgcgcggcg agctgcccTt ccacgaattc ctcggggagg tacgggagac ggtgctgggc    2820
gccttcgcgc accaggacct tccgttcgac cggctcgtgg acgcgctggg cgccgagcgc    2880
gacccgagcc gtaccccgct ggtccaggcg atgctgctgc tgcagaacgc cccggccggt    2940
gcggaggagt cgccgggct gcgcaccgag ccgtcgcgc tgccgcgccc ggccgcgatc    3000
ttcgacctga cggtggactg cacggagcgg gccggggcgc tggaggtgat ggtcgagtac    3060
aacaccgatc tgttcgacgc gacgaccatc gagcggctct cgggccatct gcgggtgctg    3120
ctggacgccg tatgcgcggc accgcggcgc caggtgcgcg atctgccgct gctgccggcg    3180
gccgaacgcg acacgctgct gaccggctgg aacgacaccg ccgccgcact gccgacgacg    3240
ctcggggtgc accgccagtt cgccgagcgg gcccgcacca ccccggacgc gctcgccgtc    3300
acacactgcg gacagaccct cacctacgcc caactcgacg cgcgcgccaa ccagttggcg    3360
cactacctgg gcgctctcgg cgtcggccgg ggcaccccg tggtgctgaa cctggcgcgc    3420
aagccgcagc tgatcgtggc gatgctcgcg gtgctcaagg ccggcggcgc gtacgtaccg    3480
accgcgctgg acacccggc ggcacggctc gggcatctcc tggaggagac cggcaccccc    3540
gtgctgctga ccaccgcgcg gcaggccgga gcgctgcccc cgaccgaggc gagcgtcatc    3600
gacctcgacg cggccgggcc ggacatcgcc cggcatccgg agcacgaccc ccaggtggcg    3660
acccggcccg aggacctcgc gtacatcgtc tacacctccg ggtccaccgg ccgccccaag    3720
ggcgtcgcgg tgccgcacag cgcgctgacc gactactgcg cctggcacaa cgacgcgctg    3780
gacgtcggcc ccgaggaccg cgggtcgtcc gtggtcggcc tggccttcga cgtcgcggtc    3840
ggcgaggtgt ggccgtatct gtgcgcgggc gcccgcgtgg accagccga ccaggagacg    3900 ctggacgatc cgacggcgct ggtggagtgg ttcgccgaga acggcaccac ggtcgcctat    3960
ctgccgaccc cgcgcatcga atccctgctg gacgtagcgg cgatcaccac cacccggctg    4020
cgcaccgtcc tggtcatcgg cgactcgctg cgccgcaggc cgcagccgg actgccgttc    4080 accctgctca acgcctacgg gccgcgcgag gcgacggtgg ccgccaccca ggcggtggtc    4140
gagcccctgg gacccgacgc gcccgccggg ctgccgtcca tcggcgcccc gctgtacaac    4200
accgccgcct atgtcctcga cgaccggctg tgcccggtcc ccgtcggggt gcccggcgag    4260
ctgtacctcg ccggcgcggg tctggcgcag ggctatcagg gccgccccga cctgaccgcg    4320
gagcgcttcg tcggctgccc cttcgggccg cccggaaccc ggatgtaccg cacgggtgac    4380
atcgtgcgat ggctaccgga cggcacccTg gacttcctcg gccggatcga caaccaggtc    4440
aaactgcgcg gctaccgcat cgaactcggc gagatcgaga gcgtgctggc ccgccgcgag    4500
gagctctcgc aggtgttcgt cacggtccgc gagccgtccc ccggccgccg gtccctggtc    4560
gcctacctcg tcgccgaccg gggcaccgcg cccgacccgg aggagctcgc cggatacatc    4620
gcctccgtac tcccggagta catggttccg tcctccttcg tactgctcga cgcgctgccg    4680
ctgaccgcga acggcaagat cgaccggcgg gcgctgcccg agccggagcc ggccggcggc    4740
gagggcgccg cgtatgtcgc gccggcaac gaggtcgagg agaccctggc cgccatctgg    4800
gccgaggtgc tcggcgtcga acgggtcggc gtgcaggaca acttcttcgc cctcggcggc    4860
gactcgatca gcggtctgca gaccgccgta cgggcccgcc gggccgggct gcgactggcc    4920
tccaaggacc tcttccagcg ccagaccatc gcggcgctga gccccgtggt gacggtggag    4980
cggaccacgg cggacgccga ccccgcaccg tccgaccggc cgaccgcgcc gttcgcgctc    5040
```

```
agcggtctgg accgggtcgg tgtggagcgg ctgaccgcgg acggcggccc ggccgaggac    5100
gcctacccgc tgaccccgat gcagagcggg ctgctcttcc acaccctgat gcacgccgaa    5160
cgcggcatgt acatcgagca gttccacttc gccctgcaca gcatccgcga gccggagctg    5220
ctggccaccg cctggcagcg ggtcgtcgac cgcacccctg tgctccgtac gtcactggcc    5280
tgggacggcc tcgccgaacc gctccaggtc gtgcgcaccg cgtccggat accggtggca    5340
cagctcgact ggacggcact ggacgaggcc ggacagcggc aggccctgga gcggtatctg    5400
accgaggacc gcacgcgcgg gctcgatctg cacaccgcgc cactcgcccg gatcgccgtc    5460
gcccgcctgg gcggcgacca ggtccggctg gtgtggacgt ccaccatct gctgctggac    5520
ggctggagcg tcgtacaggt gctgtccgag gtgctcggcg agtacgccgc gctcgccgac    5580
ggcatcccgt acaccccgca actgcggcac acctacgccg agttcgtcgg ccagctggcg    5640
gggcaggacc acaccgccgc cgagaagtac tggcgtgccg cgctcaccgg ccgtgagtcg    5700
cccaccccg tgccgtacga ccggccgcgc cccgacgccc atcaggccgc ccccgacgcc    5760
gagctgaagc tgcggctgcc ggccgcggtg accggccgac tgggcaccgc ggcgaagcgg    5820
gccggggtga cgatgaacac cgtggtgcag ggcttgtggg cgctgctgct ggcccgccac    5880
agcggtgagc gggacgtact gttcggcgcc acggtcgccg gccggcccga cgatctggcg    5940
ggcgcggaat cggtgatcgg cctgttcatc aacacccttc cggtgcgcgt cgacgtcgat    6000
ccggacgccg gtctgctgag ctggctgcgc cgggtgcagg acgagcaggc cgaggcgcgc    6060
gcccatgagc aggtctcgct cgcccaggtg cagggctggg cgccggagcg ggcgcacggc    6120
ggactgttcg acagcgtgct ggccttcgag aacttcccgg ccgacctcgg tcccgccggg    6180
aactacgggc tgcggctcga cgccatcgag gccagcaaca cctccaacta cccgctcaac    6240
gccatcgttc agctcaacga agagctgacc gtgctgctgc gctacgacac cgcgctgttc    6300
gacgcggaca ccgtggcgcg gctggccggc catctgcaca cgctgctgga ggagaccgcc    6360
gagaaccccg accgccgggt cggcgagctg cccctgctca ccgccgccga gcggcacacc    6420
atcgtgcaca cctggaccga caccgcctcg gactactcgg tcgaccgccg gctgacgcg    6480
gtcatcgccg aacaggccgc ggcccggccg accgcgatcg ccgtcgtcga cggtgaacgg    6540
cagctgagtt acggcgagtt ggaccgccgc gccaaccagc tggcacacca tctgcgcgcc    6600
gcgggcgtgg gccgggacgc cctcgtcggg atcgccgtcg agcgcagcgc ggaggtcgtc    6660
gtggccatcc tcggcacgct caaggcgggc gccgcgtatg tgccgctcga ccccgaattc    6720
cccgcgcagc ggctcgccac catgctgtcc gagtcccggc ccgcggtcct gctcacccag    6780
gaacacctgc tggcgggct gccgccgacg gacgcccggg tggtgtgcgt ggaccgggac    6840
ctggcggcca tcgaggcgca ccccaccgcc gcgccggtct ccggcggcga cgccggcgac    6900
ctggcctatg tcacctacac ctcgggctcc accggccgcc caagggcgt catggtcgag    6960
caccgctcgc tgttcaacat catcaccgag gccgacggc tctacgacct gggccccgac    7020
agccggatgc tgcagttcta cacaatgagc ttcgacggcg gcgtctggga ggtcttcctg    7080
acgctgaccg ccggcgccac cctcgtcatc gcggaccccg aggcccgcca gagcccggcc    7140
cacctcgccg agcagctgcg cgcggagtcg atcaccgcgc tgacgctgcc gcccgcggtg    7200
gcctcggtgc tggacgcggc ctcgctgccc ggcatacgca gctgggggct cgccggggat    7260
gtgctcgcgc ccgaactcgc ccgggagtgg gcgcggggc gccggctgtt caacatctac    7320
gggcccagcg aggcgaccct gtccgtcgcc ctgcaccgcg tcgacccgg ggccgccggg    7380
cgccaggtgc cgctcggacc gccggtgccc aacacccgtt tccatgtgct cgacgagcgg    7440
```

-continued

```
ctggccgtgg tcccggtcgg ggtgaccggc gagctctaca tcggcggtgc gggcctggcc      7500
cgcggctacc tgggccgccc cgacctgacc gcgcagcgct tcgtcgccga cccgttcgga      7560
ccgccgggat cccgtctcta ccgcaccggt gacctgatcc gctggacccc gcaggggcgg      7620
ctggagttcg ccgggcgggt ggacaaccag gtcaagatcc gcggctaccg tgtcgagccc      7680
gccgaggtgg agagcgcact gctgcggcag cccggcgtcg cggaggcggt ggtgatcgcc      7740
cgggacgacg acaccggcca aagcggctg gtcgcctatg tcgtaccgga cgggagcgga      7800
accgccccgg aacgcgccgc cctgctgcgc gccctgggcg ccaactccc cggctacatg      7860 gtgccgtcgg ccctcgtcac cctgcccgag ctaccgctcg accgaccgg caaggtcgat      7920 gtgcgggcgc tgccggcacc ggatccggcc gccggcggca ccgccgaccg catcccgccc      7980
cgcaccccca cggaagaggc actggccctc atctgggtgg agctgctcgg gctcgaacac      8040
gtcggcgtcg aggacaactt cttcgacctc ggcggcgact ccatcaccag cctgcggttg      8100
atgtcgcgga tgggcggcgc gttcggtgtg gacgtctcac cccgcgactt cttcgacgcc      8160
cccaccatcg ccgcccttgc cgagcgccta gaggaaaaga tcctggcgca gttggaagaa      8220
gccgtcggag gcggcgccct atga                                             8244
```

<210> SEQ ID NO 4
<211> LENGTH: 3668
<212> TYPE: PRT
<213> ORGANISM: Streptomyces hygroscopicus

<400> SEQUENCE: 4

```
Met Thr Ser Ser Ala Ala Asp Gln Pro Asp Asn Pro Asn Thr Thr Thr
1               5                   10                  15

Pro Ala Ser Arg Ala Glu Arg Thr Ala Ala Leu Pro Ala His Val Gln
                20                  25                  30

Glu Leu Leu Arg Ala Arg Leu Ala Gly Arg Ala Ala Thr Gly Gly
            35                  40                  45

Ala Asp Thr Ile Pro Arg Ile Gly His Asp Gly Pro Val Ala Leu Ser
        50                  55                  60

Pro Ala Gln Glu Arg Leu Trp Tyr Leu His Glu Leu Glu Pro Glu Ser
65                  70                  75                  80

Asn Glu Tyr Asn Thr Leu Arg Val Leu Arg Leu Arg Gly Asp Leu Asp
                85                  90                  95

Pro Gly Ala Leu Ser Ala Ala Leu Ser Glu Ile Val Ala Arg His Gly
                100                 105                 110

Ala Leu Arg Thr Thr Phe Gly Ser Arg Glu Gly His Ala Glu Gln Thr
            115                 120                 125

Val His Pro Val Pro Thr Pro Leu Pro Leu Val Asp Leu Ser Ala
        130                 135                 140

Ala Asp Asp Gly Glu Arg Asp Ala Leu Arg Thr Leu Leu Gln Tyr
145                 150                 155                 160

Glu Ala Arg Arg Pro Phe Asp Leu Arg Arg Gly Pro Val Leu Arg Ala
                165                 170                 175

Gln Leu Ile Arg Leu Ala Ala Asp Asp His Val Leu Ala Leu Ala Leu
                180                 185                 190

His His Ile Val Thr Asp Gly Trp Ser Met Gly Val Leu Thr Gly Glu
            195                 200                 205

Leu Thr Ala His Tyr Ala Ala Thr Leu Arg Gly Ala Pro Ala Val Leu
        210                 215                 220
```

-continued

```
Pro Glu Leu Pro Val Ser Tyr Leu Asp Val Ala Val Trp Gln Arg Asp
225                 230                 235                 240

Gln Leu Ser Ser Ala Arg Leu Arg Glu Gly Leu Asp His Trp Arg Arg
            245                 250                 255

Glu Leu Ala Gly Leu Val Pro Leu Asp Leu Pro Thr Thr Trp Gln Arg
        260                 265                 270

Pro Pro Val Arg Thr Ser Ala Gly Ala Leu His Ser Phe Glu Ile Pro
    275                 280                 285

Pro Ala Val Ala Ala Arg Leu Arg Glu Leu Gly Arg Glu Gln Gly Ala
    290                 295                 300

Thr Leu Phe Met Ala Leu Val Ala Ala Val Gln Leu Leu Leu Ser Arg
305                 310                 315                 320

Trp Ser Gly Gln Arg Asp Ile Ala Val Gly Thr Ala Ala Ala Gly Arg
                325                 330                 335

Gly Arg Thr Glu Thr Glu Asn Leu Ile Gly Phe Phe Val Asn Asn Leu
            340                 345                 350

Val Leu Arg Ser Arg Ile Asp Glu Thr Arg Ser Phe Thr Glu Leu Leu
        355                 360                 365

Arg Ala Val Arg Ala Thr Val Leu Asp Ala Phe Ala His Glu Asp Val
    370                 375                 380

Pro Phe Gln Arg Val Val Glu Ala Leu His Pro Glu Arg Asp Leu Ser
385                 390                 395                 400

Arg Pro Pro Leu Ala Glu Val Ala Val Asn Leu His Asn Thr Pro Arg
                405                 410                 415

Thr Asp Thr Glu Leu Pro Gly Leu Arg Ile Glu Met Pro Pro
            420                 425                 430

Val Phe Ala Ser Ser Met Asp Leu Ser Phe Asp Phe Thr Glu Arg Asp
    435                 440                 445

Asp Arg Leu Glu Gly His Leu Thr Tyr Asn Thr Asp Leu Phe Ala Ala
    450                 455                 460

Asp Ala Ala Arg Met Ala Ala Gln Leu Val Thr Leu Leu Glu Asp
465                 470                 475                 480

Leu Thr Arg Arg Pro Ala Val Pro Val Ala Gly Leu Ala Val Leu Pro
                485                 490                 495

Ala Ala Glu His Arg Arg Val Thr Glu Glu Trp Pro His Ser Gly Pro
            500                 505                 510

Gly Arg Glu Pro Arg Thr Ala Pro Glu Leu Phe Ala Ala Gln Val Ala
        515                 520                 525

Arg Thr Pro Asp Ala Asp Ala Leu Val Ser Asp Glu Glu Thr Leu Ser
    530                 535                 540

Tyr Ala Glu Leu Asp Gly Arg Ile Asn Gln Trp Ala Arg Leu Leu Leu
545                 550                 555                 560

Ala Arg Gly Ala Gly Pro Glu Thr Leu Val Ala Val Ala Leu Pro Arg
                565                 570                 575

Ser Ala Gln Met Val Thr Ala Ile Leu Ala Ile Gln Lys Thr Gly Ala
            580                 585                 590

Ala Tyr Leu Pro Leu Asp Pro Lys Ser Pro Ala Glu Arg Asn Arg Leu
        595                 600                 605

Met Ile Glu Asp Ala Arg Pro Leu Leu Val Leu Thr Ser Ala Gly Phe
    610                 615                 620

Gly Asp Gly Ala Glu Leu Gly Ala Pro Ala Leu Phe Leu Asp Asp Pro
625                 630                 635                 640

Asp Thr Arg Ala Ala Ala Gly Glu Leu Ser Ala Gly Pro Leu Ala Ala
```

-continued

```
                645                 650                 655
Ala Glu Leu Pro Ala Pro Leu Leu Pro Gly His Pro Ala Tyr Val Ile
            660                 665                 670
Tyr Thr Ser Gly Ser Thr Gly Arg Pro Lys Gly Val Val Thr His
            675                 680                 685
Thr Gly Val His Gly Leu Val Ala Ala Gln Ser Ala His Phe Arg Thr
            690                 695                 700
Gly His Gly Ala Arg Val Leu Ser Phe Ala Ser Leu Gly Phe Asp Ala
705                 710                 715                 720
Ala Phe Ser Glu Leu Gly Met Ala Leu Leu Ser Gly Gly Ala Leu Val
            725                 730                 735
Val Val Asp Gln Glu Arg Ile Leu Pro Gly Gln Pro Leu Ala Asp Val
            740                 745                 750
Leu Ala Glu His Arg Val Thr His Val Thr Leu Pro Pro Ser Ala Leu
            755                 760                 765
Ser Ala Leu Thr Pro Gly Thr Leu Pro Lys Asp Leu Thr Leu Val Val
            770                 775                 780
Ala Gly Glu Ala Cys Pro Pro Ala Val Ala Arg Thr Trp Ser Ala His
785                 790                 795                 800
His Arg Met Ile Asn Ala Tyr Gly Pro Thr Glu Ser Thr Val Cys Ala
                805                 810                 815
Ser Met Ser Ala Ala Leu Thr Pro Asp Thr Val Ser Gly Asp Ser Val
                820                 825                 830
Pro Ile Gly Arg Pro Leu Ser Gly Val Arg Val Ser Val Leu Asp Asp
                835                 840                 845
Arg Leu Arg Pro Val Pro Ala Gly Val Pro Gly Glu Val Tyr Leu Ser
            850                 855                 860
Gly Ala Ala Leu Ala Arg Gly Tyr Leu Gly Arg Leu Ala Leu Thr Ala
865                 870                 875                 880
Glu Arg Phe Val Ala Asp Pro Tyr Gly Pro Pro Gly Ser Arg Met Tyr
                885                 890                 895
Arg Thr Gly Asp Arg Ala Arg Trp Leu Ala Gly Gly Asp Leu Asp Tyr
                900                 905                 910
Leu Gly Arg Thr Asp Asp Gln Val Lys Leu Arg Gly Phe Arg Ile Glu
            915                 920                 925
Leu Gly Glu Val Glu Ala Val Leu Ser Arg His Asp Gly Val Gly Ala
            930                 935                 940
Val Ala Ala Thr Val His Lys Asp Glu Arg Gly Thr Arg Arg Leu Val
945                 950                 955                 960
Ala Tyr Val Val Pro Ala Arg Glu Asp Ala Ala Asp Pro Ala Arg Leu
                965                 970                 975
Arg Glu Phe Ala Arg Glu Val Leu Pro Glu His Met Val Pro Ser Val
            980                 985                 990
Phe Val Pro Leu Asp Arg Leu Pro  Leu Asn Ala Asn Gly Lys Val Asp
                995                 1000                1005
Arg Arg Ala Leu Pro Ala Pro  Asp Ile Arg Arg Asp  Glu Gly Ser
    1010                1015                1020
Ala Arg Ile Ala Pro Arg Thr  Pro Ala Glu Glu Thr  Leu Ala Arg
    1025                1030                1035
Ile Trp Ser Glu Val Leu Gly  Val Thr Asp Ile Gly  Val Glu Asp
    1040                1045                1050
Asn Phe Phe Asp Leu Gly Gly  Asp Ser Ile Leu Ser  Leu Gln Val
    1055                1060                1065
```

-continued

```
Val Ala Arg Ala Arg Ala Ala Gly Leu Arg Leu Thr Ala Lys Gln
    1070                1075                1080

Thr Phe Leu Arg Gln Thr Ile Ala Asp Leu Ala Ala Asp Ala Val
    1085                1090                1095

Ala Glu Thr Asp Pro Ala Ala His Gly Ala Ala Asn Asp Gly Pro
    1100                1105                1110

Val Thr Gly Glu Leu Pro Leu Thr Pro Ile Gln His Trp Phe Phe
    1115                1120                1125

Asn Ser Leu Gly Asp Ser Leu Glu Gln Phe Asn Gln Ser Leu Tyr
    1130                1135                1140

Leu Glu Leu Ala Glu Gly Pro Asp Leu Pro Ala Leu Arg Ala Ala
    1145                1150                1155

Leu Ala Ala Leu Thr Glu Gln His Asp Ala Leu Arg Leu Arg Ala
    1160                1165                1170

Val Ser Glu Asp Gly Gln Trp Arg Leu His His Ala Pro Ala Glu
    1175                1180                1185

Thr Gly Gln Leu Leu Glu His Leu Asp Leu Ser Gly Val Ser Pro
    1190                1195                1200

Asp Glu Gln Asp Ala Ala Met Ala Ala Ala Val Asp Ala Ala Gln
    1205                1210                1215

Arg Asp Phe Arg Leu Ser Glu Gly Pro Leu Leu Arg Ala Arg Leu
    1220                1225                1230

Phe Thr Leu Gly Asp Ala Arg Pro Pro Arg Leu Tyr Leu Val Ala
    1235                1240                1245

His His Leu Val Ile Asp Gly Met Ser Trp Arg Ile Leu Leu Ala
    1250                1255                1260

Asp Leu Glu Thr Gly Tyr Arg Leu Ala Ala Asp Gly Arg Pro Ile
    1265                1270                1275

Asp Leu Gly Pro Arg Thr Thr Ser Phe Arg Asp Trp Ser Arg Arg
    1280                1285                1290

Leu Ser Arg His Val Ala Asp Gly Gly Leu Asp Ala Glu Leu Pro
    1295                1300                1305

Tyr Trp Lys Gly Val Gln Asp Ala Ala Arg Glu Thr Ala Pro Leu
    1310                1315                1320

Pro Val Asp Thr Gly Gly Leu Pro Asp Arg Gln Gly Ala Gln Glu
    1325                1330                1335

Glu Pro Gly Glu Asn Thr Ala Gly Ser Ala Arg Thr Val Ser Val
    1340                1345                1350

Gln Leu Ser Ala Ala Gly Thr Glu Ala Leu Leu Arg Gln Val Pro
    1355                1360                1365

Glu Ala Tyr Arg Thr Gln Ile Asn Asp Val Leu Leu Ser Ala Leu
    1370                1375                1380

Gly Arg Val Leu Thr Asp Trp Ala Gly Gly Glu Arg Val Leu Ile
    1385                1390                1395

Ala Leu Glu Gly His Gly Arg Glu Glu Leu Phe Asp Glu Val Asp
    1400                1405                1410

Leu Thr Arg Thr Val Gly Trp Phe Thr Thr Leu Phe Pro Val Ala
    1415                1420                1425

Leu Arg Met Pro Ala Asp Arg Asp Trp Gly Thr Val Leu Lys Ser
    1430                1435                1440

Val Lys Glu Gln Leu Arg Ala Val Pro His Asn Gly Leu Gly His
    1445                1450                1455
```

-continued

```
Gly Ala Leu Arg His Leu Ala Gly Pro Asn Ser Pro Leu Glu Asp
    1460                1465                1470

Gly Pro Glu Pro Glu Val Ser Phe Asn Tyr Leu Gly Gln Leu Asp
    1475                1480                1485

Val Ser Ala Asp Arg Thr Gly Leu Ala Arg Ala Met Leu Thr Ser
    1490                1495                1500

Glu Gly Ala Glu Arg Ala Ala Gly Gln His Arg Ala Gln Leu Leu
    1505                1510                1515

Glu Ile Asn Gly Val Val Thr Gly Gly Arg Leu Glu Phe His Trp
    1520                1525                1530

Thr Tyr Ser Val Asn Arg His Arg Ala Glu Thr Val Glu Arg Leu
    1535                1540                1545

Ala Ala Gly Phe Met Thr Ala Leu Glu Ala Ile Val Ala His Cys
    1550                1555                1560

Ala Ala Pro Gly Ser Gly Gly Ala Thr Pro Ser Asp Phe Pro Leu
    1565                1570                1575

Ala Ala Leu Asp Gln Ala Thr Val Asp Lys Ile Ala Gly Asp Gly
    1580                1585                1590

Arg Thr Val Glu Asp Ile Tyr Pro Leu Thr Ala Met Gln Ser Gly
    1595                1600                1605

Met Leu Phe His Ala Leu Ser Glu Ser Gly Arg Asp Pro Tyr Thr
    1610                1615                1620

Gly His Phe Gly Val Arg Val Asp Gly Ile Thr Asp Pro Gly Ala
    1625                1630                1635

Leu Ala Ala Ala Trp Gln Gln Val Val Asp Arg Thr Pro Ala Leu
    1640                1645                1650

Arg Thr Ala Ile Val Trp Gln Asp Val Ala Glu Pro Leu Gln Val
    1655                1660                1665

Val His Ala Ala Arg Val Pro Val Thr His His Asp Leu Arg
    1670                1675                1680

Ser Leu Thr Glu Gln Glu Arg Gln Ala Ala Leu Asp Arg Leu Trp
    1685                1690                1695

Glu Arg Arg Glu Glu Thr Val Ile Asp Leu Ala Val Ala Pro Ala
    1700                1705                1710

Leu Arg Leu Thr Leu Val Arg Leu Thr Asp Ser Ala Val Gln Met
    1715                1720                1725

Phe Trp Thr Ser His His Ile Leu Met Asp Gly Trp Ser Phe Ala
    1730                1735                1740

Gly Leu Leu Ser Glu Val Cys Ala Gln Tyr Thr Ala Leu Thr Gly
    1745                1750                1755

Gly Pro Arg Val Ala Ala Pro Ala Arg Arg Pro Tyr Arg Asp Tyr
    1760                1765                1770

Val Gly Trp Leu Ala Glu Gln Asp Gln Pro Ala Ala Glu Ala His
    1775                1780                1785

Trp Arg Ser Val Val Asp Gly Phe Thr Val Pro Thr Pro Leu Pro
    1790                1795                1800

Tyr Asp Arg Gln Pro Val Lys Ala His Gly Thr Arg Ser Ser Arg
    1805                1810                1815

Glu Val Arg Leu Gln Leu Ser Ala Glu Arg Ser Gly Arg Leu Ser
    1820                1825                1830

Glu Ala Ala Arg Ser Ala Arg Leu Thr Val Asn Thr Leu Val Gln
    1835                1840                1845

Gly Ala Trp Ala Ile Leu Leu Ala Arg Tyr Gly Gly Val Arg Asp
```

-continued

```
              1850                1855                1860

Val Cys Phe Gly Thr Thr Val Ser Gly Arg Pro Ala Thr Leu Pro
    1865                1870                1875

Gly Ala Glu Ser Met Ala Gly Leu Phe Ile Asn Thr Val Pro Val
    1880                1885                1890

Arg Ala Thr Ile Asp Gly Ala Gly Ala Gly Asp Gly Ala Ala Thr
    1895                1900                1905

Gly Thr Val Glu Trp Leu Arg Arg Leu Gln Ser Glu Gln Leu Asp
    1910                1915                1920

Ser Arg Gln His Glu His Val Ser Leu Ala Gln Ile Gln Arg Trp
    1925                1930                1935

Ser Gly Val Pro Ala Gly Thr Asn Leu Phe Asp Ser Ile Val Val
    1940                1945                1950

Phe Glu Asn Tyr Pro Tyr Asp Ser Asp Ala Ala Lys Tyr Gly
    1955                1960                1965

Leu Thr Leu Gly Thr Phe Gln Gly Asp Glu Val Thr Asn Tyr Ala
    1970                1975                1980

Leu Thr Leu Thr Ala Tyr Val Ala Asp Glu Leu His Leu Asn Leu
    1985                1990                1995

Gly Tyr Asp Pro Asp Leu Phe Asp Glu Ala Thr Val Glu Arg Met
    2000                2005                2010

Ala Gly His Leu Ala Thr Leu Leu Asp Ala Val Ala Ala Ala Pro
    2015                2020                2025

His Thr Pro Val Asp Asp Leu Pro Leu Leu Asp Ala Ala Glu His
    2030                2035                2040

His Arg Leu Leu Thr Glu Trp Asn Asp Thr Ala Ala Gly Phe Pro
    2045                2050                2055

Pro Pro Arg Pro Val His Glu Leu Phe Ala Glu Arg Ala Ala Arg
    2060                2065                2070

Thr Pro Asp Ala Val Ala Val Ser Asp Ala Thr Arg Gln Leu Thr
    2075                2080                2085

Phe Ala Glu Leu Glu Thr Arg Ala Asn Gln Leu Ala His His Leu
    2090                2095                2100

Ala Gly Leu Gly Val Ala Pro Gly Thr Leu Val Gly Val Cys Ala
    2105                2110                2115

Asp Arg Gly Val Asp Ala Val Val Ala Leu Leu Gly Val Leu Arg
    2120                2125                2130

Ala Gly Gly Ala Phe Val Pro Leu Asp Pro Ala Tyr Pro Ala Glu
    2135                2140                2145

Arg Leu Gln Val Met Leu Glu Asp Ala Ala Val Pro Val Val Val
    2150                2155                2160

Thr Glu Glu Arg Leu Leu Asp Arg Thr Ala Gly His Asp Ala Thr
    2165                2170                2175

Thr Val Cys Leu Asp Arg Asp Leu Pro Leu Leu Glu Leu Pro
    2180                2185                2190

Ala Arg Pro Pro Tyr Thr Ala Val Ala Pro Asp Asp Leu Ala Tyr
    2195                2200                2205

Val Val Tyr Thr Ser Gly Thr Gly Arg Pro Lys Gly Val Met
    2210                2215                2220

Val Glu His Arg His Val His Met Val His Ala Trp Asp Arg
    2225                2230                2235

Arg Tyr Gly Leu Ala Ala Leu Gln Pro Arg Ala Leu Ser Val Ser
    2240                2245                2250
```

```
Ser Ile Ser Val Asp Leu Phe Phe Ser Asp Phe Leu Leu Ser Ala
    2255            2260            2265

Leu Phe Gly Gly Thr Met Val Ile Cys Pro Gln Asp Ala Val Ala
    2270            2275            2280

Asp Gln Val Ala Leu Thr Asp Leu Leu Leu Lys Ser Arg Ala Gln
    2285            2290            2295

Leu Met Val Thr Val Pro Thr Leu Ala Arg Ala Val Ala Glu
    2300            2305            2310

Leu Ala Trp Arg Gly Val Thr Pro Glu Ala Leu Arg Val Leu Met
    2315            2320            2325

Val Gly Ser Glu Gly Trp Pro Ala Asp Ala Ala Glu Ile Leu
    2330            2335            2340

Ala Gly Leu Ala Pro Gly Thr Val Leu Val Asn Ala Tyr Gly Ser
    2345            2350            2355

Thr Glu Thr Thr Val Asp Ser Thr Val Phe Gln Leu Gly Arg Asp
    2360            2365            2370

Pro Leu Gly Asp Ala Ala Phe Val Pro Val Gly Arg Pro Leu Ala
    2375            2380            2385

Asn Thr Arg Ile Tyr Val Leu Asp Glu Arg Met Arg Pro Val Pro
    2390            2395            2400

Thr Gly Val Val Gly Glu Cys Tyr Ile Gly Gly Asp Gly Val Ser
    2405            2410            2415

Arg Gly Tyr Leu Gly Arg Pro Glu Leu Thr Ala Glu Arg Phe Leu
    2420            2425            2430

Asp Asp Pro Phe Ala Pro Glu Pro Gly Ala Arg Met Tyr Arg Thr
    2435            2440            2445

Gly Asp Leu Ala Arg Trp Arg Ala Asp Gly Asn Leu Glu Cys Leu
    2450            2455            2460

Gly Arg Val Asp Asp Gln Val Lys Ile Arg Gly Phe Arg Val Glu
    2465            2470            2475

Leu Gly Glu Val Glu Ala Ala Leu Ala Arg His Pro Ala Ile Asp
    2480            2485            2490

Ser Ala Ala Ala Ile Arg Lys Asp Asp Gly Gly Pro Ala Arg
    2495            2500            2505

Leu Val Gly Tyr Val Val Pro Ala Ala Gly His Thr Pro Asp Leu
    2510            2515            2520

Ala Glu Leu Arg Ala Phe Ala Ala Glu Arg Leu Pro Ser Pro Ala
    2525            2530            2535

Val Pro Thr Ala Tyr Met Val Leu Asp Ala Leu Pro Met Thr Pro
    2540            2545            2550

Ser Gly Thr Val Ala Arg Arg Ala Leu Pro Ala Pro Ala Gly Ala
    2555            2560            2565

Gln Asp Ala Ala Arg Pro Tyr Thr Ala Pro Gly Ser Ala Thr Glu
    2570            2575            2580

Leu Leu Leu Cys Gly Ile Trp Gln Glu Val Leu Gly Val Glu Arg
    2585            2590            2595

Val Gly Val His Asp Asn Phe Phe Asp Leu Gly Gly Asp Ser Ile
    2600            2605            2610

Leu Ser Ile Arg Val Ile Ser Arg Ile Arg Ala Thr Leu Gly Val
    2615            2620            2625

Ala Pro Ser Pro Arg Gln Leu Phe Asp Thr Pro Thr Val Ala Gly
    2630            2635            2640
```

```
Leu Ala Ala Thr Leu Gly Arg Asp Asp Pro Ser Ala Ala Ala Asp
2645                2650                2655

Val Pro Leu Glu Pro Ala Asp Arg Gly Ala Pro Leu Pro Leu Ser
2660                2665                2670

Ser Ala Gln Gln Arg Gln Trp Phe Leu His Asn Phe Asp Pro Asp
2675                2680                2685

Ser Ser Glu Tyr His Ile Val Thr Gly Leu Arg Leu Asp Gly Asp
2690                2695                2700

Leu Asp Val Ala Ala Leu Arg Gly Ala Leu Asn Gly Leu Val Ala
2705                2710                2715

Arg His Glu Ala Leu Arg Thr Thr Tyr Ala Ala Thr Gly Glu Gly
2720                2725                2730

Ala Glu Gln Ile Val His Pro Ala Gly Glu Val Val Cys Glu Arg
2735                2740                2745

Thr Asp Leu Ser Glu Val Pro Glu Asp Gln Arg Glu Asp Thr Leu
2750                2755                2760

Arg Gly His Ile Asp Arg Ala Ala Ala Arg Pro Phe Gly Leu Thr
2765                2770                2775

Glu Gly Pro Val Leu Arg Ala Glu Leu Phe Arg Leu Gly Ala Arg
2780                2785                2790

Asp His Leu Leu Leu Val Ile His His Ile Ala Thr Asp Gly
2795                2800                2805

Val Ser Met Gln Val Leu Thr Glu Glu Leu Gly Val His Tyr Ala
2810                2815                2820

Ala Ala Leu Asp Gly Thr Pro Pro Ala Leu Pro Ala Leu Pro Val
2825                2830                2835

Ser Tyr Ala Asp Tyr Ala Ala Trp Gln Arg Arg Met Leu Ser Gly
2840                2845                2850

Pro Ala Leu Asp Gly His Leu Ala Tyr Trp Gln Glu Arg Leu Ala
2855                2860                2865

Gly Val Arg Pro Leu Glu Leu Pro Thr Asp Arg Pro Arg Pro Ala
2870                2875                2880

Val Arg Ser Ser Ala Gly Arg Met Leu Leu Ile Glu Ile Glu Pro
2885                2890                2895

Arg Val Ala Ala Gly Leu Lys Glu Leu Ala Arg Arg His Asp Ala
2900                2905                2910

Thr Leu Phe Met Ala Leu Thr Ala Ala Val Gln Leu Leu Leu Ala
2915                2920                2925

Arg Tyr Thr Gly Gln Pro Asp Ile Val Val Gly Thr Pro Ala Ala
2930                2935                2940

Gly Arg Gly Arg Gln Glu Leu Glu Gly Leu Val Gly Leu Phe Val
2945                2950                2955

Asn Thr Val Ala Leu Arg Ser Thr Val Asp Glu Ser Gly Thr Phe
2960                2965                2970

Asp Ala Phe Leu Gly Ala Val Arg Asp Thr Val Leu Glu Ala Phe
2975                2980                2985

Val His Glu Asp Val Pro Phe Asp Arg Leu Val Glu Val Leu Arg
2990                2995                3000

Pro Arg Arg Asp Pro Ser Arg Asn Ala Leu Val Glu Val Phe Val
3005                3010                3015

Gly Leu Glu Thr Asp Arg Ser Ala Pro Pro Ala Leu Pro Gly Leu
3020                3025                3030

Thr Val Thr Glu Val Pro Phe Val Ser Gly Glu Val Ser His Asp
```

-continued

```
              3035                3040                3045

Leu Ser Phe Asp Phe Val Asp Gly Pro Asp Gly Leu Lys Ala Ala
    3050                3055                3060

Ile Gly Tyr Ser Thr Ala Leu Phe Asp Asp Gly Thr Val Glu Arg
    3065                3070                3075

Met Ala Gly Gln Phe Gln Ala Leu Leu Ala Ala Val Leu Glu Asp
    3080                3085                3090

His Arg Ala Leu Ala Asp Ile Ala Pro Ala Asp Glu Ala Glu Val
    3095                3100                3105

Arg Arg Leu Ala Glu Leu Arg Gln Ala Ala Pro Ser Glu Pro Asp
    3110                3115                3120

Ala Ser Glu Thr Asp Gly Ala Pro Ala Ala Tyr Arg Ala Pro Gly
    3125                3130                3135

Thr Ala Ala Glu Arg Ala Leu Ala Glu Ile Trp Ala Ala Val Leu
    3140                3145                3150

Gly Val Pro Arg Val Gly Thr Asp Asp Asn Phe Phe Gln Leu Gly
    3155                3160                3165

Gly Asp Ser Leu Leu Ser Ile Gln Ala Val Gln Arg Met Arg Gln
    3170                3175                3180

Ala Gly Leu Ala Val Thr Thr Lys Asp Leu Phe Val His Gln Ser
    3185                3190                3195

Ile Ala Pro Leu Ala Ala Leu Ala Glu Glu Arg Ala Ala Asp Arg
    3200                3205                3210

Pro Glu Ala Pro Gln Ala Gln His Asp Asp Ala Gly Thr Ala Gly
    3215                3220                3225

Glu Ile Pro Leu Thr Pro Ile Gln Arg Asp Tyr Phe Ala Ala Gly
    3230                3235                3240

Pro Leu Ala Pro His His Phe Thr Gln Ser Val Phe Leu Glu Leu
    3245                3250                3255

His Ala Asp Leu Asp Glu Pro Ala Leu Arg His Ala Leu Ala Ala
    3260                3265                3270

Leu Ile Gly His His Asp Ala Leu Arg Thr Arg Phe Val Arg Glu
    3275                3280                3285

Asp Gly Asp Trp Arg Gln Tyr Ala Thr Pro Pro Glu Pro Val Asp
    3290                3295                3300

Ile Leu Arg Arg His Asp Leu Ser Gly Leu Pro Glu Ala Gln Arg
    3305                3310                3315

Ala Ala Ala Met Asp Glu Leu Ala Ala Ser Ala Asp Ala Gly Leu
    3320                3325                3330

Asp Leu Ala Ala Gly Pro Pro Ala Ala Ala Leu Leu Phe Val Phe
    3335                3340                3345

Gly Pro Gly Glu Arg Pro Ala Leu Phe Val Thr Ala His His Leu
    3350                3355                3360

Val Val Asp Gly Val Ser Trp Arg Ile Leu Leu Glu Asp Leu Glu
    3365                3370                3375

Ala Gly Tyr Val Gln Ala Arg Asp Gly Lys Pro Val Ser Leu Gly
    3380                3385                3390

Ala Lys Ser Thr Ser Phe Gly Gln Trp Ala His Arg Leu Ala Arg
    3395                3400                3405

His Ile Ala Asp Gly Gly Leu Ala Glu Gln Ala Ala Tyr Trp Gln
    3410                3415                3420

Ala Leu Pro Asp Gly Thr Glu Val Pro His Asp Gly Ser Gly Pro
    3425                3430                3435
```

Ala Val Val Glu Ser Val Gln Thr Val Thr Val Glu Leu Pro Glu
3440               3445               3450

Asp Thr Ser Glu Val Leu Leu Arg Arg Ser Ala Gly Val Phe Arg
3455               3460               3465

Thr Arg Phe His Glu Val Leu Phe Ala Ala Leu Ala Gly Thr Leu
3470               3475               3480

Ala Arg Trp Thr Gly Glu Arg Gln Val Val Phe Asp Thr Glu Gly
3485               3490               3495

His Gly Arg Glu Asp Leu Phe Asp Asp Val Asp Leu Ser Arg Thr
3500               3505               3510

Val Gly Trp Phe Thr Thr Glu Tyr Pro Val Ala Leu Glu Val Ala
3515               3520               3525

Gly Asp Arg Asp Asp Trp Pro Ala Leu Ile Arg Ser Val Arg Gly
3530               3535               3540

Gln Leu Arg Ser Leu Pro Gly Asn Gly Phe Gly Tyr Gly Ala Leu
3545               3550               3555

Arg His Leu Ser Pro Ala Gly Thr Pro Gly Ala Ala Leu Ala Glu
3560               3565               3570

Arg Ala Pro Ala Gln Val Val Phe Asn Tyr His Gly Gln Ala Asp
3575               3580               3585

Glu Ala Gln Arg Ala Ala Glu Ser Asp Leu Tyr His Ala Phe Gly
3590               3595               3600

Asp Pro Ile Gly Arg Glu Gln Arg Pro Asp Glu Leu Thr Gly His
3605               3610               3615

Pro Val Glu Val Val Gly Ala Val His Ser Gly Arg Leu Arg Phe
3620               3625               3630

Thr Trp Tyr Phe Ser Arg Asn Val His His Arg Ala Thr Ile Asp
3635               3640               3645

Lys Val Ala Glu Asp Phe Ala Asp Ala Leu Arg Ala Ile Ala Arg
3650               3655               3660

His Ile Thr Glu Arg
3665

<210> SEQ ID NO 5
<211> LENGTH: 11007
<212> TYPE: DNA
<213> ORGANISM: Streptomyces hygroscopicus

<400> SEQUENCE: 5
atgaccagct ctgcagcgga ccagcccgac aacccgaaca ccaccacccc ggcgtcgcgt    60
gccgagcgca ccgccgcgct gccggcccat gtgcaggagc tgctgcgcgc ccggctggcc   120
ggccgggccg ccgcgacggg cggcgcggac accatcccgc gcatcgggca cgacggcccc   180
gtcgcgctct cgcccgccca ggaacgcctc tggtacctgc atgagctcga accggagagc   240
aacgagtaca cacccctgcg cgtcctgcgg ctgcgcggcg acctcgaccc cggcgcgctg   300
tccgcggcgc tgagcgagat cgtcgcccgg cacggcgcgc tccgcaccac cttcggctcc   360 cgcgagggc acgccgagca gaccgtgcat ccgcccgtac cgacaccgct gccgctcgtc   420
gacctgtcgg cggcggacga cggcgagcgg gacgacgcgc tcggacccct gctgcagtac   480
gaggcccggc gccccttcga cctgcgccgc ggcccggtgc tgcgggcgca gctgatccgg   540
ctggcggccg acgaccatgt cctcgcgctg gccctgcatc acatcgtcac cgacggctgg   600
tcgatgggcg tgctcaccgg cgagctcacc gcccactacg ccgcgacgct gcgcggtgcg   660

-continued

```
cccgccgtac tgcccgaact tccggtgagc tacctcgatg tcgccgtctg cagcgtgac      720 cagctgagct ccgcgcggct gcgcgagggg ctcgaccact ggcgcgggga gctggccggg      780
ctggtcccgc tcgatctgcc gacgacctgg cagcggccgc cggtccgcac cagcgccgga      840
gcgctgcact ccttcgagat ccccccggcg gtcgccgcac gccttcggga gctgggccgg      900
gaacagggcg ccacgctgtt catggcgctg gtcgccgcgg tccagctgct gctgtcgcgc      960
tggtcggggc agcgggacat cgcggtgggc accgccgcgg ccgggcgcgg ccggaccgag     1020
accgagaatc tgatcggctt cttcgtcaac aatctggtcc tgcgctcccg gatcgatgag     1080
acgcggtcgt tcaccgagct gctgcgggcg gtacgcgcga cggtcctgga cgccttcgcc     1140
cacgaggatg tgccgttcca gcgggtcgtc gaggcgctgc atccggagcg cgacctcagc     1200
cggccgccgc tggccgaggt cgcggtgaat ctgcacaaca ccccgcggac cgacacggag     1260
ctgcccgggc tgcggatcga ggagatgccg ccgccggtgt cgcctccag catggacctc     1320 tcgttcgact tcaccgagcg cgacgaccgg ctcgaagggc acctcaccta caacaccgat     1380
ctgttcgccg cggacgccgc cgcgcggatg gccgcgcagc tggtcaccct gctcgaggac     1440
ctcacccgcc ggcccgcggt cccggtggcc gggctggccg tgctgccggc cgccgagcac     1500
cgtcgggtga ccgaggagtg gccgcactcc gggcccggcc gggagccgcg taccgcaccg     1560
gagttgttcg ccgcgcaggt cgcgcggacc cctgatgcgg atgcgctggt ctccgacgag     1620
gagacgctca gctatgccga gctggacggc cgtatcaacc agtgggcgcg gctgctactg     1680
gcccggggtg ccgggccgga gacgctggtg cggtggcgc tgccccgctc cgcgcagatg     1740
gtcacggcga tcctggcgat ccagaagacc ggtgccgcct atctgccgct ggacccgaag     1800
agccccgcgg aacgcaaccg gctgatgatc gaggacgccc gccgctgct ggtgctgacc     1860 tcggccgggt tcggcgacgg cgcggaactc ggcgcgcccg cactgttcct ggacgacccg     1920 gacaccgcg ccgccgcagg cgagctgtcc gccggcccgc tggcggccgc cgagctgccc     1980
gccccgctgc tgcccggcca cccggcctac gtcatctaca cctccggttc caccggccgc     2040
cccaagggcg tggtggtcac ccacaccggt gtgcacggcc tcgtggcggc gcagtcggcg     2100
cacttccgta ccgggcacgg cgcgcgggtg ctgtcgttcg cctcgctcgg cttcgacgcg     2160
gccttctccg agctgggcat ggcgctgctg tccggcggtg cgctggtcgt cgtcgaccag     2220
gagcggatcc tgcccggaca gccgctggcc gacgtgctgg ccgagcaccg ggtcacccat     2280
gtgacgctgc cgcccagcgc gctgtccgcg ctgaccccgg ggacgctgcc gaaggacctc     2340
accctggtcg tggccggcga ggcctgcccg ccgcggtgg cccgcacctg gtccgcccat     2400
caccgcatga tcaacgccta cggccccacc gagtccacgg tctgcgccag catgagcgcc     2460
gcgctgaccc cggacaccgt cagcggcgac tcggtcccca tcggccgccc gctctccggc     2520
gtccgggtca gcgtcctgga cgaccggctg cgcccggtgc cggccggcgt cccggcgag     2580 gtgtatctct ccgcgccgc gctggcccgc ggctacctcg gcggctcgc gctgaccgcg     2640 gagcggttcg tcgccgaccc gtacggtccg ccgggaagcc ggatgtaccg caccggcgac     2700
cgcgcccgct ggctggccgg cggcgacctg gactacctgg gccgcaccga cgaccaggtc     2760
aaactgcgcg gcttccggat cgagctcggc gaggtcgagg ccgtactgtc gcgccacgac     2820
ggggtcggcg cggtggccgc cacggtgcac aaggacgagc ggggcacccg ccgcctggtg     2880
gcgtacgtcg tcccggcgcg ggaggacgcg gccgacccg cgcggctgcg cgagttcgcc     2940
cgcgaggtgc tgcccgagca catggtgccc tcggtcttcg tgccgctgga ccggctgccg     3000
ctgaacgcca acggcaaggt cgaccggcgg gcgctgcccg cacccgacat ccggcgcgac     3060
```

```
gagggcagcg cccgtatcgc gccgcgcacc ccggcggagg agacgctggc gcgcatctgg    3120
tcggaggtgc tgggcgtcac ggacatcggc gtcgaggaca acttcttcga cctcggcggc    3180
gactccatcc tcagccttca ggtggtggcg cgggcccggg ccgccggact gcggctgacc    3240
gccaagcaga ccttcctgcg gcagaccatc gccgatctcg ccgccgacgc cgtcgccgag    3300
accgaccccg ccgcgcacgg tgcggccaac gacggcccgg tcaccggcga gctgccgctc    3360
accccatcc agcactggtt cttcaactcc ctcggcgaca gcctggagca gttcaaccag    3420
tcgctgtatc tggagctggc cgagggcccc gacctcccgg cgctgcgcgc cgcactggcc    3480
gcgctgaccg aacagcacga cgcactgcgg ctccgcgccg tatccgagga cgggcagtgg    3540
cggctgcacc acgcgcccgc cgagaccggt caactcctcg aacacctcga tctgtccggc    3600
gtctcgcccg acgagcagga cgccgcgatg gcggccgccg tcgacgcggc gcagcgggac    3660
ttccggctgt ccgaggggcc gctgctgcgg gccggctgt tcaccctcgg cgacgcccgg    3720
ccgcccggc tgtacctcgt cgcgcaccac ctcgtcatcg acggcatgtc ctggcgcatc    3780
ctgctggcgg acctgagac cggctaccgc ctggcggcgg acggccggcc gatcgacctg    3840
gggccccgga ccacctcgtt ccgcgactgg tcgcgccggc tgtcgcgcca tgtcgcggac    3900
ggcggcctgg acgccgaact gccgtactgg aagggcgtac aggacgcggc gcgcgagacc    3960
gccccgctcc ccgtcgacac cggcgggctc ccgaccgcc agggcgccca ggaggagccc    4020
ggcgagaaca ccgccgggtc ggcccgcacc gtctccgtac agctgtccgc gcgggcacc    4080
gaggcgctgc tgcggcaggt gcccgaggcc taccgcaccc agatcaacga cgtcctgctc    4140
agcgcgctgg ccgggtgct gaccgactgg gcgggcggcg agcgggtgct gatcgccctg    4200
gagggccacg ccgcgagga gctcttcgac gaggtggacc tcacccgcac cgtcggctgg    4260
ttcaccaccc tcttcccggt cgccctgcgg atgccggccg accgggactg gggaacggtc    4320
ctcaagagcg tcaaggaaca gctgcgggcg gtgccccaca acggactcgg ccatggcgcg    4380
ctgcgtcatc tggcagggcc caactcccct ctggaggacg gtccggagcc cgaggtcagc    4440
ttcaactacc tcggccagct ggacgtgtcc gccgaccgca ccggcctcgc ccgcgccatg    4500
ctcaccagcg agggcgccga gcgggccgcc ggccagcacc gtgcgcagct gctggagatc    4560
aacggcgtgg tcaccggcgg ccggctggag ttccactgga cgtactcggt gaaccggcac    4620
cgcgcagaga ccgtcgaacg gctcgccgcg ggcttcatga ccgcgctgga agcgatcgtg    4680
gcgcactgcg ccgcccccgg ttccggcggc gccaccccgt ccgacttccc gctggccgcc    4740
ctcgaccagg ccaccgtcga caagatcgcc ggcgacggcc gcacggtcga ggacatctac    4800
ccgctcaccg cgatgcagag cggcatgctc ttccacgcgc tgagcgagtc cggacgcgac    4860
ccgtacaccg ggcacttcgg cgtccgcgtg gacggcatca ccgacccggg ggcactggcc    4920
gcggcctggc agcaggtcgt cgaccggacc ccgccctgc gcaccgccat cgtctggcag    4980
gacgtcgcgg aacccccttca ggtggtgcac gcggccgccc gtgtgccggt cacccatcac    5040
gacctgcggt ccctgaccga gcaggaacgg caggccgccc tggaccggct gtgggagcgg    5100
cgcgaggaga ccgtcatcga tctcgccgtc gcgcccgcgc tgcggctgac cctcgtccgg    5160
ctcaccgaca cgccgtcca gatgttctgg acctcgcacc acatcctgat ggacggctgg    5220
agcttcgccg ggctgctgtc ggaggtgtgc gcccagtaca ccgcgctgac cggcggcccc    5280
cgcgtggcgg ccccggcccg ccgccgtac cgcgactatg tcggctggct ggccgaacag    5340
gaccagccgg ccgccgaggc gcactggcgc tcggtggtcg acgggttcac ggtgccgacg    5400
```

-continued

```
ccgctgccct acgaccggca gccggtgaag gcacacggca cccggtcctc gcgtgaggtg    5460
cggctgcagc tgtccgccga gcgctccggg cggctgtccg aggccgcccg gtcggcgcgg    5520
ctgaccgtca acacgctggt gcagggcgcc tgggcgatcc tgctggcgcg ctacggcggg    5580
gtgcgcgacg tctgcttcgg caccaccgtc tccggccgtc ccgccaccct gcccggcgcc    5640
gagtcgatgg ccgggctgtt catcaacacc gtgccggtac gggcgaccat cgacggtgcc    5700
ggtgccggcg acggcgccgc caccggcacc gtcgagtggc tgcggcggct gcagagcgag    5760
cagctcgact cccggcagca cgagcatgtc tcgctggcgc agatccagcg ctggagcggc    5820
gtaccggccg gcaccaacct cttcgacagc atcgtcgtct tcgagaacta ccctacgac    5880 agcgatgcgg ccgccaagta cgggctgacc ctcggcacgt tccagggcga cgaggtcacc    5940
aactacgccc tcaccctgac cgcgtacgtg gccgacgagc tgcatctcaa cctcggctac    6000
gacccggatc tgttcgacga ggcgaccgtc gagcggatgg ccgggcatct ggcgacgctg    6060
ctcgacgccg tcgccgccgc cccgcacacc cggtgacg acctcccgct gctcgatgcg    6120
gccgaacacc accggcttct caccgagtgg aacgacaccg ccgccggctt ccgccgccg    6180 cggccggtcc atgagctctt cgccgagcgg ccgcccgta ccccggacgc ggtggcggtc    6240
agcgacgcca cccggcagct gaccttcgcc gagctggaga cccgcgccaa ccaactggcg    6300
caccacctgg ccggtctggg cgtggcgccc ggcacgctgg tcggggtgtg cgccgaccgc    6360
ggggtggacg ccgtggtggc gctgctgggc gtgctgcggg ccggcggtgc cttcgtaccg    6420
ctggaccccg cctatccggc ggagcggctc caggtcatgc tggaggacgc cgcggtgccg    6480
gtcgtggtga ccgaggagcg gctgctggac cggaccgccg ggcacgacgc gacgacggtg    6540
tgcctggacc gcgatctgcc gctgctggag gagctgccgg cccgcccgcc gtacaccgcc    6600
gtggcaccgg acgacctggc gtatgtcgtc tatacgtcgg gcaccaccgg cgcccccaag    6660
ggcgtgatgg tcgagcaccg gcacgtccac cacatggtgc acgcctggga ccggcgctac    6720
gggctcgccg cgctgcaacc gcgcgcgctg tccgtctcca gcatctccgt cgacctgttc    6780
ttcagcgact tcctgctctc cgccctcttc ggcggcacga tggtgatctg tccgcaggac    6840
gccgtcgccg accaggtggc gctgaccgat ctgctgctca gagccgggc ccagctgatg    6900 gtgacggtgc cgacgctggc ccgcgcggtg gtcgccgagc tcgcctggcg cggtgtgaca    6960
ccggaggcgc tgcgggtgct gatggtgggc tccgagggct ggccggccga tgccgcggcc    7020
gagatcctgg ccggtctcgc gccgggcacg gtgctggtca acgcgtacgg atcgaccgag    7080
accacggtcg actccacggt cttccagctc ggccgcgacc cgctgggcga cgccgccttc    7140
gtaccggtcg gcaggccgct cgccaacacc cggatctatg tgctggacga gcggatgcgc    7200
ccggttccca ccggcgtcgt cggcgagtgc tacatcggcg gcgacggagt gtcgcgcggc    7260
tatctgggcc gcccggagct gaccgccgag cgtttcctcg acgaccgtt cgcgccggag    7320 ccgggcgccc ggatgtaccg gaccggtgac ctcgcgcgct ggcgggccga cggcaacctc    7380
gaatgcctcg gccgggtcga cgaccaggtc aagatccgcg gcttccgggt ggaactcggc    7440
gaggtggagg ccgcgttggc ccgccacccg gcgatcgact cggcggccgc cgcgatccgc    7500
aaggacgacg gtgggccggc ccgtctggtg ggctatgtcg tgcccgccgc cggccacacc    7560
cccgacctgg ccgagctacg ggccttcgcc ccgaacggc tgccgtcgcc cgccgtcccc    7620
accgcgtaca tggtgctgga cgcgctgccg atgacgccga gcggcaccgt cgcccggcgt    7680
gcgctgccgg cccggccgg ggcgcaggac ccgcccggc cctacaccgc gccgggcagc    7740
gccaccgagc tgctgctctg cggtatctgg caggaggtcc tgggcgtcga acgggtcggc    7800
```

```
gtgcacgaca acttcttcga cctgggcggc gactcgatcc tcagcatccg ggtcatctcc      7860
cggatccggg ccacgctggg cgtcgccccg tcgccccgcc agctcttcga caccccgacg      7920
gtggccggtc tcgccgccac cctcggccgg gacgacccct cggcgccgc cgacgtcccc       7980 ctggagccgg ccgaccgcgg cgcaccgctg ccgctgtcgt ccgcccagca acgccagtgg      8040
ttcctgcaca acttcgaccc ggacagcagc gagtaccaca tcgtcaccgg gctccggctc      8100
gacggtgatc tggacgtcgc ggcgctgcga ggggccctga acgggctcgt cgcccggcac      8160
gaggcgctgc gtaccaccta cgcggccacc ggcgagggcg ccgagcagat cgtgcacccc      8220
gcgggcgagg tggtctgcga gcgtacggat ctgtccgagg tgcccgagga ccagcgcgag      8280
gacaccctgc gcgggcacat cgaccgcgcc gccgcccggc cgttcggcct caccgagggc      8340
ccggtcctgc gcgccgaact gttccggctc ggcgcccgtg accatctgct gctgctcgtc      8400
atccaccaca tcgccaccga cggtgtctcg atgcaggtgc tcaccgagga gctcggcgtc      8460
cactacgccg cggcgctcga cggcacaccg cccgccctgc cggcgctgcc ggtctcctac      8520
gccgactacg cggcctggca cgcgcggatg ctgtccggcc cggcgctgga cggccatctc      8580
gcctactggc aggagcggct ggccggtgtc cggccgctgg agctgccac cgaccggccc       8640 cggccgcgg tccgcagctc cgcgggccgg atgctgctga tcgagatcga ccgcgggtg       8700 gccgcgggcc tcaaggaact ggcccgccgc catgacgcca ccctgttcat ggcgctcacc      8760
gcggcggtcc agctgctgct ggcccgctac accggacagc cggacatcgt cgtgggcacc      8820
ccggccgccg gccggggccg gcaagaactc gaggggctcg tcgggctgtt cgtcaacacg      8880
gtggcgctgc ggtccaccgt cgacgagagc gggaccttcg acgccttcct cggtgcggtg      8940
cgcgacaccg tcctcgaagc gtttgtgcac gaggacgtgc cgttcgaccg gctggtcgag      9000
gtgctgcgac cgcgccgcga ccccagccgt aacgcactgg tggaggtgtt cgtcggactg      9060
gagacggacc ggtcggcgcc gccggcgctg cccggactga cggtgaccga ggtcccgttc      9120
gtcagcggcg aggtcagcca tgacctcagc ttcgacttcg tcgacgggcc cgacggcctg      9180
aaggcggcca tcggctacag caccgcgctg ttcgacgacg gcaccgtcga gcggatggcc      9240
ggccagttcc aggcgctgct cgccgcggtc ctggaggacc atcgcgcgct cgccgacatc      9300 gcacccgcg acgaggccga ggtgcggcgg ctcgccgaac tgcggcaggc cgcgccctcg       9360
gagcccgacg cgtcggaaac cgacggcgcg ccggccgcct accgcgcgcc cgggaccgct      9420
gccgagcggg ccctggcgga gatctgggcc gccgtgctgg gggtgccgcg ggtcgggacc      9480
gacgacaact tcttccagct gggcggcgac tccctgctca gcatccaggc ggtgcagcgg      9540
atgcggcagg ccggcctggc ggtgaccacc aaggatctgt tcgtccacca gagcatcgcc      9600
ccgctggcgg ccctcgccga ggaacgggcg gcggaccggc cggaggcccc ccaggcgcag      9660
cacgacgatg ccgggacggc gggcgagata ccgctcaccc cgatccagcg cgactacttc      9720
gcggccgggc cgctcgcccc gcaccacttc acccagtcgg tgttcctcga actgcacgcc      9780
gatctcgacg agccggcgct gcggcacgca ctggccgcgc tgatcggcca ccacgacgcc      9840
ctgcggaccc gcttcgtacg cgaagacggc gactggcggc agtacgccac cccgccggag      9900
ccggtggaca tcctgcgccg gcacgacctg tccgggctgc cggaggctca acgggccgcc      9960
gccatggacg agttggcggc ctcggccgac gccgggctcg atctggcggc cgggccgccg      10020
gccgcggcgc tgctgttcgt cttcgggccc ggggagcggc cggcgctgtt cgtgaccgcg      10080
caccatctcg tcgtcgacgg cgtctcctgg cggatcctgc tggaggacct ggaagccggc      10140
```

```
tacgtccagg cccgcgacgg gaagccggtg tccctgggcg ccaaaagcac ctcgttcggg    10200
cagtgggcgc accggctcgc ccggcacatc gccgacggcg gcctcgccga gcaggccgcc    10260
tactggcagg cgctgcccga cggcaccgag gtcccgcacg acggctcggg gcccgcggtg    10320
gtggagtccg tgcagaccgt cacggtggag ctgccggagg acaccagcga ggtgctgctg    10380
cgccggtccg ccggggtctt ccggacccgc ttccacgagg tgctgttcgc cgcgctcgcc    10440
ggcaccctgg cccggtggac gggcgaacgc caggtcgtgt tcgacaccga gggccacggc    10500
cgggaggacc tcttcgacga cgtcgatctc tcccggaccg tcggctggtt caccaccgag    10560 tacccgtcg cccttgaggt ggccggcgac cgggacgact ggccggcgct catcaggtcg    10620
gtacgcggac agctgcggtc gctgcccggc aacggcttcg gttacggcgc gctgcggcat    10680
ctgagcccgg ccggcacccc gggtgccgca ctcgccgaac gggccccggc ccaggtggtg    10740
ttcaactacc acggccaggc cgacgaggcg cagcgcgcgg cggagagcga cctctaccac    10800
gcgttcggcg acccgatcgg ccgggagcag cggcccgacg agctgaccgg gcacccggtg    10860
gaggtggtgg gcgccgtgca ctcccgggcgg ctccgcttca cctggtactt ctcgcgcaat    10920
gttcatcaca gggccaccat cgacaaggtg gccgaggact tcgccgacgc gctgcgcgcc    10980
atcgcccggc acatcacgga gcggtga                                        11007
```

<210> SEQ ID NO 6
<211> LENGTH: 972
<212> TYPE: DNA
<213> ORGANISM: Streptomyces hygroscopicus

<400> SEQUENCE: 6

```
atgtccgcca cgccgcgccc gcgacccgtt ctacggccgt tccgcccgg agacggccgc      60 tcgctgctgg cggcctggtg ccgcagcgcc ccggacgatc cgatcaccgc cgcccgcttc    120
cggacgctga tcctgctcga ccccaatttc gacccagagg ggttacgggt ggccgatctc    180
gacgggcagg tggtgggcgc cgtctacgcc gtgcgccgcc gtaccccgct ggccggcacc    240
gacctggagc cggacgtcgg ctggatcctg ttcttcttcg tcgatccgcc gcaccgccgt    300
acgggcctcg gccgccggct gctcaccgat gcccctcgact ggctgcgcgg acacggccgc    360
acccgggtcg acttcgcccc gtacgcccccc cactacgtgc tccccggcct ggaccgggcc    420
gcgtacccgg aggccgcccg gctgctggcg agcctcggct tccgtccccg ctacgaggcc    480
gcggcgatgg accgcggcct ggtcggctac cgcatgccgg acgaggtacg gcggcacgag    540
gcggccctga cggcgcgcgg ccaccgattc ggcaccccgt ccgacgacga tctggtggac    600
ctgctcgggc tggccgagga gttcaccccc gactgggcgc gggcgatccg gcagtgcctg    660 accgcggcg cccctctgga ccgcatcgtc agcgcccgcg cacccgacgg gcggatggcg    720
ggctgggcca tgcacggcgc gtacgacggt acggccgagc ggttcggccc cttcggcgta    780
cggaaggagc tgcgcggcgc cggtctgggc aaggtgctgc tgcatctgac gctggagcgg    840
atgcgggcgc tcggcgtgca cggggcgtgg ttcctgtgga cgggcgagca gagcccggcg    900
gggcatctct accgcgcgag cggattcacc acgacccgga ggttcacggt gctgcggtgg    960
gaggcgggat ga                                                        972
```

<210> SEQ ID NO 7
<211> LENGTH: 1416
<212> TYPE: DNA
<213> ORGANISM: Streptomyces hygroscopicus

<400> SEQUENCE: 7

```
atgaggcgcc gtacattcac ggccggggcc gcggcgggg ccgccctgtt ggccggggcc      60
ggatgcgacg cgcccggtgg cgccgggcac ggagacggag agcacggaga cggagacggc     120
ggtgacggcc ggggcagcgg cggccgtcgc ggcgcccccg tcaccctgac cgtcctcacg     180
cactacgcga gcgaaccgct cgcctcggcg ctgcaaaccg tcgtcgacgc ctggaacgcg     240
acgcaccggc gcatcacggt gcgcacggcc gcggtcaagt tccccgatct gctgacgact     300
tacatggtgc ggcaggccgc gggccagggc gccgacatca tccatccgta ctgcctgtgg     360
accggccagc tggtgcgggc cggagtactg cgcccggtgc cgcccacggc cacgcggcag     420
atccgccggg acttcacccc ggcggccgtg gcggcgtcgt ccgtgcacgg cacgctctac     480
ggctacccca cggaggtgca gacctacgcg ctctactaca caagcggct gctgcggcag      540
gccggtatcg acggaccgcc gggtacctgg caggagctgg aggacgcggc gtaccgcacc     600
gcccgccgcg accgccacgg caacatgctg gtgcagggct cgggctgtc acgggccgac      660
gatgcgagcg tcgtggggca gacgctggcc ctgctggccg cgcgcggcgg cacattcctc     720
acctccgacg gacggcggac cgccatcggc tcggcggccg ggcgggatgt gctcgacctg     780
gagcgccggc tcatcgaccg cggcgccgcc gactccggta tctcgctcct gagggccttt     840
ccgtccggcc aggtggcgat ggcgatcaac gccggctggt ggacggcgag tctgcgcggc     900
gcgatggggg cggactaccg cgaggtcggg gtggcgccgg tgccggggcc cgcaccggac     960
gaccgcggca cgctcgccac gggcttcctg ctcggcgtga acgcgaagag cagatatccg    1020
ggggaggcct gggagttcct gcactggctc aacggtgtgc gggcgccggc cgcccggccg    1080
gggcgcagcg cgggaggagg cgtcccggtg tccaggatga gcgcgctcca ggtgtcggtc    1140
ggttcgatga ccgggcgggc ggacgatatg cgggcgctgc tggaggcga cggcgagagg     1200
gacgccgacg gccgtggtgg cggcgaccgg aacctcggcc ccttcctgga cgcgctgcgc    1260
tacgccgtcc cggaaccgaa cggtccgcgc gcgcagcagg ccaaatcgct gctgcgcaag    1320
aacatcgagg acgtctggac gggccgggcc tcggtcgatg ccgcgctgcg caccgccggc    1380
cggcagatcg accaggaact gtcccggccc tactga                             1416
```

<210> SEQ ID NO 8
<211> LENGTH: 912
<212> TYPE: DNA
<213> ORGANISM: Streptomyces hygroscopicus

<400> SEQUENCE: 8

```
atggcttcag ccggcggtgg tcccgtcagg gcggcccggc ggcggcagac cgccgtcgcc      60
tatctgttcc tgaccccggc cctgctgttc ttcgcggtct tcctcgccct gccgctgctg     120
ttcgccgtgc tgctcgcgca gtcgcgctgg gccggcttcg acctcgccga tatcgagccg     180
gtcgggatgg ccaacttcac cgacctcttc gcccgcggct cgaccttcct gacgccgtc      240
ctcaccaata cgctgctgta cgccgtcggc accgtcgcga tcgccctcat cggcgcgctc     300
accctcgcga cctgcatcga caaccttcgt ttccaggggc tttggcggac cctctatttc    360
ctcccgatcg tgacgaccgt ggtcgccgtc ggcaacgtat ggaagtacat gtacgcaccg    420
ggcgggctga tcaacggagt gctcaacggt ctgggtctgc attccgtggc ctttctccag    480
gaccccggca cggcgctgcc gtccgtcgtc gtggtgcagg catgggcctc catgggaacc    540
gcgatcctga ttctcaccgc gggcctgaag tcgatccccg aggcctatta cgaggccgcc    600
gagctggacg gtgccggcgc cggcaccgtt ttccggcgca tcaccctgcc gctgctccgg    660
```

-continued

| | |
|---|---|
| ccgtccctgc tcttcgtctg catcacccaa ttcatcaccg gattacagtc gttcgccctg | 720 |
| atcaatgtca tgacggacga cggcggaccg ggcgatgcga cgaatgtcgc ggccctggag | 780 |
| atgtatcagc aggcgttcag gtacggcgac tggggaatcg ccagtgccgc cgcctttgtg | 840 |
| ctgttcctgg tcattgtcgc gatcacggtg gggcagctct ggctgttccg ccggaaaggc | 900 |
| ggggaatcgt ga | 912 |

<210> SEQ ID NO 9
<211> LENGTH: 891
<212> TYPE: DNA
<213> ORGANISM: Streptomyces hygroscopicus

<400> SEQUENCE: 9

| | |
|---|---|
| gtgagccggt ccgctcgtcg gcgcccgggc cgtcgccgcc cctggggctc gtacgccgtg | 60 |
| gtcgtcgccg gggccgccct caccctcgtc ccgttcctcg acatgctgct gacctcgttc | 120 |
| aaggggcccg gcgaatacgg gaaactcccc taccgattcc tcccccaggc gttcgacctt | 180 |
| tccaactacc gtgccgcgat ggagcagctg gatctgcccc tgcttttccg caacagcgtc | 240 |
| atcgccaccg ccgtcatcac cggatccatc ctggtgacct ccgcgctcgc cggatacgcg | 300 |
| ctggccaagc tgcgcttccc cggccgggag gtgatcttcc gcctggtcct gtccacgatg | 360 |
| atgttcccgc cgttcctctt cttcatcccg cactttctga tcctggtgca ctggcccggc | 420 |
| gccggcggca acgacctgct gggccgcggc ggggcgggcc tcaccgtgag ccttgcggcg | 480 |
| ctggtcatgc cgttcctcgt atccggttc gggatctttc tgatgcggca attcatggtc | 540 |
| tccatcccgg acgaactgct ggaggcggcc cgtatcgacg gcgccggcga attcgccctc | 600 |
| tggtggcgca tcgtgctgcc ccagacgaaa ccggtggcgg tcaccctcgc gctgctcacc | 660 |
| ttcgtcaacg cctggaacga atacatctgg gcgctgctga tctccaccgc caatccgcgg | 720 |
| ctgatgacgc tgccggtggg catccagatg ctgcagagct atctcgaccc cgaccgtatg | 780 |
| gtcccggtca tgatggccgg cctggtgctg agcatcctgc cggtcctgct gctcttcctg | 840 |
| ctgctccaga agcactacct gcgcggggtg atgctcagcg cctcaagtg a | 891 |

<210> SEQ ID NO 10
<211> LENGTH: 1278
<212> TYPE: DNA
<213> ORGANISM: Streptomyces hygroscopicus

<400> SEQUENCE: 10

| | |
|---|---|
| atgagttccg gttctcctg ggctgttgtg gcaactgtgg tgagagtttc tgacccctca | 60 |
| ggaggaacca tggcttccga ctcgtcgtcc ccgacgccga tgccggccgt gtcgttgatc | 120 |
| gtgccgacgt tcaacgaggc agcgaacatt gatgagttgc tcgacggcgt gtgtgcggcg | 180 |
| atcccggcgg gtctggaggt cgaggtgctg ttcgtcgacg actcgacgga tgacacaccg | 240 |
| gaagtcatcg agaaggcggc cgcgcgctgt ccgatgccgg tgtcggtgct gcaccgggag | 300 |
| gttcccgaag gggggctcgg cggagcggtg gtggccggga tcgcccgtac gagtgcgccg | 360 |
| tggatcatgt tgatggacgc cgatctgcag catccgccgg agctgctgcc gcagttgatc | 420 |
| gaggctggtg agcgcgcggc ggccgagttg gtggtggcca gcagatacgc ggagggcggg | 480 |
| agccgtggcg ggctggccgg cgggtaccgg gtggccgtgt cggggcgtc gaccgcgctg | 540 |
| accaagtcgc tgttccccg gctgctgcgc ggggtctccg acccgatgag cgggtgcttc | 600 |
| gccatccggc gggaggcggt cgaccgcgcc gtacaggagg gcgagacccg gcaggaaggg | 660 |
| gggctgcggc cgctcggcta caagattctg ctggagctcg cggtgcgctg ccggccgcgc | 720 |

```
gggtggtgg    aggtgccgta    cgagttcggg    gagcggttcg    ccggcgagtc    gaagtcgacg      780
gtgcgcgagg    ggctgcggtt    cctgcggcat    ctggcggagc    tgcggaccag    cgacaagcgg      840
gcccggatgt    tggccttcgg    gctgatcggg    gtgtcgggct    tcgtaccgaa    tctgctggcg      900
ctgtgggcgc    tgaccggtgc    cacgaccctg    cattacgcgg    tggcggaggt    gctggccaat      960
cagctcgggg    tgctgtggaa    cttcgccctg    ctggacttcc    tggtctaccg    gagcgggaaa     1020
ccggggcgcg    gggccggccg    gctgctgggg    ttcgcggcgc    tcagcaacgc    ggatctgctg     1080
gcgcggatcc    cgttgatgat    gctgttcgtg    gagcaggccg    gatgggggcc    ggtgccggcg     1140
accgtgatca    gtctcgtggt    ggtgttcgcg    ctgcggttcc    tgctggtcga    cacgttgatc     1200
taccggcgca    aggggcggc     tgccaagcgc    gcggcggacg    cggcggtcac    cggcgggcag     1260
ggcgagcgcg    ctgcttag                                                               1278

<210> SEQ ID NO 11
<211> LENGTH: 1413
<212> TYPE: DNA
<213> ORGANISM: Streptomyces hygroscopicus

<400> SEQUENCE: 11
gtgaccgtcg    tgctgctcgc    cctgtccgac    aggtacggct    acaacgtcga    cgagctgtat       60
ttccggctgc    tcggcgaaca    cggctgggcc    tgggctaca    ccgaccagcc    gccgctggtg      120
ccggcgctgg    tgcacgccac    cgcccaggtc    ctcggcgact    cggtgtgggc    gatccgggtg      180
ccggcggcgc    tgtgcgcagg    ggccgtggtg    ctgctcgggg    cgctgatcac    cgccgaactc      240
ggcggcaccc    gccgggcaca    gactctttcc    gccctgggtc    tgggcagctc    gttcctggtg      300
ctcagcgtcg    gccacatcat    ggtgaccacc    accctggaca    tgctcgcctg    ggccgcggtg      360
ctgctcttcg    tcctgcgggc    gctgctgcgc    tcggagggca    agtggtggct    gtgggcgggg      420
gtggtgctgg    gcctggcgct    gtacgccaag    tacatcgtgg    cgctgctgcc    ggtggcgctg      480
ctggccgggc    tcgcgctggt    cggtccgcgg    aaggtgttcc    gtgaccggtg    gctgtacgcg      540
gggatcgcgt    tggcgctggc    catcggctcg    ccgaacctga    tctaccaggc    cacccatgac      600
ttcccgcagc    tgcagatggc    cgatgcgctg    ggtgccaccg    acggcccgat    gaaccgggtc      660
atcttcgtgc    cgagcctggt    gatcctgctc    ggtccggtgc    tgaccgtggt    gtgggtcgcg      720
gggctggtga    gctgctgcg    tgacccggca    tggcggccgg    tgcgggcgct    ggcaccggcg      780
ttcgtggtcg    gggtggcgct    gaccctctac    ggcggtggcc    ggcccgacta    cgtcggcggg      840
ttcctgatcg    ggctgttcgc    ggccggggcg    gtggccgccg    accggtggat    ggggcggcgt      900 acgtccggc     gggtgctgct    gtgcgccgga    ctggccgcca    gtgcggtgct    ccaggtgctg      960
atggcgctgc    cggtgctgcc    gcagagctcc    ccgttcgtgc    cgctgaacaa    catctccctg     1020
gagagcgtcg    gctggccgcg    gctcgccgag    caggtgcgca    cggcgtacga    ggcgctgccg     1080
cggcagcagc    gggagcgggc    cgtggtgctc    gccgacaacc    tcggggagat    cggcgcgctg     1140
gaccgctacg    ggcacgggct    gcccgcggtg    ttcagcggcc    acaacgaact    gcacaagtgg     1200
ggcccgccgc    cggagcgcgc    cgatgtggtg    gtcgcggtgg    gcgtgccccg    gtcccggctg     1260
gccgcggggt    tcacctcgtg    caccgtcgtg    ggacgggtcg    acaacggcgt    cggcgtcgag     1320
aacgccgagc    agggcagacc    gatcacggtg    tgccacggcc    gcaaggcttc    ctgggcccga     1380
ctgtggccct    cctaccacta    cttgagcggc    tga                                       1413

<210> SEQ ID NO 12
```

```
<211> LENGTH: 1530
<212> TYPE: DNA
<213> ORGANISM: Streptomyces hygroscopicus

<400> SEQUENCE: 12
atgacgacat ccctcgacag ggattccagg gcggccgcgg ccgggccggg ggtgttccgc      60
ccggcgccga tggcgtggcg gccggtcgcc gtggtggtgg ccgcgctggc cgtgctgttg     120
ttcgccttcg ccggcgaata cggctaccac gccgacgagt tgtacttccg gctgctcggg     180
gtgcacggct tcgcctgggg ctatgtggac cagccgccgc tgctgccact ggccgtacgg     240
acctcgatgg agatcttcgg cgacagcatg tgggcgatcc gggtgccgcc cgtgctgtgc     300
gcggcggccg tgaccgcgct cggcgcgatg atcgccgccg agctgggcgg ttcccggcgg     360
gcccagacgc tgaccgcgtt cggggtggcc acctcgacga tggtgctcag cttcggccac     420
tggatcctca ccaccagctt cgacaccgtg gcgtgggccg cggtgctgct gttcgtgatg     480
cgggtgctgc tgcgcggcga gagcaagtgg tggctgtggg ccggggtggt ggtcggtgtc     540
gcgctgtacg ccaagtacat cgtgctgctg ctgccggtgg cgctgctggt ggggctggcg     600
ctggtcggtc cgcggaaggt cttccgcgac gggaagctgt acgcgggcac ggcgctggcg     660
ctggtcatcg gctcgccgaa cctgatctac caggccaccc atgacttccc gcagctgcag     720
atggcggagg ggctggcggg caccgacggc gaggcgaacc gcgccatgtt cgccacgaac     780
ctgatcctgc tgttcggccc cgcgctgttc gtgctgtgca tgatcgggct ggtcaagctg     840
ttccgggtgc cggagtggaa gcccgtacgg acactggccg tcggctatct cgcggccacc     900
gcggcgtcgt acctcatcga gggcggccgg ccggactaca ccggcggact gctgatcgcg     960
ctgctggccg ccgggtgtgt gacggccgac cggtgggcgg cgcccgcaa gctgcggctc    1020 tcggtgctcg cggtctcgct gacgctcagc accgcggtgc agatgctgct gtcgctgccg    1080
gtgatcccca gagctcgct gcgcgacttc cagatcgcca gcatggcgct ggagacggtg    1140
ggctggcccc gtctggtcca gcagaccgag gcggcctacc gcgcactgcc ggccgcggac    1200
cgcgaccgcg cgatcgtgct caccgagaac ttcggcgagg cgggcgccct ggaccactac    1260
gggcacgggc tgccgaaggt gtacagcggc cacaacgagc tgtaccactg ggcccgccg    1320 ccgcagcgcg ccgaggtggt ggtcgcggtg ggcatcgacc ggaaccggct gtccgccgac    1380
ttcaccagct gcaaggtcgt cgaccacatc gacaaccgcc tgggcatcga caatccggaa    1440
cagggcgtgc cgatcacggt gtgccacggc cccaagaagc cctggtccgc gctgtggccg    1500
acctaccggc actacaacgc ctatctgtag                                     1530

<210> SEQ ID NO 13
<211> LENGTH: 1014
<212> TYPE: DNA
<213> ORGANISM: Streptomyces hygroscopicus

<400> SEQUENCE: 13
atgagtaccg aggtttccga ggcgcaggcg cgacgcgccg tggcagacat cttcaactcg      60
acgctggctt cttcggccat cggcgccgcg tgggagctcg agctcttga cgagctgcgg     120 gagaacggca agttggatgt ctccgatttc gccgtacgcc atgatctgca cgagccggcg     180
gtggtcggca tgttcaccgc gctggcgagt gtgggaatcg tgcggcgcga gggcgccacc     240
gtcgtcgtcg gcccgtactt cgacgaggcc aatcaccacc gttcactgtt ccactggctc     300
aatcagggca gcgcgagct cttccgccgc atgccgcagg tgctgccgaa cgagaaccgc     360
acaggaaagt tctaccagcg ggacgcgggg gcgatcagct acgcgtgccg cgagatcagc     420
```

```
gagcgctatt tcgacccggc gttctgggcc gcggtcgacg gtctgggtta caccccacc    480 accgtcgccg acctggggtc cggcagcggt gagcggctga tccagatcgc ccggcggttc    540
cccggcgtcc gcggcctcgg cgtggacatc gccgacggcg cgatcgccat ggcggagaag    600
gaggtggccg ccaagggatt cggcgaccag atctccttcg tgcggggcga cgcgcgcacc    660
atcgaccagg tctcggcgcg cggggaattc gccgaggtcg atctgctcac ctgcttcatg    720
atggggcacg acttctggcc ccgcgagaac tgtgtgcaga cgctgcgaaa gctgcgcgcg    780
gcattcccga atgtgcgccg gttcctgctc ggcgacgcca cccgcaccgt cggtatcccc    840
gaccgcgaac tccccgtatt caccctggga ttcgagttcg ggcacgacat gatgggcgtt    900
tacctgccga ccctcgatga atgggacggg gtattcgaag agggtggctg cgctgtgtg    960 aagaagcacg ccatcgactc gctgtcggtc tccgtggtct tcgaactcga gtaa         1014

<210> SEQ ID NO 14
<211> LENGTH: 1320
<212> TYPE: DNA
<213> ORGANISM: Streptomyces hygroscopicus

<400> SEQUENCE: 14
atggaccacg aaagcctgca cagcaccctg accgaactgg cggcccgcca tcgggtgccc     60
ggcgcgcagc tcgccgtcat ccacgagggg gaacggttcc tggtgcacac cggagtgtgt    120
gacaccgcct ccggagcccc cgtggagcgg cacaccgcct tccccgtcgg ctcgctgacc    180
aagccgttca ccgccgccct cgcgatgatc ctggtggccg acggggacgt ggacctggac    240
gagccgctga gggggcagct gccggagttc ggggcgggcg aactcgtcac cctccggcag    300
ttgctcagcc acacctcggg cctgccctcc gatgtgccgg agggcagcga cgaggccggc    360
ggcggcgacc gtgcccgctg ggtggcccgg tactgccgta cggcggatct cacgcatgcg    420
cccgggacgg tcttctcgta ctccaacatc ggctatgtcg tcgtgggccg gctcatcgag    480
gcggtcaccg gcatgagctg gcaggaggcg atcagcgcga tcctgctcga accctgggc    540 acccggcccg cgttcgtcgt cggagccccc gccaccgtc cggtggccac cgggcacgcc    600
gtccaggcgg tccgcgaccg ggtggtgccg ataccggacc aggatcttcc cgaggtcgag    660
atgcccaacg gggcgctggc gctgagcgcc gaggacctgg tcggcttcgc ccggctgtac    720
ttcgccggct gcccggaccc tcagccgctg gaccgggcga ccgccgacga catgtgcttc    780
gaccagctgg cctcgatcgc catcggcccg tacggcatgg ccgacggctg gggcctgggc    840
tgggcgaggt tcgacgacgg tgcggcggac gtctacggcc acaacggcac cggcgacggc    900
acctcctgtc atctgcgctt cgacccggcc aacggctccg cggtcgcgct gaccgccaac    960
gccaacaccg gcgcccagct gtgggacgcc ctggtgcccc ggctgcgggc catgggtctg    1020
gcggtcggcg accgccggc gcccgagccg cccaccaccc gccgccggt cccggacgac    1080 tgtccgggcc gctacaccaa cggcgacacc gagttcgtgg tgcagcccgg cgccgacggc    1140
gggctgctgc tgagcttcgg cggggcgccg cactcggagc tgctgtgctc ccccgatctg    1200
cgcttcacca tgcgggagct gggcagcggt gcccggtccc cgggccgctt cgtgaccgat    1260
cccgccaccg gcggatcgg ctacctccag atcaccgggc gactcgcccc ccgacgctga    1320

<210> SEQ ID NO 15
<211> LENGTH: 1353
<212> TYPE: DNA
<213> ORGANISM: Streptomyces hygroscopicus
```

<400> SEQUENCE: 15

```
atgaccacgg ccccacgga cgcggagacg gcacgcggca gcgcggccgt cccgctgtcc      60
cgcaaccgcg actacaacat cctgtggtcc agccagctga tgtccgaact cgccatggag     120
atggccgcgg tagccgtgcc gctgctgatc ctcgcccggc acggctcacc gctccagctg     180
ggcctggcct cctccgcgat ggcggccgcg cacatgatct cggtggtgcc ggccggggtg     240
atcgcggacc gctgggaccg ccgccggctg atgctgggct gccaggtgct acgggtgctg     300
ggcatggtga gcctggccgg cgcgctgctg ctggaccggt acgcgttctg catgtgctg     360
ctggtcgtgg tgctggaggg cttcctcggc tcggtcttcg accccgcgga acatgccgcg     420
ctgccccagg tggtgccgcc cgaccagctc tccacggcgg tggccagaaa cgcggcgcgc     480
ccctacatcg ccaccctcgt ggggccgggc gtcgccggtt tcctcttcag cgccctgccg     540
ctcgggccgt tcgcgaccaa tgcggtgatg ttcgcgctgt cgtccgtggc gctgtgcttt     600
ctgcggctgc cccgggggcg gtccgccgtg gtccggaccg cgacgggcc cgacagcgcc     660
ggagcggacc acgacaggcc ggaccacgac ggacgggacg acgcgaacga cgacactgcg     720
ccgcggcccg gggcgccgc ccaggacttc gctgccggct ccgctgggt gctggggcag      780
ccggtgatcc gcaccacgat ggcctggatg atgatcacga acctggtctt cagctcgctg     840
ctgatcgtgt gctcgcgct ctcgggcgag gacaaggtcg cgccggtga gctgggtctg      900
acgatggcct gcttcggcgc cggcggactg ctcggcgggc tcttcgcggc ccggatgcac     960
gccgccgccc ggccaccggt gatcctcctc ggcttcacct ggaccgccgc cctgggcgcc    1020
gccctgatgg cggtggtgcc caccggtctg ccccagggag cgctgctcgg cctgatggcg    1080
ctcttcgccc cgctcgccaa caccaccgtg ctgacctacc agttgaccgt caccccggac    1140
gagctgcggg gccggatgag cggcgtcgcc gggttctgct cgggggcgc cggtgtcctg     1200
gggcccgcgc tcgccggtgc gctgacgggg gcggccggcg ggggcgtgac ccccgtactc    1260
atctgcgccg gctgcctggt cctggtcgct gtcgcggcca ccgcgagccc cacgctgcgg    1320
cggtttcccg acatcgcgga ccggcagccc tga                                  1353
```

<210> SEQ ID NO 16
<211> LENGTH: 1227
<212> TYPE: DNA
<213> ORGANISM: Streptomyces hygroscopicus

<400> SEQUENCE: 16

```
atgcagaccc ccacacacc gagccaggca cagtcccagc cacggcaaaa gccgcagccg       60
ccgtcgcagt cgcagtcgca gtcgcagccg aatctgaggt ccctgaccgg attacggttc     120
ctgggcttat taccgtcttc ctcacccat gccgcgttcg agggcgtctt cagcgacgcg      180
gacgtgagct ggggcttcct cgacgcgatg gggaacaccg gctatgccgc ggtctcgttc     240
ttcttcgtgc tgagcggctt tgtgatcacc tggtcctacc gctcccgcga caccaccgc      300
acgttctggc gccgacgcgc cttccgggtc ttccccaacc atctcgtggc ctatgtgttc     360
gcgctggctc tgatgctcgc ggcgggcgcc gccttcgacg ccccgccct gatctcccag      420
atgttcctgg tgcacgcatg ggtgcccgac ccgctgttca tcgacaccgg caacacggtg     480
acctggtccc tcgggtcga tgtggtgttc tacgggctct tcccgtgct gctcgtgctg       540
gtgaacaaga tcaagccaac ccgtttgtgg tactgggccg gtgctgccgt gctcatggtg     600
atcgccatcc ccacagtggc gctgaccctg ctcccggaca ccccggccat gtcggtgggc     660
gatgtctccc gcagccagta ctggttcacc tacttcttcc cgctctcccg aaccgtggag     720
```

-continued

```
tgcgtgctgg gcatgctgat ggcgcggatc gtgctgtccg gcaagtggat aggcctgcgg      780
gtgctgcccg cctcggccct ggtggtcgtg gggtatgtcg tcgcacagca actcccttc       840 ctctaccggc tcagcgcggt gctgatcgtg ccgatcgtgc tgctcaccgc ctccgtggcg      900
gtggccgacg ccgagggccg ggggaccccg ctcggcggca aggtcatggt ccggctcggt      960
gaactctcct tcgccttcta cctcgtgcac caggcgctcc tggcgtacgg gcacatcctg     1020
atcagcccga agaacgccca gggcgaggtg ctgccccgta cctgggacac gcctggcggc     1080
atcgcggtga tcgtcctgtc gttcgtggtg tccctgggac tcgcgtggct gctgcacaac     1140
ggggtggaga agccggtgat gcgccgttgg tcccggtcca ggcgccgcgt cacccagcag     1200
ccgccggcaa aggtgccggc aacttag                                          1227
```

<210> SEQ ID NO 17
<211> LENGTH: 1371
<212> TYPE: DNA
<213> ORGANISM: Streptomyces hygroscopicus
<400> SEQUENCE: 17

```
gtgtggagtg cgcgaaagat ctcggccaaa ctccggcgca acggggagt aaggctgacc        60 gctgccagaa gtccgcgcgc gccgtggatg tccggtgccg gcgaccacgc ccggatcatc      120
catcagccga cagtggtgcg gccgccgttg cggcgcaccg agccgcaccg cctgtcgcgc      180
atctggcgag aggtccgcat gcagacaaga caatccaacc cgaacctgag atccctgacc      240
ggtttgcggt tcgtggcgat gctgccggtc ttcctcaccc atgcggcgtt cgagggcgtc      300
ttcagcgacg cgaaggtgag ctggggcttc ctcgacgcga tggggagcac cggctatatg      360
gccgtctcgt tcttcttcgt gctcagcggc tttgtgatca cgtggtcgta ccggcccacc      420
gacaccgcgc gcaagttctg gcgccggcgc ttcttccggg tcttccccaa ccacgtcgtg      480
acctatgcgc tcgccctcgg gctgatcgct gcggtgggc tgagtgtcgg cgtactgccc       540
tcggtcaccc agctcttcct cgtccagtcc tgggtgcccg accggcgtt caccgacacc       600 ggcaacagcg tgagctggtc gctcgcgtg gatgtggtgt tctacgcgct cttcccggtg       660
ctgctcacgc tggtgaacaa gatcaagccg aatcggctct ggtactgggt cggtggctcc      720
gtcatcggtg tggccgtggt accggccatc gcgctcgccg cgctcccgag caccccgag      780 atgccgctcg gcggggtgtc cgtcagccag tactggttca cctacttctt cccgctcttc      840
cggctgctga gtgtgtgct cggcatgctg atggcgcgga tcgtgctgtc cggcaagtgg      900
atacgcctgc gggtgctgcc cgccgccgtc ctcgtggtga tcgcgtacta cttcgcccag      960
caggtcccgt acctctaccg gctgagtgcg gtgacggtgc tgccggtcgc gctgctgacg     1020
gcggcggccg cggtggcgga ctccgagggc cggggcaccc tgttcggcag caaggtcatg     1080
gtctggttcg gcgaactctc cttcgccttc tacctgctgc acaacctcgt cctgaagtac     1140
ggccatctgc tgctcggcca caccgaggag gagggcgagc tggtgggcca cacctggggc     1200
gtgcccgagg gaatcgccct gatcgccgcc gccttcgcgg tgtccctgct gctggcctgg     1260
ctgctgcaca acggagtgga gaagcaggcg atgcgccgct ggtcccgacg caagccggct     1320
ccagtggctg aagtaaccag tgggttctat gcgaaggacg gggcaattta g             1371
```

<210> SEQ ID NO 18
<211> LENGTH: 1026
<212> TYPE: DNA
<213> ORGANISM: Streptomyces hygroscopicus -continued

```
<400> SEQUENCE: 18
gtgctgacgc tccacctgca ggatgacgac gtcgccgcga tcgacgctgt ggctgacgaa      60
ctcagccggc gatacgactc cgtggagtcc acggagttcc aggccgagag ccgcctctac     120
gcggacgagt tgccacgtcg cgtgcgacga gcgctgcacg aataccgcag caccgagaag     180
tccggcatcc tggtcgtcac cggcctgccc gtggacgact cggcgctcgg ggcgaccccg     240
gccgaccgcc ggcacaagcc ggtgccgtcc acgtcactgc gccaggacat cgccttctac     300
ctcatagcca atctgctggg cgaccccatc ggctgggcca cccagcagga cggcttcatc     360
atgcatgacg tctaccccgt ccagggcttc gagcacgaac agatcggctg gggcagcgag     420
gagacgctca cctggcacac cgaggacgcc ttccatccgc tgcgcacgga ctatctcgga     480
ctgatgtgtc tgcgcaatcc ggacggcgtc gagaccaccg cctgcgatat cgccgatgtc     540
gagatcgacg acgagacccg ggagaccctc tcgcaggagc gcttccggat cctgccggac     600
gacgcgcacc gcatccacgg caaggccccg ggggacgaga gcgcacgcga gagtgcgctg     660
cgtgagcgca gccggcagcg ggtggcctcg gccctggagt cgcccgaccc ggtggccgtg     720
ctcttcgggg accgcgacga cccgtatctg cggatcgacc gcactacat gcagggcgtc     780
cagggcgaga ccgagcagcg ggcgctggag accatcggcg ccgcgatcga cgacgccatg     840
tccggtgtcg tgctcagccc cggtgacatc gttttcatcg acaactaccg cgtcgtccac     900
ggacgtaagc cgttccgtgc cgcttcgac ggtacggacc gctggctgcg gcggctcaac     960
atcgcccggg acctgcgcaa gtcgcgcgag gccaggctcg ccgccaccac ccgcgtcatc    1020
tactga                                                              1026

<210> SEQ ID NO 19
<211> LENGTH: 28
<212> TYPE: DNA
<213> ORGANISM: Artificial Sequence
<220> FEATURE:
<223> OTHER INFORMATION: PCR primer
<220> FEATURE:
<221> NAME/KEY: misc_feature
<222> LOCATION: (1)..(32)
<223> OTHER INFORMATION: where n is inosine

<400> SEQUENCE: 19
acstcsggcw cgcaccggcc ngccsaag                                          28

<210> SEQ ID NO 20
<211> LENGTH: 32
<212> TYPE: DNA
<213> ORGANISM: Artificial Sequence
<220> FEATURE:
<223> OTHER INFORMATION: PCR primer

<400> SEQUENCE: 20
agctcsaysc gstagccscg saycttsacc tg                                     32

<210> SEQ ID NO 21
<211> LENGTH: 323
<212> TYPE: PRT
<213> ORGANISM: Streptomyces hygroscopicus

<400> SEQUENCE: 21

Met Ser Ala Thr Pro Arg Pro Arg Pro Val Leu Arg Pro Phe Arg Pro
1               5                   10                  15

Gly Asp Gly Arg Ser Leu Leu Ala Ala Trp Cys Arg Ser Ala Pro Asp
            20                  25                  30
```

```
Asp Pro Ile Thr Ala Ala Arg Phe Arg Thr Leu Ile Leu Leu Asp Pro
            35                  40                  45

Asn Phe Asp Pro Glu Gly Leu Arg Val Ala Asp Leu Asp Gly Gln Val
 50                  55                  60

Val Gly Ala Val Tyr Ala Val Arg Arg Thr Pro Leu Ala Gly Thr
 65                  70                  75                  80

Asp Leu Glu Pro Asp Val Gly Trp Ile Leu Phe Phe Val Asp Pro
                85                  90                  95

Pro His Arg Arg Thr Gly Leu Gly Arg Arg Leu Leu Thr Asp Ala Leu
                100                 105                 110

Asp Trp Leu Arg Gly His Gly Arg Thr Arg Val Asp Phe Ala Pro Tyr
            115                 120                 125

Ala Pro His Tyr Val Leu Pro Gly Leu Asp Arg Ala Ala Tyr Pro Glu
        130                 135                 140

Ala Ala Arg Leu Leu Ala Ser Leu Gly Phe Arg Pro Arg Tyr Glu Ala
145                 150                 155                 160

Ala Ala Met Asp Arg Gly Leu Val Gly Tyr Arg Met Pro Asp Glu Val
                165                 170                 175

Arg Arg His Glu Ala Ala Leu Thr Ala Arg Gly His Arg Phe Gly Thr
                180                 185                 190

Pro Ser Asp Asp Leu Val Asp Leu Leu Gly Leu Ala Glu Glu Phe
            195                 200                 205

Thr Pro Asp Trp Ala Arg Ala Ile Arg Gln Cys Leu Thr Gly Gly Ala
    210                 215                 220

Pro Leu Asp Arg Ile Val Ser Ala Arg Ala Pro Asp Gly Arg Met Ala
225                 230                 235                 240

Gly Trp Ala Met His Gly Ala Tyr Asp Gly Thr Ala Glu Arg Phe Gly
                245                 250                 255

Pro Phe Gly Val Arg Lys Glu Leu Arg Gly Ala Gly Leu Gly Lys Val
                260                 265                 270

Leu Leu His Leu Thr Leu Glu Arg Met Arg Ala Leu Gly Val His Gly
            275                 280                 285

Ala Trp Phe Leu Trp Thr Gly Glu Gln Ser Pro Ala Gly His Leu Tyr
    290                 295                 300

Arg Ala Ser Gly Phe Thr Thr Thr Arg Arg Phe Thr Val Leu Arg Trp
305                 310                 315                 320

Glu Ala Gly

<210> SEQ ID NO 22
<211> LENGTH: 471
<212> TYPE: PRT
<213> ORGANISM: Streptomyces hygroscopicus

<400> SEQUENCE: 22

Met Arg Arg Arg Thr Phe Thr Ala Gly Ala Ala Gly Ala Ala Leu
 1               5                  10                  15

Leu Ala Gly Ala Gly Cys Asp Ala Pro Gly Gly Ala Gly His Gly Asp
                20                  25                  30

Gly Glu His Gly Asp Gly Asp Gly Gly Asp Gly Arg Gly Ser Gly Gly
            35                  40                  45

Arg Arg Gly Ala Pro Val Thr Leu Thr Val Leu Thr His Tyr Ala Ser
    50                  55                  60

Glu Pro Leu Ala Ser Ala Leu Gln Thr Val Val Asp Ala Trp Asn Ala
 65                  70                  75                  80
```

```
Thr His Arg Arg Ile Thr Val Arg Thr Ala Ala Val Lys Phe Pro Asp
                85                  90                  95
Leu Leu Thr Thr Tyr Met Val Arg Gln Ala Ala Gly Gln Gly Ala Asp
            100                 105                 110
Ile Ile His Pro Tyr Cys Leu Trp Thr Gly Gln Leu Val Arg Ala Gly
            115                 120                 125
Val Leu Arg Pro Val Pro Pro Thr Ala Thr Arg Gln Ile Arg Arg Asp
    130                 135                 140
Phe Thr Pro Ala Ala Val Ala Ala Ser Ser Val His Gly Thr Leu Tyr
145                 150                 155                 160
Gly Tyr Pro Thr Glu Val Gln Thr Tyr Ala Leu Tyr Tyr Asn Lys Arg
                165                 170                 175
Leu Leu Arg Gln Ala Gly Ile Asp Gly Pro Gly Thr Trp Gln Glu
            180                 185                 190
Leu Glu Asp Ala Ala Tyr Arg Thr Ala Arg Arg Asp Arg His Gly Asn
            195                 200                 205
Met Leu Val Gln Gly Phe Gly Leu Ser Arg Ala Asp Asp Ala Ser Val
    210                 215                 220
Val Gly Gln Thr Leu Ala Leu Leu Ala Ala Arg Gly Gly Thr Phe Leu
225                 230                 235                 240
Thr Ser Asp Gly Arg Arg Thr Ala Ile Gly Ser Ala Ala Gly Arg Asp
                245                 250                 255
Val Leu Asp Leu Glu Arg Arg Leu Ile Asp Arg Gly Ala Ala Asp Ser
            260                 265                 270
Gly Ile Ser Leu Leu Arg Ala Phe Pro Ser Gly Gln Val Ala Met Ala
            275                 280                 285
Ile Asn Ala Gly Trp Trp Thr Ala Ser Leu Arg Gly Ala Met Gly Ala
    290                 295                 300
Asp Tyr Arg Glu Val Gly Val Ala Pro Val Pro Gly Pro Ala Pro Asp
305                 310                 315                 320
Asp Arg Gly Thr Leu Ala Thr Gly Phe Leu Leu Gly Val Asn Ala Lys
                325                 330                 335
Ser Arg Tyr Pro Gly Glu Ala Trp Glu Phe Leu His Trp Leu Asn Gly
            340                 345                 350
Val Arg Ala Pro Ala Ala Arg Pro Gly Arg Ser Ala Gly Gly Val
            355                 360                 365
Pro Val Ser Arg Met Ser Ala Leu Gln Val Ser Val Gly Ser Met Thr
    370                 375                 380
Gly Arg Ala Asp Asp Met Arg Ala Leu Leu Gly Gly Asp Gly Glu Arg
385                 390                 395                 400
Asp Ala Asp Gly Arg Gly Gly Asp Arg Asn Leu Gly Pro Phe Leu
                405                 410                 415
Asp Ala Leu Arg Tyr Ala Val Pro Glu Pro Asn Gly Pro Arg Ala Gln
            420                 425                 430
Gln Ala Lys Ser Leu Leu Arg Lys Asn Ile Glu Asp Val Trp Thr Gly
            435                 440                 445
Arg Ala Ser Val Asp Ala Ala Leu Arg Thr Ala Gly Arg Gln Ile Asp
    450                 455                 460
Gln Glu Leu Ser Arg Pro Tyr
465                 470

<210> SEQ ID NO 23
<211> LENGTH: 303
```

<212> TYPE: PRT
<213> ORGANISM: Streptomyces hygroscopicus

<400> SEQUENCE: 23

```
Met Ala Ser Ala Gly Gly Gly Pro Val Arg Ala Ala Arg Arg Gln
1               5                   10                  15

Thr Ala Val Ala Tyr Leu Phe Leu Thr Pro Ala Leu Leu Phe Phe Ala
                20                  25                  30

Val Phe Leu Ala Leu Pro Leu Leu Phe Ala Val Leu Leu Ala Gln Ser
                35                  40                  45

Arg Trp Ala Gly Phe Asp Leu Ala Asp Ile Glu Pro Val Gly Met Ala
        50                  55                  60

Asn Phe Thr Asp Leu Phe Ala Arg Gly Ser Thr Phe Leu Thr Pro Val
65                  70                  75                  80

Leu Thr Asn Thr Leu Leu Tyr Ala Val Gly Thr Val Ala Ile Ala Leu
                85                  90                  95

Ile Gly Ala Leu Thr Leu Ala Thr Cys Ile Asp Asn Leu Arg Phe Gln
                100                 105                 110

Gly Leu Trp Arg Thr Leu Tyr Phe Leu Pro Ile Val Thr Thr Val Val
            115                 120                 125

Ala Val Gly Asn Val Trp Lys Tyr Met Tyr Ala Pro Gly Gly Leu Ile
        130                 135                 140

Asn Gly Val Leu Asn Gly Leu Gly Leu His Ser Val Ala Phe Leu Gln
145                 150                 155                 160

Asp Pro Gly Thr Ala Leu Pro Ser Val Val Val Gln Ala Trp Ala
                165                 170                 175

Ser Met Gly Thr Ala Ile Leu Ile Leu Thr Ala Gly Leu Lys Ser Ile
                180                 185                 190

Pro Glu Ala Tyr Tyr Glu Ala Ala Glu Leu Asp Gly Ala Gly Ala Gly
            195                 200                 205

Thr Val Phe Arg Arg Ile Thr Leu Pro Leu Leu Arg Pro Ser Leu Leu
        210                 215                 220

Phe Val Cys Ile Thr Gln Phe Ile Thr Gly Leu Gln Ser Phe Ala Leu
225                 230                 235                 240

Ile Asn Val Met Thr Asp Asp Gly Gly Pro Gly Asp Ala Thr Asn Val
                245                 250                 255

Ala Ala Leu Glu Met Tyr Gln Gln Ala Phe Arg Tyr Gly Asp Trp Gly
            260                 265                 270

Ile Ala Ser Ala Ala Ala Phe Val Leu Phe Leu Val Ile Val Ala Ile
        275                 280                 285

Thr Val Gly Gln Leu Trp Leu Phe Arg Arg Lys Gly Gly Glu Ser
    290                 295                 300
```

<210> SEQ ID NO 24
<211> LENGTH: 296
<212> TYPE: PRT
<213> ORGANISM: Streptomyces hygroscopicus

<400> SEQUENCE: 24

```
Val Ser Arg Ser Ala Arg Arg Pro Gly Arg Arg Pro Trp Gly
1               5                   10                  15

Ser Tyr Ala Val Val Val Ala Gly Ala Ala Leu Thr Leu Val Pro Phe
                20                  25                  30

Leu Asp Met Leu Leu Thr Ser Phe Lys Gly Pro Gly Glu Tyr Gly Lys
            35                  40                  45
```

```
Leu Pro Tyr Arg Phe Leu Pro Gln Ala Phe Asp Leu Ser Asn Tyr Arg
 50                  55                  60

Ala Ala Met Glu Gln Leu Asp Leu Pro Leu Leu Phe Arg Asn Ser Val
 65                  70                  75                  80

Ile Ala Thr Ala Val Ile Thr Gly Ser Ile Leu Val Thr Ser Ala Leu
                 85                  90                  95

Ala Gly Tyr Ala Leu Ala Lys Leu Arg Phe Pro Gly Arg Glu Val Ile
            100                 105                 110

Phe Arg Leu Val Leu Ser Thr Met Met Phe Pro Pro Phe Leu Phe Phe
        115                 120                 125

Ile Pro His Phe Leu Ile Leu Val His Trp Pro Gly Ala Gly Gly Asn
    130                 135                 140

Asp Leu Leu Gly Arg Gly Gly Ala Gly Leu Thr Val Ser Leu Ala Ala
145                 150                 155                 160

Leu Val Met Pro Phe Leu Val Ser Gly Phe Gly Ile Phe Leu Met Arg
                165                 170                 175

Gln Phe Met Val Ser Ile Pro Asp Glu Leu Leu Glu Ala Ala Arg Ile
            180                 185                 190

Asp Gly Ala Gly Glu Phe Ala Leu Trp Trp Arg Ile Val Leu Pro Gln
        195                 200                 205

Thr Lys Pro Val Ala Val Thr Leu Ala Leu Leu Thr Phe Val Asn Ala
210                 215                 220

Trp Asn Glu Tyr Ile Trp Ala Leu Leu Ile Ser Thr Ala Asn Pro Arg
225                 230                 235                 240

Leu Met Thr Leu Pro Val Gly Ile Gln Met Leu Gln Ser Tyr Leu Asp
                245                 250                 255

Pro Asp Arg Met Val Pro Val Met Met Ala Gly Leu Val Leu Ser Ile
            260                 265                 270

Leu Pro Val Leu Leu Leu Phe Leu Leu Gln Lys His Tyr Leu Arg
        275                 280                 285

Gly Val Met Leu Ser Gly Leu Lys
        290                 295

<210> SEQ ID NO 25
<211> LENGTH: 425
<212> TYPE: PRT
<213> ORGANISM: Streptomyces hygroscopicus

<400> SEQUENCE: 25

Met Ser Ser Gly Phe Ser Trp Ala Val Val Ala Thr Val Val Arg Val
 1               5                  10                  15

Ser Asp Pro Ser Gly Gly Thr Met Ala Ser Asp Ser Ser Ser Pro Thr
                 20                  25                  30

Pro Met Pro Ala Val Ser Leu Ile Val Pro Thr Phe Asn Glu Ala Ala
            35                  40                  45

Asn Ile Asp Glu Leu Leu Asp Gly Val Cys Ala Ala Ile Pro Ala Gly
         50                  55                  60

Leu Glu Val Glu Val Leu Phe Val Asp Asp Ser Thr Asp Thr Pro
 65                  70                  75                  80

Glu Val Ile Glu Lys Ala Ala Ala Arg Cys Pro Met Pro Val Ser Val
                 85                  90                  95

Leu His Arg Glu Val Pro Glu Gly Gly Leu Gly Gly Ala Val Val Ala
            100                 105                 110

Gly Ile Ala Arg Thr Ser Ala Pro Trp Ile Met Val Met Asp Ala Asp
        115                 120                 125
```

```
Leu Gln His Pro Pro Glu Leu Leu Pro Gln Leu Ile Glu Ala Gly Glu
        130                 135                 140

Arg Ala Ala Ala Glu Leu Val Ala Ser Arg Tyr Ala Glu Gly Gly
145                 150                 155                 160

Ser Arg Gly Gly Leu Ala Gly Gly Tyr Arg Val Ala Val Ser Gly Ala
                165                 170                 175

Ser Thr Ala Leu Thr Lys Ser Leu Phe Pro Arg Leu Leu Arg Gly Val
                180                 185                 190

Ser Asp Pro Met Ser Gly Cys Phe Ala Ile Arg Arg Glu Ala Val Asp
            195                 200                 205

Arg Ala Val Gln Glu Gly Glu Thr Arg Gln Glu Gly Gly Leu Arg Pro
210                 215                 220

Leu Gly Tyr Lys Ile Leu Leu Glu Leu Ala Val Arg Cys Arg Pro Arg
225                 230                 235                 240

Gly Val Val Glu Val Pro Tyr Glu Phe Gly Glu Arg Phe Ala Gly Glu
                245                 250                 255

Ser Lys Ser Thr Val Arg Glu Gly Leu Arg Phe Leu Arg His Leu Ala
            260                 265                 270

Glu Leu Arg Thr Ser Asp Lys Arg Ala Arg Met Val Ala Phe Gly Leu
        275                 280                 285

Ile Gly Val Ser Gly Phe Val Pro Asn Leu Leu Ala Leu Trp Ala Leu
        290                 295                 300

Thr Gly Ala Thr Thr Leu His Tyr Ala Val Ala Glu Val Leu Ala Asn
305                 310                 315                 320

Gln Leu Gly Val Leu Trp Asn Phe Ala Leu Leu Asp Phe Leu Val Tyr
                325                 330                 335

Arg Ser Gly Lys Pro Gly Arg Gly Ala Gly Arg Leu Leu Gly Phe Ala
                340                 345                 350

Ala Leu Ser Asn Ala Asp Leu Leu Ala Arg Ile Pro Leu Met Met Leu
            355                 360                 365

Phe Val Glu Gln Ala Gly Met Gly Pro Val Pro Ala Thr Val Ile Ser
370                 375                 380

Leu Val Val Phe Ala Leu Arg Phe Leu Leu Val Asp Thr Leu Ile
385                 390                 395                 400

Tyr Arg Arg Lys Gly Ala Ala Lys Arg Ala Ala Asp Ala Ala Val
                405                 410                 415

Thr Gly Gly Gln Gly Glu Arg Ala Ala
            420                 425

<210> SEQ ID NO 26
<211> LENGTH: 470
<212> TYPE: PRT
<213> ORGANISM: Streptomyces hygroscopicus

<400> SEQUENCE: 26

Val Thr Val Val Leu Leu Ala Leu Ser Asp Arg Tyr Gly Tyr Asn Val
1                   5                   10                  15

Asp Glu Leu Tyr Phe Arg Leu Leu Gly Glu His Gly Trp Ala Trp Gly
                20                  25                  30

Tyr Thr Asp Gln Pro Pro Leu Val Pro Ala Leu Val His Ala Thr Ala
            35                  40                  45

Gln Val Leu Gly Asp Ser Val Trp Ala Ile Arg Val Pro Ala Ala Leu
        50                  55                  60

Cys Ala Gly Ala Val Val Leu Leu Gly Ala Leu Ile Thr Ala Glu Leu
```

-continued

```
            65                  70                  75                  80
Gly Gly Thr Arg Arg Ala Gln Thr Leu Ser Ala Leu Gly Leu Gly Ser
                    85                  90                  95
Ser Phe Leu Val Leu Ser Val Gly His Ile Met Val Thr Thr Thr Leu
                100                 105                 110
Asp Met Leu Ala Trp Ala Val Leu Leu Phe Val Leu Arg Ala Leu
            115                 120                 125
Leu Arg Ser Glu Gly Lys Trp Trp Leu Trp Ala Gly Val Val Leu Gly
        130                 135                 140
Leu Ala Leu Tyr Ala Lys Tyr Ile Val Ala Leu Leu Pro Val Ala Leu
145                 150                 155                 160
Leu Ala Gly Leu Ala Leu Val Gly Pro Arg Lys Val Phe Arg Asp Arg
                165                 170                 175
Trp Leu Tyr Ala Gly Ile Ala Leu Ala Leu Ala Ile Gly Ser Pro Asn
                180                 185                 190
Leu Ile Tyr Gln Ala Thr His Asp Phe Pro Gln Leu Gln Met Ala Asp
            195                 200                 205
Ala Leu Gly Ala Thr Asp Gly Pro Met Asn Arg Val Ile Phe Val Pro
        210                 215                 220
Ser Leu Val Ile Leu Leu Gly Pro Val Leu Thr Val Val Trp Val Ala
225                 230                 235                 240
Gly Leu Val Lys Leu Leu Arg Asp Pro Ala Trp Arg Pro Val Arg Ala
                245                 250                 255
Leu Ala Pro Ala Phe Val Val Gly Val Ala Leu Thr Leu Tyr Gly Gly
                260                 265                 270
Gly Arg Pro Asp Tyr Val Gly Gly Phe Leu Ile Gly Leu Phe Ala Ala
                275                 280                 285
Gly Ala Val Ala Ala Asp Arg Trp Met Gly Arg Arg Thr Ser Arg Arg
        290                 295                 300
Val Leu Leu Cys Ala Gly Leu Ala Ala Ser Ala Val Leu Gln Val Leu
305                 310                 315                 320
Met Ala Leu Pro Val Leu Pro Gln Ser Ser Pro Phe Val Pro Leu Asn
                325                 330                 335
Asn Ile Ser Leu Glu Ser Val Gly Trp Pro Arg Leu Ala Glu Gln Val
            340                 345                 350
Arg Thr Ala Tyr Glu Ala Leu Pro Arg Gln Gln Arg Glu Arg Ala Val
        355                 360                 365
Val Leu Ala Asp Asn Leu Gly Glu Ile Gly Ala Leu Asp Arg Tyr Gly
        370                 375                 380
His Gly Leu Pro Ala Val Phe Ser Gly His Asn Glu Leu His Lys Trp
385                 390                 395                 400
Gly Pro Pro Pro Glu Arg Ala Asp Val Val Val Ala Val Gly Val Pro
                405                 410                 415
Arg Ser Arg Leu Ala Ala Gly Phe Thr Ser Cys Thr Val Val Gly Arg
                420                 425                 430
Val Asp Asn Gly Val Gly Val Glu Asn Ala Glu Gln Gly Arg Pro Ile
            435                 440                 445
Thr Val Cys His Gly Arg Lys Ala Ser Trp Ala Arg Leu Trp Pro Ser
        450                 455                 460
Tyr His Tyr Leu Ser Gly
465                 470

<210> SEQ ID NO 27
```

-continued

```
<211> LENGTH: 509
<212> TYPE: PRT
<213> ORGANISM: Streptomyces hygroscopicus

<400> SEQUENCE: 27

Met Thr Thr Ser Leu Asp Arg Asp Ser Arg Ala Ala Ala Gly Pro
1               5                   10                  15

Gly Val Phe Arg Pro Ala Pro Met Ala Trp Arg Pro Val Ala Val
                20                  25                  30

Val Ala Ala Leu Ala Val Leu Leu Phe Ala Phe Ala Gly Glu Tyr Gly
            35                  40                  45

Tyr His Ala Asp Glu Leu Tyr Phe Arg Leu Leu Gly Val His Gly Phe
    50                  55                  60

Ala Trp Gly Tyr Val Asp Gln Pro Pro Leu Leu Pro Leu Ala Val Arg
65                  70                  75                  80

Thr Ser Met Glu Ile Phe Gly Asp Ser Met Trp Ala Ile Arg Val Pro
                85                  90                  95

Ala Val Leu Cys Ala Ala Ala Val Thr Ala Leu Gly Ala Met Ile Ala
                100                 105                 110

Ala Glu Leu Gly Gly Ser Arg Arg Ala Gln Thr Leu Thr Ala Phe Gly
                115                 120                 125

Val Ala Thr Ser Thr Met Val Leu Ser Phe Gly His Trp Ile Leu Thr
            130                 135                 140

Thr Ser Phe Asp Thr Val Ala Trp Ala Ala Val Leu Leu Phe Val Met
145                 150                 155                 160

Arg Val Leu Leu Arg Gly Glu Ser Lys Trp Trp Leu Trp Ala Gly Val
                165                 170                 175

Val Val Gly Val Ala Leu Tyr Ala Lys Tyr Ile Val Leu Leu Leu Pro
            180                 185                 190

Val Ala Leu Leu Val Gly Leu Ala Leu Val Gly Pro Arg Lys Val Phe
            195                 200                 205

Arg Asp Gly Lys Leu Tyr Ala Gly Thr Ala Leu Ala Leu Val Ile Gly
210                 215                 220

Ser Pro Asn Leu Ile Tyr Gln Ala Thr His Asp Phe Pro Gln Leu Gln
225                 230                 235                 240

Met Ala Glu Gly Leu Ala Gly Thr Asp Gly Glu Ala Asn Arg Ala Met
                245                 250                 255

Phe Ala Thr Asn Leu Ile Leu Leu Phe Gly Pro Ala Leu Phe Val Leu
                260                 265                 270

Cys Met Ile Gly Leu Val Lys Leu Phe Arg Val Pro Glu Trp Lys Pro
                275                 280                 285

Val Arg Thr Leu Ala Val Gly Tyr Leu Ala Ala Thr Ala Ala Ser Tyr
290                 295                 300

Leu Ile Glu Gly Gly Arg Pro Asp Tyr Thr Gly Gly Leu Leu Ile Ala
305                 310                 315                 320

Leu Leu Ala Ala Gly Cys Val Thr Ala Asp Arg Trp Ala Gly Ala Arg
                325                 330                 335

Lys Leu Arg Leu Ser Val Leu Ala Val Ser Leu Thr Leu Ser Thr Ala
                340                 345                 350

Val Gln Met Leu Leu Ser Leu Pro Val Ile Pro Lys Ser Ser Leu Arg
                355                 360                 365

Asp Phe Gln Ile Ala Ser Met Ala Leu Glu Thr Val Gly Trp Pro Arg
                370                 375                 380

Leu Val Gln Gln Thr Glu Ala Ala Tyr Arg Ala Leu Pro Ala Ala Asp
```

```
                385                 390                 395                 400
Arg Asp Arg Ala Ile Val Leu Thr Glu Asn Phe Gly Glu Ala Gly Ala
                405                 410                 415

Leu Asp His Tyr Gly His Gly Leu Pro Lys Val Tyr Ser Gly His Asn
                420                 425                 430

Glu Leu Tyr His Trp Gly Pro Pro Gln Arg Ala Glu Val Val Val
                435                 440                 445

Ala Val Gly Ile Asp Arg Asn Arg Leu Ser Ala Asp Phe Thr Ser Cys
                450                 455                 460

Lys Val Asp His Ile Asp Asn Arg Leu Gly Ile Asp Asn Pro Glu
465                 470                 475                 480

Gln Gly Val Pro Ile Thr Val Cys His Gly Pro Lys Lys Pro Trp Ser
                485                 490                 495

Ala Leu Trp Pro Thr Tyr Arg His Tyr Asn Ala Tyr Leu
                500                 505

<210> SEQ ID NO 28
<211> LENGTH: 337
<212> TYPE: PRT
<213> ORGANISM: Streptomyces hygroscopicus

<400> SEQUENCE: 28

Met Ser Thr Glu Val Ser Glu Ala Gln Ala Arg Arg Ala Val Ala Asp
1                   5                  10                  15

Ile Phe Asn Ser Thr Leu Ala Ser Ser Ala Ile Gly Ala Ala Trp Glu
                20                  25                  30

Leu Gly Ala Leu Asp Glu Leu Arg Glu Asn Gly Lys Leu Asp Val Ser
            35                  40                  45

Asp Phe Ala Val Arg His Asp Leu His Glu Pro Ala Val Val Gly Met
        50                  55                  60

Phe Thr Ala Leu Ala Ser Val Gly Ile Val Arg Arg Glu Gly Ala Thr
65                  70                  75                  80

Val Val Val Gly Pro Tyr Phe Asp Glu Ala Asn His His Arg Ser Leu
                85                  90                  95

Phe His Trp Leu Asn Gln Gly Ser Gly Glu Leu Phe Arg Arg Met Pro
            100                 105                 110

Gln Val Leu Pro Asn Glu Asn Arg Thr Gly Lys Phe Tyr Gln Arg Asp
        115                 120                 125

Ala Gly Ala Ile Ser Tyr Ala Cys Arg Glu Ile Ser Glu Arg Tyr Phe
    130                 135                 140

Asp Pro Ala Phe Trp Ala Ala Val Asp Gly Leu Gly Tyr Thr Pro Thr
145                 150                 155                 160

Thr Val Ala Asp Leu Gly Ser Gly Ser Gly Glu Arg Leu Ile Gln Ile
                165                 170                 175

Ala Arg Arg Phe Pro Gly Val Arg Gly Leu Gly Val Asp Ile Ala Asp
            180                 185                 190

Gly Ala Ile Ala Met Ala Glu Lys Glu Val Ala Ala Lys Gly Phe Gly
        195                 200                 205

Asp Gln Ile Ser Phe Val Arg Gly Asp Ala Arg Thr Ile Asp Gln Val
    210                 215                 220

Ser Ala Arg Gly Glu Phe Ala Glu Val Asp Leu Leu Thr Cys Phe Met
225                 230                 235                 240

Met Gly His Asp Phe Trp Pro Arg Glu Asn Cys Val Gln Thr Leu Arg
                245                 250                 255
```

```
Lys Leu Arg Ala Ala Phe Pro Asn Val Arg Arg Phe Leu Leu Gly Asp
            260                 265                 270

Ala Thr Arg Thr Val Gly Ile Pro Asp Arg Glu Leu Pro Val Phe Thr
            275                 280                 285

Leu Gly Phe Glu Phe Gly His Asp Met Met Gly Val Tyr Leu Pro Thr
            290                 295                 300

Leu Asp Glu Trp Asp Gly Val Phe Glu Glu Gly Trp Arg Cys Val
305                 310                 315                 320

Lys Lys His Ala Ile Asp Ser Leu Ser Val Ser Val Phe Glu Leu
            325                 330                 335

Glu
```

```
<210> SEQ ID NO 29
<211> LENGTH: 439
<212> TYPE: PRT
<213> ORGANISM: Streptomyces hygroscopicus

<400> SEQUENCE: 29

Met Asp His Glu Ser Leu His Ser Thr Leu Thr Glu Leu Ala Ala Arg
1               5                   10                  15

His Arg Val Pro Gly Ala Gln Leu Ala Val Ile His Glu Gly Glu Arg
            20                  25                  30

Phe Leu Val His Thr Gly Val Cys Asp Thr Ala Ser Gly Ala Pro Val
        35                  40                  45

Glu Arg His Thr Ala Phe Pro Val Gly Ser Leu Thr Lys Pro Phe Thr
    50                  55                  60

Ala Ala Leu Ala Met Ile Leu Val Ala Asp Gly Asp Val Asp Leu Asp
65                  70                  75                  80

Glu Pro Leu Arg Gly Gln Leu Pro Glu Phe Gly Ala Gly Glu Leu Val
                85                  90                  95

Thr Leu Arg Gln Leu Leu Ser His Thr Ser Gly Leu Pro Ser Asp Val
            100                 105                 110

Pro Glu Gly Ser Asp Glu Ala Gly Gly Asp Arg Ala Arg Trp Val
            115                 120                 125

Ala Arg Tyr Cys Arg Thr Ala Asp Leu Thr His Ala Pro Gly Thr Val
    130                 135                 140

Phe Ser Tyr Ser Asn Ile Gly Tyr Val Val Gly Arg Leu Ile Glu
145                 150                 155                 160

Ala Val Thr Gly Met Ser Trp Gln Glu Ala Ile Ser Ala Ile Leu Leu
                165                 170                 175

Glu Pro Leu Gly Thr Arg Pro Ala Phe Val Val Gly Ala Pro Ala Thr
            180                 185                 190

Arg Pro Val Ala Thr Gly His Ala Val Gln Ala Val Arg Asp Arg Val
        195                 200                 205

Val Pro Ile Pro Asp Gln Asp Leu Pro Glu Val Glu Met Pro Asn Gly
    210                 215                 220

Ala Leu Ala Leu Ser Ala Glu Asp Leu Val Gly Phe Ala Arg Leu Tyr
225                 230                 235                 240

Phe Ala Gly Cys Pro Asp Pro Gln Pro Leu Asp Arg Ala Thr Ala Asp
                245                 250                 255

Asp Met Cys Phe Asp Gln Leu Ala Ser Ile Ala Ile Gly Pro Tyr Gly
            260                 265                 270

Met Ala Asp Gly Trp Gly Leu Gly Trp Ala Arg Phe Asp Asp Gly Ala
        275                 280                 285
```

```
Ala Asp Val Tyr Gly His Asn Gly Thr Gly Asp Gly Thr Ser Cys His
    290                 295                 300

Leu Arg Phe Asp Pro Ala Asn Gly Ser Ala Val Ala Leu Thr Ala Asn
305                 310                 315                 320

Ala Asn Thr Gly Ala Gln Leu Trp Asp Ala Leu Val Pro Arg Leu Arg
                325                 330                 335

Ala Met Gly Leu Ala Val Gly Asp Arg Pro Ala Pro Glu Pro Pro Thr
            340                 345                 350

Thr Pro Pro Pro Val Pro Asp Asp Cys Pro Gly Arg Tyr Thr Asn Gly
        355                 360                 365

Asp Thr Glu Phe Val Val Gln Pro Gly Ala Asp Gly Leu Leu Leu
    370                 375                 380

Ser Phe Gly Gly Ala Pro His Ser Glu Leu Leu Cys Ser Pro Asp Leu
385                 390                 395                 400

Arg Phe Thr Met Arg Glu Leu Gly Ser Gly Ala Arg Ser Pro Gly Arg
                405                 410                 415

Phe Val Thr Asp Pro Ala Thr Gly Arg Ile Gly Tyr Leu Gln Ile Thr
            420                 425                 430

Gly Arg Leu Ala Pro Arg Arg
            435

<210> SEQ ID NO 30
<211> LENGTH: 450
<212> TYPE: PRT
<213> ORGANISM: Streptomyces hygroscopicus

<400> SEQUENCE: 30

Met Thr Thr Ala Pro Thr Asp Ala Glu Thr Ala Arg Gly Ser Ala Ala
1               5                   10                  15

Val Pro Leu Ser Arg Asn Arg Asp Tyr Asn Ile Leu Trp Ser Ser Gln
            20                  25                  30

Leu Met Ser Glu Leu Ala Met Glu Met Ala Ala Val Ala Val Pro Leu
        35                  40                  45

Leu Ile Leu Ala Arg His Gly Ser Pro Leu Gln Leu Gly Leu Ala Ser
    50                  55                  60

Ser Ala Met Ala Ala Ala His Met Ile Ser Val Val Pro Ala Gly Val
65                  70                  75                  80

Ile Ala Asp Arg Trp Asp Arg Arg Leu Met Leu Gly Cys Gln Val
                85                  90                  95

Leu Arg Val Leu Gly Met Val Ser Leu Ala Gly Ala Leu Leu Leu Asp
            100                 105                 110

Arg Tyr Ala Phe Trp His Val Leu Leu Val Val Leu Glu Gly Phe
        115                 120                 125

Leu Gly Ser Val Phe Asp Pro Ala Glu His Ala Ala Leu Pro Gln Val
    130                 135                 140

Val Pro Pro Asp Gln Leu Ser Thr Ala Val Ala Arg Asn Ala Ala Arg
145                 150                 155                 160

Pro Tyr Ile Ala Thr Leu Val Gly Pro Gly Val Ala Gly Phe Leu Phe
                165                 170                 175

Ser Ala Leu Pro Leu Gly Pro Phe Ala Thr Asn Ala Val Met Phe Ala
            180                 185                 190

Leu Ser Ser Val Ala Leu Cys Phe Leu Arg Leu Pro Arg Gly Arg Ser
        195                 200                 205

Ala Val Val Arg Thr Gly Asp Gly Pro Asp Ser Ala Gly Ala Asp His
    210                 215                 220
```

```
Asp Arg Pro Asp His Asp Gly Arg Asp Ala Asn Asp Asp Thr Ala
225                 230                 235                 240

Pro Arg Pro Gly Gly Ala Ala Gln Asp Phe Ala Ala Gly Phe Arg Trp
            245                 250                 255

Val Leu Gly Gln Pro Val Ile Arg Thr Thr Met Ala Trp Met Met Ile
            260                 265                 270

Thr Asn Leu Val Phe Ser Ser Leu Ile Val Leu Leu Ala Leu Ser
        275                 280                 285

Gly Glu Asp Lys Val Gly Ala Gly Glu Leu Gly Leu Thr Met Ala Cys
        290                 295                 300

Phe Gly Ala Gly Gly Leu Leu Gly Gly Leu Phe Ala Ala Arg Met His
305                 310                 315                 320

Ala Ala Ala Arg Pro Pro Val Ile Leu Leu Gly Phe Thr Trp Thr Ala
                325                 330                 335

Ala Leu Gly Ala Ala Leu Met Ala Val Val Pro Thr Gly Leu Pro Gln
            340                 345                 350

Gly Ala Leu Leu Gly Leu Met Ala Leu Phe Ala Pro Leu Ala Asn Thr
            355                 360                 365

Thr Val Leu Thr Tyr Gln Leu Thr Val Thr Pro Asp Glu Leu Arg Gly
370                 375                 380

Arg Met Ser Gly Val Ala Gly Phe Cys Ser Gly Gly Ala Gly Val Leu
385                 390                 395                 400

Gly Pro Ala Leu Gly Gly Ala Leu Thr Gly Ala Ala Gly Gly Gly Val
                405                 410                 415

Thr Pro Val Leu Ile Cys Ala Gly Cys Leu Val Leu Val Ala Val Ala
                420                 425                 430

Ala Thr Ala Ser Pro Thr Leu Arg Arg Phe Pro Asp Ile Ala Asp Arg
            435                 440                 445

Gln Pro
   450

<210> SEQ ID NO 31
<211> LENGTH: 408
<212> TYPE: PRT
<213> ORGANISM: Streptomyces hygroscopicus

<400> SEQUENCE: 31

Met Gln Thr Pro His Thr Pro Ser Gln Ala Gln Ser Gln Pro Arg Gln
1               5                   10                  15

Lys Pro Gln Pro Pro Ser Gln Ser Gln Ser Gln Pro Asn Leu
            20                  25                  30

Arg Ser Leu Thr Gly Leu Arg Phe Leu Gly Leu Leu Pro Val Phe Leu
        35                  40                  45

Thr His Ala Ala Phe Glu Gly Val Phe Ser Asp Ala Asp Val Ser Trp
    50                  55                  60

Gly Phe Leu Asp Ala Met Gly Asn Thr Gly Tyr Ala Ala Val Ser Phe
65              70                  75                  80

Phe Phe Val Leu Ser Gly Phe Val Ile Thr Trp Ser Tyr Arg Ser Arg
                85                  90                  95

Asp Thr Thr Arg Thr Phe Trp Arg Arg Arg Ala Phe Arg Val Phe Pro
                100                 105                 110

Asn His Leu Val Ala Tyr Val Phe Ala Leu Ala Leu Met Leu Ala Ala
            115                 120                 125

Gly Ala Ala Phe Asp Ala Pro Ala Leu Ile Ser Gln Met Phe Leu Val
```

```
            130                 135                 140
His Ala Trp Val Pro Asp Pro Leu Phe Ile Asp Thr Gly Asn Thr Val
145                 150                 155                 160

Thr Trp Ser Leu Gly Val Asp Val Val Phe Tyr Gly Leu Phe Pro Val
                165                 170                 175

Leu Leu Val Leu Val Asn Lys Ile Lys Pro Thr Arg Leu Trp Tyr Trp
            180                 185                 190

Ala Gly Ala Ala Val Leu Met Val Ile Ala Ile Pro Thr Val Ala Leu
            195                 200                 205

Thr Leu Leu Pro Asp Thr Pro Ala Met Ser Val Gly Asp Val Ser Arg
    210                 215                 220

Ser Gln Tyr Trp Phe Thr Tyr Phe Phe Pro Leu Ser Arg Thr Val Glu
225                 230                 235                 240

Cys Val Leu Gly Met Leu Met Ala Arg Ile Val Leu Ser Gly Lys Trp
                245                 250                 255

Ile Gly Leu Arg Val Leu Pro Ala Ser Ala Leu Val Val Gly Tyr
            260                 265                 270

Val Val Ala Gln Gln Leu Pro Phe Leu Tyr Arg Leu Ser Ala Val Leu
            275                 280                 285

Ile Val Pro Ile Val Leu Leu Thr Ala Ser Val Ala Val Ala Asp Ala
    290                 295                 300

Glu Gly Arg Gly Thr Pro Leu Gly Gly Lys Val Met Val Arg Leu Gly
305                 310                 315                 320

Glu Leu Ser Phe Ala Phe Tyr Leu Val His Gln Ala Leu Leu Ala Tyr
                325                 330                 335

Gly His Ile Leu Ile Ser Pro Lys Asn Ala Gln Gly Glu Val Leu Pro
            340                 345                 350

Arg Thr Trp Asp Thr Pro Gly Gly Ile Ala Val Ile Val Leu Ser Phe
                355                 360                 365

Val Val Ser Leu Gly Leu Ala Trp Leu Leu His Asn Gly Val Glu Lys
            370                 375                 380

Pro Val Met Arg Arg Trp Ser Arg Ser Arg Arg Val Thr Gln Gln
385                 390                 395                 400

Pro Pro Ala Lys Val Pro Ala Thr
                405

<210> SEQ ID NO 32
<211> LENGTH: 456
<212> TYPE: PRT
<213> ORGANISM: Streptomyces hygroscopicus

<400> SEQUENCE: 32

Val Trp Ser Ala Arg Lys Ile Ser Ala Lys Leu Arg Arg Asn Gly Gly
1               5                   10                  15

Val Arg Leu Thr Ala Ala Arg Ser Pro Arg Ala Pro Trp Met Ser Gly
            20                  25                  30

Ala Gly Asp His Ala Arg Ile Ile His Gln Pro Thr Val Val Arg Pro
            35                  40                  45

Pro Leu Arg Arg Thr Glu Pro His Arg Leu Ser Arg Ile Trp Arg Glu
    50                  55                  60

Val Arg Met Gln Thr Arg Gln Ser Asn Pro Asn Leu Arg Ser Leu Thr
65                  70                  75                  80

Gly Leu Arg Phe Val Ala Met Leu Pro Val Phe Leu Thr His Ala Ala
                85                  90                  95
```

-continued

```
Phe Glu Gly Val Phe Ser Asp Ala Lys Val Ser Trp Gly Phe Leu Asp
            100                 105                 110
Ala Met Gly Ser Thr Gly Tyr Met Ala Val Ser Phe Phe Phe Val Leu
            115                 120                 125
Ser Gly Phe Val Ile Thr Trp Ser Tyr Arg Pro Thr Asp Thr Ala Arg
            130                 135                 140
Lys Phe Trp Arg Arg Arg Phe Phe Arg Val Phe Pro Asn His Val Val
145                 150                 155                 160
Thr Tyr Ala Leu Ala Leu Gly Leu Ile Ala Ala Val Gly Leu Ser Val
                165                 170                 175
Gly Val Leu Pro Ser Val Thr Gln Leu Phe Leu Val Gln Ser Trp Val
            180                 185                 190
Pro Asp Pro Ala Phe Thr Asp Thr Gly Asn Ser Val Ser Trp Ser Leu
            195                 200                 205
Ala Val Asp Val Val Phe Tyr Ala Leu Phe Pro Val Leu Leu Thr Leu
            210                 215                 220
Val Asn Lys Ile Lys Pro Asn Arg Leu Trp Tyr Trp Val Gly Gly Ser
225                 230                 235                 240
Val Ile Gly Val Ala Val Pro Ala Ile Ala Leu Ala Ala Leu Pro
                245                 250                 255
Ser Thr Pro Glu Met Pro Leu Gly Gly Val Ser Val Ser Gln Tyr Trp
            260                 265                 270
Phe Thr Tyr Phe Phe Pro Leu Phe Arg Leu Leu Glu Cys Val Leu Gly
            275                 280                 285
Met Leu Met Ala Arg Ile Val Leu Ser Gly Lys Trp Ile Arg Leu Arg
            290                 295                 300
Val Leu Pro Ala Ala Val Leu Val Val Ile Ala Tyr Tyr Phe Ala Gln
305                 310                 315                 320
Gln Val Pro Tyr Leu Tyr Arg Leu Ser Ala Val Thr Val Leu Pro Val
                325                 330                 335
Ala Leu Leu Thr Ala Ala Ala Val Ala Asp Ser Glu Gly Arg Gly
            340                 345                 350
Thr Leu Phe Gly Ser Lys Val Met Val Trp Phe Gly Glu Leu Ser Phe
            355                 360                 365
Ala Phe Tyr Leu Leu His Asn Leu Val Leu Lys Tyr Gly His Leu Leu
            370                 375                 380
Leu Gly His Thr Glu Glu Gly Leu Val Gly His Thr Trp Gly
385                 390                 395                 400
Val Pro Glu Gly Ile Ala Leu Ile Ala Ala Phe Ala Val Ser Leu
                405                 410                 415
Leu Leu Ala Trp Leu Leu His Asn Gly Val Lys Gln Ala Met Arg
            420                 425                 430
Arg Trp Ser Arg Arg Lys Pro Ala Pro Val Ala Glu Val Thr Ser Gly
            435                 440                 445
Phe Tyr Ala Lys Asp Gly Ala Ile
450                 455

<210> SEQ ID NO 33
<211> LENGTH: 341
<212> TYPE: PRT
<213> ORGANISM: Streptomyces hygroscopicus

<400> SEQUENCE: 33

Val Leu Thr Leu His Leu Gln Asp Asp Val Ala Ala Ile Asp Ala
1               5                   10                  15
```

| | | | | | | | | | | | |
|---|---|---|---|---|---|---|---|---|---|---|---|
|Val|Ala|Asp|Glu|Leu|Ser|Arg|Arg|Tyr|Asp|Ser|Val|Glu|Ser|Thr|Glu|
| | |20| | | |25| | | |30| |

Val Ala Asp Glu Leu Ser Arg Arg Tyr Asp Ser Val Glu Ser Thr Glu
        20                  25                  30

Phe Gln Ala Glu Ser Arg Leu Tyr Ala Asp Glu Leu Pro Arg Arg Val
            35                  40                  45

Arg Arg Ala Leu His Glu Tyr Arg Ser Thr Glu Lys Ser Gly Ile Leu
 50                  55                  60

Val Val Thr Gly Leu Pro Val Asp Ser Ala Leu Gly Ala Thr Pro
 65                  70                  75                  80

Ala Asp Arg Arg His Lys Pro Val Pro Ser Thr Ser Leu Arg Gln Asp
                85                  90                  95

Ile Ala Phe Tyr Leu Ile Ala Asn Leu Leu Gly Asp Pro Ile Gly Trp
            100                 105                 110

Ala Thr Gln Gln Asp Gly Phe Ile Met His Asp Val Tyr Pro Val Gln
            115                 120                 125

Gly Phe Glu His Glu Gln Ile Gly Trp Gly Ser Glu Glu Thr Leu Thr
130                 135                 140

Trp His Thr Glu Asp Ala Phe His Pro Leu Arg Thr Asp Tyr Leu Gly
145                 150                 155                 160

Leu Met Cys Leu Arg Asn Pro Asp Gly Val Glu Thr Thr Ala Cys Asp
                165                 170                 175

Ile Ala Asp Val Glu Ile Asp Glu Thr Arg Glu Thr Leu Ser Gln
            180                 185                 190

Glu Arg Phe Arg Ile Leu Pro Asp Asp Ala His Arg Ile His Gly Lys
            195                 200                 205

Ala Pro Gly Asp Glu Ser Ala Arg Glu Ser Ala Leu Arg Glu Arg Ser
210                 215                 220

Arg Gln Arg Val Ala Ser Ala Leu Glu Ser Pro Asp Pro Val Ala Val
225                 230                 235                 240

Leu Phe Gly Asp Arg Asp Asp Pro Tyr Leu Arg Ile Asp Pro His Tyr
                245                 250                 255

Met Gln Gly Val Gln Gly Glu Thr Glu Gln Arg Ala Leu Glu Thr Ile
            260                 265                 270

Gly Ala Ala Ile Asp Asp Ala Met Ser Gly Val Val Leu Ser Pro Gly
        275                 280                 285

Asp Ile Val Phe Ile Asp Asn Tyr Arg Val Val His Gly Arg Lys Pro
        290                 295                 300

Phe Arg Ala Arg Phe Asp Gly Thr Asp Arg Trp Leu Arg Arg Leu Asn
305                 310                 315                 320

Ile Ala Arg Asp Leu Arg Lys Ser Arg Glu Ala Arg Leu Ala Ala Thr
                325                 330                 335

Thr Arg Val Ile Tyr
            340

<210> SEQ ID NO 34
<211> LENGTH: 882
<212> TYPE: DNA
<213> ORGANISM: Streptomyces hygroscopicus

<400> SEQUENCE: 34
gtgctgagct gctactcctc ctcggtcgcg atggagatcc tctcccgctc gctgtccgag      60
acgatcgagt cggtggccct ggtccacccg accttcgaca acatcgccga cctgctgcgc     120
ggcaacggcc tgaagctggt gccgctggcg gaggacccgc tgcacggcga cgacctcgac     180
gtgagcctgc tgaagtcggt gggctgtgtc ttcctcacca cgcccaacaa ccccaccggc     240

-continued

```
aaggtcgtct cccgggagcg gctgacccgg ctggccgagc agtgcgccga gcacggcgtc    300
atcctcgcgc tggacacgtc cttccgcggc ttcgacaccc gcgcccacta cgaccactac    360
gaggtgctca acgccagtgg tgtgcgctgg gtggtgatcg aggacaccgg caagctgtgg    420
ccgaccctcg acctcaaggt cggcatgctc gtccactccg agaacctcgc gctgccggtc    480
gagaagatct actccgacat cctgctcggt gtctccccgc tgatcctcgc gatggtccgc    540
cgcttctccg aggacgccgc ggccggcggt ctggaggatc tgcaccgctt catcgccgcc    600
aaccgtgcca tggtgcgcgc ggaactcgcc ggtctgccgg gcgtcacggt ccccgacccc    660
gacagccggg ccagcgtcga gcgggtcgcc atcgatgacc tgacgggcac gcaggtctgg    720
gcgaagctgc gggagcacaa cgtctacgcg ctcccgtgcc gccgttccac ctgggccaac    780
ccgtccgagg gtgaccacac cctgcggctc gcgctggccc ggtccacgga cccgctcgcc    840
cagtccgtgc gcgccctgcg ccacgtgctg aaacagcgtt ga                      882
```

<210> SEQ ID NO 35
<211> LENGTH: 293
<212> TYPE: PRT
<213> ORGANISM: Streptomyces hygroscopicus

<400> SEQUENCE: 35

```
Val Leu Ser Cys Tyr Ser Ser Val Ala Met Glu Ile Leu Ser Arg
1               5                   10                  15

Ser Leu Ser Glu Thr Ile Glu Ser Val Ala Leu Val His Pro Thr Phe
                20                  25                  30

Asp Asn Ile Ala Asp Leu Leu Arg Gly Asn Gly Leu Lys Leu Val Pro
            35                  40                  45

Leu Ala Glu Asp Pro Leu His Gly Asp Asp Leu Asp Val Ser Leu Leu
        50                  55                  60

Lys Ser Val Gly Cys Val Phe Leu Thr Thr Pro Asn Asn Pro Thr Gly
65                  70                  75                  80

Lys Val Val Ser Arg Glu Arg Leu Thr Arg Leu Ala Glu Gln Cys Ala
                85                  90                  95

Glu His Gly Val Ile Leu Ala Leu Asp Thr Ser Phe Arg Gly Phe Asp
                100                 105                 110

Thr Arg Ala His Tyr Asp His Tyr Glu Val Leu Asn Ala Ser Gly Val
            115                 120                 125

Arg Trp Val Val Ile Glu Asp Thr Gly Lys Leu Trp Pro Thr Leu Asp
        130                 135                 140

Leu Lys Val Gly Met Leu Val His Ser Glu Asn Leu Ala Leu Pro Val
145                 150                 155                 160

Glu Lys Ile Tyr Ser Asp Ile Leu Leu Gly Val Ser Pro Leu Ile Leu
                165                 170                 175

Ala Met Val Arg Arg Phe Ser Glu Asp Ala Ala Ala Gly Gly Leu Glu
            180                 185                 190

Asp Leu His Arg Phe Ile Ala Ala Asn Arg Ala Met Val Arg Ala Glu
        195                 200                 205

Leu Ala Gly Leu Pro Gly Val Thr Val Pro Asp Pro Asp Ser Arg Ala
    210                 215                 220

Ser Val Glu Arg Val Ala Ile Asp Asp Leu Thr Gly Thr Gln Val Trp
225                 230                 235                 240

Ala Lys Leu Arg Glu His Asn Val Tyr Ala Leu Pro Cys Arg Pro Phe
                245                 250                 255
```

His Trp Ala Asn Pro Ser Glu Gly Asp His Thr Leu Arg Leu Ala Leu
            260                 265                 270

Ala Arg Ser Thr Asp Pro Leu Ala Gln Ser Val Arg Ala Leu Arg His
        275                 280                 285

Val Leu Lys Gln Arg
    290

<210> SEQ ID NO 36
<211> LENGTH: 1248
<212> TYPE: DNA
<213> ORGANISM: Streptomyces hygroscopicus

<400> SEQUENCE: 36

```
atgacgcctg tcgcagaagg aggactcccg cacggctccg tgccctcgct gtcgcacacg      60
cggcagtggc ggcccggggt cgtgcaggag gtcgccccgg ccggcgtcct cgacctgggc     120
cccggctaca tcgagccggc actcctgccc gtacgcctgc tgcggggcgc gtacgagcaa     180
gcgctggcgg agtacggcgc gcggcgctg ggctacggtc acgacccggg cgcgcagccg      240
ctgcgcgacc ggctgccgc ccgcgccgcc gcggcggacg gcctccctg cgacccggac       300
caggtgctgc tgacctccgg cacgtcccag gccctctatc tgctggcgac ctcgctcgcg     360
gccccgggcg acacagtgct gacggaggag ctctgttacg acctgggaca gcggatattc     420
cgggactgct cactgcggct ccgccaggtc gccatgacg ggtcggggat gctgcccgac      480
gcgctggacc gcgccctgac cgagggcgcg cgagcgggcg cgaaaaccgc tttcgtctac     540
ctcaccccca cccaccacaa ccccacgggc cacacgatgc cgctggcgcg ccgccgcctg     600
ctgctcgaag tggccgcccg gcacgatgtg ctgatcgtgg aggacgacgc ctacacggaa     660
ctgtccctga tccctgaccg cactccccg ccctcgctgg ccgccctggc cggctaccgg     720
cgggtggtgc ggctgtgcag cttctccaag accctcggcc ccggactgcg gctgggctgg     780
ctgctcgccg accgggaact ggccggccgg ctggccacgc acggcctgtt cgtcagcggg     840
ggttcgctca accacaccac ctcgctcgcc gtgagcaccc tgctcgcgag cggcgcgtac     900
gaccgtcatc tcgacgcgtt ccgggcgcag ttgcgtgctc gtagggacgc gctcgtgggc     960
gctctacgcg cgatgctgga cgacggggtg gagctgcgca ccccggaggg cggattcttc    1020
ctgtggctgc gggccgggga cggggccgac gagcgtgagc tgctcgacgg cgccgcccgg    1080
gcgggcgtca ggatcgccgc cggatcgcgc ttcggcacaa cccagggggc cggcttgcgc    1140
ctggccttca gcttcaaccc gcccgcgtta ctggagcagg ccgccaagcg gctgaccacc    1200
gcatggtccg gcagcacgcc ggacctcgag atcggagtga gatcgtga                 1248
```

<210> SEQ ID NO 37
<211> LENGTH: 400
<212> TYPE: PRT
<213> ORGANISM: Streptomyces hygroscopicus

<400> SEQUENCE: 37

Met Thr Pro Val Ala Glu Gly Gly Leu Pro His Gly Ser Val Pro Ser
1               5                  10                  15

Leu Ser His Thr Arg Gln Trp Arg Pro Gly Val Val Gln Glu Val Ala
            20                  25                  30

Pro Ala Gly Val Leu Asp Leu Gly Pro Gly Tyr Ile Glu Pro Ala Leu
        35                  40                  45

Leu Pro Val Arg Leu Leu Arg Gly Ala Tyr Glu Gln Ala Leu Ala Glu
    50                  55                  60

```
Tyr Gly Ala Ala Ala Leu Gly Tyr Gly His Asp Pro Gly Ala Gln Pro
 65                  70                  75                  80

Leu Arg Asp Arg Leu Ala Ala Arg Ala Ala Ala Asp Gly Leu Pro
             85                  90                  95

Cys Asp Pro Asp Gln Val Leu Leu Thr Ser Gly Thr Ser Gln Ala Leu
            100                 105                 110

Tyr Leu Leu Ala Thr Ser Leu Ala Ala Pro Gly Asp Thr Val Leu Thr
        115                 120                 125

Glu Glu Leu Cys Tyr Asp Leu Gly Gln Arg Ile Phe Arg Asp Cys Ser
130                 135                 140

Leu Arg Leu Arg Gln Val Ala Met Asp Gly Ser Gly Met Leu Pro Asp
145                 150                 155                 160

Ala Leu Asp Arg Ala Leu Thr Glu Gly Ala Arg Ala Gly Ala Lys Thr
                165                 170                 175

Ala Phe Val Tyr Leu Thr Pro Thr His His Asn Pro Thr Gly His Thr
            180                 185                 190

Met Pro Leu Ala Arg Arg Leu Leu Glu Val Ala Ala Arg His
        195                 200                 205

Asp Val Leu Ile Val Glu Asp Asp Ala Tyr Thr Glu Leu Ser Leu Ile
            210                 215                 220

Pro Asp Arg Thr Pro Pro Ser Leu Ala Ala Leu Ala Gly Tyr Arg
225                 230                 235                 240

Arg Val Val Arg Leu Cys Ser Phe Ser Lys Thr Leu Gly Pro Gly Leu
                245                 250                 255

Arg Leu Gly Trp Leu Leu Ala Asp Arg Glu Leu Ala Gly Arg Leu Ala
            260                 265                 270

Thr His Gly Leu Phe Val Ser Gly Gly Ser Leu Asn His Thr Thr Ser
        275                 280                 285

Leu Ala Val Ser Thr Leu Leu Ala Ser Gly Ala Tyr Asp Arg His Leu
290                 295                 300

Asp Ala Phe Arg Ala Gln Leu Arg Ala Arg Asp Ala Leu Val Gly
305                 310                 315                 320

Ala Leu Arg Ala Met Leu Asp Asp Gly Val Glu Leu Arg Thr Pro Glu
                325                 330                 335

Gly Gly Phe Phe Leu Trp Leu Arg Ala Gly Asp Gly Asp Glu Arg
            340                 345                 350

Glu Leu Leu Asp Gly Ala Ala Arg Ala Gly Val Arg Ile Ala Ala Gly
        355                 360                 365

Ser Arg Phe Gly Thr Thr Gln Gly Ala Gly Leu Arg Leu Ala Phe Ser
370                 375                 380

Phe Asn Pro Pro Ala Leu Leu Glu Gln Ala Ala Lys Arg Leu Thr Thr
385                 390                 395                 400

<210> SEQ ID NO 38
<211> LENGTH: 1836
<212> TYPE: DNA
<213> ORGANISM: Streptomyces hygroscopicus

<400> SEQUENCE: 38
gtggccggtc caggcagcgc cggtcccgtc gggtacagcc tgccgctctc gccgacgggc      60
gagtcggcga tgctcacacc accgccgtgg cacttctccg gcgaggtcgt catggtcgac     120
taccgcgtcg acccggacgc ggcccgacgg ttcctgccgc cgggcctgga gccgggtgcc     180
gacccgggcg ccgcggcggc ggtgttcgcg acctggcagt ggtgttcgca ggacggagcg     240
```

```
gagctgaccg accccggtcg ctgccagttc ggggagttcc tgatcctgct cagctgcgag    300
ttcgagggcc gtcccatggc gcgctgcccg tacgcctggg tggaccaggc cgtgcccatg    360
atgcgcggct gggtgcaggg gatgcccaag cagttcggcg tgattcacca gagccggccc    420
gtcacggtcg gcaaggcggg ctcccggctg cgcccggcg gtcgtttcga cggcgcgctg    480
tccgtgcacg gacgacgcgt cgtggaggcc tcggtcaccg tggacaggtc gacggaccag    540
ccgccggcgc tgcacgatgt tcccctggcg cacaccctgg tgttcccgga gtgggtgccc    600
tccggcggcg ggccgcgacc acggctggtc gcctccgagg taagcgatgt ggaattctcc    660
ccgatctgga ccggatcggg tgatctcacg ttctttgacg gactgggga tgatttcggg    720
gcgctcgcac cgttggaagt aggtagcagg ccacgtgttc tcgtacgggg agaccttgca    780
cggcggccgc tgctcagcg actactcggt atcagaacga catcagccat gaccacgggg    840
gacaaagtgc tgaggatcca cttcacagtt gaggacatag caaatacgcg catgctggcg    900
accctcgggc cgctggccga gagcgctttc gcgctctatc tgttcggccg taacggcgat    960
gtcgcctttc acgagtggcg tcgcagtgtc cgcgccgaac tcggcaagga cgcggccccgc   1020
ttcacggcct gtcccagca gttccggacc ctggaggaat acctgccgc cttcgccgac    1080
gccttcacgc cggggggcgga ccccgaccag gttccgtccg gcgaggaccg gcgcggcgcc    1140
aggctgctgg ccgacctgtg ccgggtggcc gtgctgccgc actggagcct gatccgcagt    1200
catctcgacg gtgcgcgcga gggctgggc agggtggcca tctcgcacgg tgtcgagcgg    1260
ctgctgggct ccgtgcaccc caaggtccgc tggcgggcgc cggtcctcga actgcggcac    1320
gggcccaacc gcgacatcca tctggacggt cgcgggttgc tgctgtgccc gtcgttcttc    1380
ctgtcggagc agtcctgttc gttcgtgacg gcggtcggca aggacgccat gcccgccctt    1440
gtcttccccg tgaaggcctc gtccagggtg acatctggg gtacctcgga acacgacgag    1500
caggcgctgg gcgcactggt cgggcacacc agggcggccg ccctggaagc gctcgccgag    1560
ggctgctcca cgggcgaact cgccgaccgg ctggggatct cgctggccgg tgccagcaag    1620
catgccgcgg tgctgcgacg atccgggctg gtgaccacct cccgtaaccg caacaccgcg    1680
ctgcacgcgc tcacccctct gggcaccgcc ctgctccgca gcagcgaccg cttcatctcg    1740
ccgcctaccg ccccggtatc gcgcgtgccg gcgcaacgca tgcggccctt gcagctcaac    1800
ggcatcggcc ccggcaccaa ccgggcggcg gtctga                              1836
```

<210> SEQ ID NO 39
<211> LENGTH: 611
<212> TYPE: PRT
<213> ORGANISM: Streptomyces hygroscopicus

<400> SEQUENCE: 39

```
Val Ala Gly Pro Gly Ser Ala Gly Pro Val Gly Tyr Ser Leu Pro Leu
1               5                  10                  15

Ser Pro Thr Gly Glu Ser Ala Met Leu Thr Pro Pro Trp His Phe
            20                  25                  30

Ser Gly Glu Val Val Met Val Asp Tyr Arg Val Asp Pro Asp Ala Ala
        35                  40                  45

Arg Arg Phe Leu Pro Pro Gly Leu Glu Pro Gly Ala Asp Pro Gly Ala
    50                  55                  60

Ala Ala Ala Val Phe Ala Thr Trp Gln Trp Cys Ser Gln Asp Gly Ala
65                  70                  75                  80

Glu Leu Thr Asp Pro Gly Arg Cys Gln Phe Gly Glu Phe Leu Ile Leu
                85                  90                  95
```

-continued

```
Leu Ser Cys Glu Phe Glu Gly Arg Pro Met Ala Arg Cys Pro Tyr Ala
            100                 105                 110

Trp Val Asp Gln Ala Val Pro Met Met Arg Gly Trp Val Gln Gly Met
        115                 120                 125

Pro Lys Gln Phe Gly Val Ile His Gln Ser Arg Pro Val Thr Val Gly
    130                 135                 140

Lys Ala Gly Ser Arg Leu Ala Pro Gly Gly Arg Phe Asp Gly Ala Leu
145                 150                 155                 160

Ser Val His Gly Arg Arg Val Glu Ala Ser Val Thr Val Asp Arg
            165                 170                 175

Ser Thr Asp Gln Pro Pro Ala Leu His Asp Val Pro Leu Ala His Thr
        180                 185                 190

Leu Val Phe Pro Glu Trp Val Ser Gly Gly Pro Arg Pro Arg
            195                 200                 205

Leu Val Ala Ser Glu Val Ser Asp Val Glu Phe Ser Pro Ile Trp Thr
        210                 215                 220

Gly Ser Gly Asp Leu Thr Phe Phe Asp Gly Leu Gly Asp Asp Phe Gly
225                 230                 235                 240

Ala Leu Ala Pro Leu Glu Val Gly Ser Arg Pro Arg Val Leu Val Arg
            245                 250                 255

Gly Asp Leu Ala Arg Arg Pro Ala Ala Gln Arg Leu Leu Gly Ile Arg
        260                 265                 270

Thr Thr Ser Ala Met Thr Thr Gly Asp Lys Val Leu Arg Ile His Phe
    275                 280                 285

Thr Val Glu Asp Ile Ala Asn Thr Arg Met Leu Ala Thr Leu Gly Pro
290                 295                 300

Leu Ala Glu Ser Ala Phe Ala Leu Tyr Leu Phe Gly Arg Asn Gly Asp
305                 310                 315                 320

Val Ala Phe His Glu Trp Arg Arg Ser Val Arg Ala Glu Leu Gly Lys
            325                 330                 335

Asp Ala Ala Arg Phe Thr Ala Leu Ser Gln Gln Phe Arg Thr Leu Glu
        340                 345                 350

Glu Leu Pro Ala Ala Phe Ala Asp Ala Phe Thr Pro Gly Ala Asp Pro
    355                 360                 365

Asp Gln Val Pro Ser Gly Glu Asp Arg Gly Ala Arg Leu Leu Ala
    370                 375                 380

Asp Leu Cys Arg Val Ala Val Leu Pro His Trp Ser Leu Ile Arg Ser
385                 390                 395                 400

His Leu Asp Gly Ala Arg Glu Gly Trp Gly Arg Val Ala Ile Ser His
            405                 410                 415

Gly Val Glu Arg Leu Leu Gly Ser Val His Pro Lys Val Arg Trp Arg
        420                 425                 430

Ala Pro Val Leu Glu Leu Arg His Gly Pro Asn Arg Asp Ile His Leu
    435                 440                 445

Asp Gly Arg Gly Leu Leu Leu Cys Pro Ser Phe Phe Leu Ser Glu Gln
    450                 455                 460

Ser Cys Ser Phe Val Thr Ala Val Gly Lys Asp Ala Met Pro Ala Leu
465                 470                 475                 480

Val Phe Pro Val Lys Ala Ser Ser Arg Val Asp Ile Trp Gly Thr Ser
            485                 490                 495

Glu His Asp Glu Gln Ala Leu Gly Ala Leu Val Gly His Thr Arg Ala
        500                 505                 510
```

```
Ala Ala Leu Glu Ala Leu Ala Glu Gly Cys Ser Thr Gly Glu Leu Ala
        515                 520                 525

Asp Arg Leu Gly Ile Ser Leu Ala Gly Ala Ser Lys His Ala Ala Val
        530                 535                 540

Leu Arg Arg Ser Gly Leu Val Thr Thr Ser Arg Asn Arg Asn Thr Ala
545                 550                 555                 560

Leu His Ala Leu Thr Pro Leu Gly Thr Ala Leu Leu Arg Ser Ser Asp
                565                 570                 575

Arg Phe Ile Ser Pro Pro Thr Ala Pro Val Ser Arg Val Pro Ala Gln
                580                 585                 590

Arg Met Arg Pro Leu Gln Leu Asn Gly Ile Gly Pro Gly Thr Asn Arg
        595                 600                 605

Ala Ala Val
    610

<210> SEQ ID NO 40
<211> LENGTH: 216
<212> TYPE: DNA
<213> ORGANISM: Streptomyces hygroscopicus

<400> SEQUENCE: 40
gtgggcacaa accccttcga cgaccccgac ggccggtatc tggtgctggt caacgaggaa      60
gaccagcatt cactctggcc ggctttcgcc gaggtgcccc agggctggac ggtggcgctc     120
gcggaaaccg accgtcagtc cgcgctcgac ttcatcaccg agcactggac cgacatgcgg     180
ccgcgcagcc tggtgcgggc gatggaagag gcttag                               216

<210> SEQ ID NO 41
<211> LENGTH: 71
<212> TYPE: PRT
<213> ORGANISM: Streptomyces hygroscopicus

<400> SEQUENCE: 41

Val Gly Thr Asn Pro Phe Asp Asp Pro Asp Gly Arg Tyr Leu Val Leu
1               5                   10                  15

Val Asn Glu Glu Asp Gln His Ser Leu Trp Pro Ala Phe Ala Glu Val
                20                  25                  30

Pro Gln Gly Trp Thr Val Ala Leu Ala Glu Thr Asp Arg Gln Ser Ala
            35                  40                  45

Leu Asp Phe Ile Thr Glu His Trp Thr Asp Met Arg Pro Arg Ser Leu
        50                  55                  60

Val Arg Ala Met Glu Glu Ala
65                  70

<210> SEQ ID NO 42
<211> LENGTH: 1454
<212> TYPE: DNA
<213> ORGANISM: Streptomyces hygroscopicus

<400> SEQUENCE: 42
cagagggcgt tcaggtcgac ggcggaggcg agggccaggt agccggcgtc gctggggtgg      60
aggccgtcct gggagatgta gccggggcgg gggcggttgg ggttcgcggg gtcggtcagg     120
acgcggtcgg cgtcgaggac ggcgtcgtag gtgtggctgg tgcggatcca gtggttgagc     180
tgccggcgga tcttgtcacc ggcggggtg gtgaagggga agacggcgct cctgaggggg      240
aggatcgtca caccgatggc cttgataccg cggcgtggg ccgcgcggac cagggcgcgg       300
tggccgtcga tgagctgttg ggcggtcacc gggggcggt tcctggtgca gggtcgtcc       360
```

-continued

```
tgctgggact gggcgaggtc attggcgccg aggtggatga agacggtgcg cagggcggcg      420
cgatcgcgca gttccttggc gaagcgggcg gtgcccttct cgccgaagca ggggggaatcg     480
tgcagcaggg ggtcacccgc caggccggcg ttggtcattc cctggggggcg gccggcggcg     540
atgaggcgtt cggcgagttt gtcggagaag cggttgtcgg tgtcggggct ggtgccgacg     600
ccgtccatga gggagtcgcc gaagaccatg agggagtcgg ccgaacgggg cggctcctgg     660
gtcacatcga cggccgtcag gtagtaccag gcgtgcgagg cacggcggtt gaagtcatcg     720
gcggcggggc tgcgtagccg gtcgccgggg gcgcggtagg acgtggccgt ggtgaagcgg     780
tgcatggtgg ccgggccggt gggggcggtg aagcgcaggg tgacggtgag tttttcgagg     840
ttggcggtcg gcatggccac cgcgtcgctg acggtgtcgc ggcccgcggg gatggtgagg     900
gcgggcgcat ggcggaaggt gagggtgcgt acggtgccgg ggcgcgcctt ggcctcgccg     960
tcggacctgg cgacggtggc gccggcgatg tggagggggct tggtgccgta ggcgttggag    1020
aggcggatac ggagctcggg gccgccgacg ctgagccgga tcacctggcg cagggtctcg     1080
ttcttgaatc cctgccggga ccagttcggg gtgtcctccg tggcctcgtt cgtcgcctgc     1140
tgcatggcgg ctccccaggt ggctgtccac tgggggggagt gggggggcggc ggggggcggcc   1200
ttctcgctcc tgagggacgg gcgggcgggg gcgaacgccc cggtcagcgc cgcggtcagg     1260
gtcacggcca gggccacgga cagcgtcatg acgatcgtcg cggggagcga gcgcgggctc     1320
cccttcgtgg tgcggccggg tgcgggccgg ccggcctcgg gtgcgtcggc cgtgtgctgc     1380
tcggccgtgt gcgggtcggt ttcgtgccgg tcggtttcgg gtcggccggc tttgtgccgg     1440
ggccacagtc gcat                                                      1454
```

<210> SEQ ID NO 43
<211> LENGTH: 484
<212> TYPE: PRT
<213> ORGANISM: Streptomyces hygroscopicus

<400> SEQUENCE: 43

```
Met Arg Leu Trp Pro Arg His Lys Ala Gly Arg Pro Glu Thr Asp Arg
1               5                   10                  15

His Glu Thr Asp Pro His Thr Ala Glu Gln His Thr Ala Asp Ala Pro
            20                  25                  30 lu Ala Gly Arg Pro Ala Pro Gly Arg Thr Thr Lys Gly Ser Pro Arg
        35                  40                  45 er Leu Pro Ala Thr Ile Val Met Thr Leu Ser Val Ala Leu Ala Val
    50                  55                  60 hr Leu Thr Ala Ala Leu Thr Gly Ala Phe Ala Pro Ala Arg Pro Ser
5                   70                  75                  80 eu Arg Ser Glu Lys Ala Ala Pro Ala Ala Pro His Ser Pro Gln Trp
                85                  90                  95 hr Ala Thr Trp Gly Ala Ala Met Gln Gln Ala Thr Asn Glu Ala Thr
            100                 105                 110 lu Asp Thr Pro Asn Trp Ser Arg Gln Gly Phe Lys Asn Glu Thr Leu
        115                 120                 125 rg Gln Val Ile Arg Leu Ser Val Gly Gly Pro Glu Leu Arg Ile Arg
    130                 135                 140 eu Ser Asn Ala Tyr Gly Thr Lys Pro Leu His Ile Ala Gly Ala Thr
45                  150                 155                 160 al Ala Arg Ser Asp Gly Glu Ala Lys Ala Arg Pro Gly Thr Val Arg
                165                 170                 175
```

```
hr Leu Thr Phe Arg His Ala Pro Ala Leu Thr Ile Pro Ala Gly Arg
            180                 185                 190 sp Thr Val Ser Asp Ala Val Ala Met Pro Thr Ala Asn Leu Glu Lys
            195                 200             205 eu Thr Val Thr Leu Arg Phe Thr Ala Pro Thr Gly Pro Ala Thr Met
            210                 215                 220 is Arg Phe Thr Thr Ala Thr Ser Tyr Arg Ala Pro Gly Asp Arg Leu
25              230                 235                 240 rg Ser Pro Ala Ala Asp Asp Phe Asn Arg Arg Ala Ser His Ala Trp
                245                 250                 255 yr Tyr Leu Thr Ala Val Asp Val Thr Gln Glu Pro Pro Arg Ser Ala
            260                 265                 270 sp Ser Leu Met Val Phe Gly Asp Ser Leu Met Asp Gly Val Gly Thr
            275                 280                 285 er Pro Asp Thr Asp Asn Arg Phe Ser Asp Lys Leu Ala Glu Arg Leu
            290                 295                 300 le Ala Ala Gly Arg Pro Gln Gly Met Thr Asn Ala Gly Leu Ala Gly
05              310                 315                 320 sp Pro Leu Leu His Asp Ser Pro Cys Phe Gly Glu Lys Gly Thr Ala
                325                 330                 335 rg Phe Ala Lys Glu Leu Arg Asp Arg Ala Ala Leu Arg Thr Val Phe
            340                 345                 350 le His Leu Gly Ala Asn Asp Leu Ala Gln Ser Gln Gln Asp Asp Pro
            355                 360                 365 ys Thr Arg Asn Arg Pro Pro Val Thr Ala Gln Gln Leu Ile Asp Gly
            370                 375                 380 is Arg Ala Leu Val Arg Ala Ala His Ala Arg Gly Ile Lys Ala Ile
85              390                 395                 400 ly Val Thr Ile Leu Pro Leu Arg Ser Ala Val Phe Pro Phe Thr Thr
                405                 410                 415 ro Ala Gly Asp Lys Ile Arg Arg Gln Leu Asn His Trp Ile Arg Thr
            420                 425                 430 er His Thr Tyr Asp Ala Val Leu Asp Ala Asp Arg Val Leu Thr Asp
            435                 440                 445 ro Ala Asn Pro Asn Arg Pro Arg Pro Gly Tyr Ile Ser Gln Asp Gly
            450                 455                 460 eu His Pro Ser Asp Ala Gly Tyr Leu Ala Leu Ala Ser Ala Val Asp
65              470                 475                 480 eu Asn Ala Leu

<210> SEQ ID NO 44
<211> LENGTH: 1713
<212> TYPE: DNA
<213> ORGANISM: Streptomyces hygroscopicus

<400> SEQUENCE: 44
gtggggtcga cggcggccgg gccgcccagg gcttcggcga acggccgctc caggcacggg    60
tggtgtgagg caatgatgcg catgctcacc ggtcttgcgg tggccgactt ccgcgaccgg   120
gtacgccggc ccgcgtatgt cgtgatcctg gccgcggccg tcgccctcgg ttacgtggcg   180
gtgcccgact cggacgccaa atggatgatc atgcagatcg tgatcaccg cgggatctac    240 aacagcgcct acgtcggcat ggtgacggcc ctggccagcg tctgtggat cacccctcggc   300 ggcttctaca tcgtccgcaa ctccatcgaa cgcgaccgca gcacccgcgt cggccagctg   360
```

-continued

```
ctcgccgcca ccccgctgcg caccaccgcg tacatgctcg gcaagttcct cagcaacctc    420
atgctgctgt cctccatgct cgtggtgctc gcgctcaccg ccctggtcat gcaactggcc    480
cgcggcgagt cgcacgacat cgacctgatc gccctctggc agcccttcct cctcatcgcg    540
ctgccgctgg tcgcgctgac cgccgccctc gcgctcctct tcgaatcgct gccgctgctg    600
cgcaccggcc tgggcaacat cctgtggttc tgcatctgga tggtcgtctc gacggccggc    660
cagggccccg tctgccct cgacggcatc ggcgtcaaca gcgtcgtccg gtcgatgtat    720
gacgacatgg tcgcccagca catcgatgtc accggcgcgt tcagcctcgg tctgacctac    780
ctcgacaagc ccctcgggct cttcacctgg gacggcttca cgcccaccgc cggctatgtc    840
ctcgccgggg tgacgctgct gctgatcgcc gtcgtgatcg ccatgctccc cgcgctgtgg    900
ttcggccgct tcgaccccgc gcgaacctgg ctgggccagg ggcgcacccc cgagcaggcc    960
ccggccgacg tgtcgtcca gccggtcttc atcgacgagg tcggcccggg gacgcctccg    1020
ctgtccgttc agggccatgg gggagcttcc ccgtcccggc ccaccgtcgc cacgctgctg    1080
cgcacccgcc cggagccggg cgccgtgacc ctgcgcgtct gggccggcga ggtccgcatc    1140
ctgctgcaag gtgtgcgctg gtggtggtgg accggtgccg cattcctcat gatcgccgcg    1200
ctctcctccc cggggatcca cggcatcatc gcgcgtgatgc tgccgctgtc ctggatctgg    1260
ccggtgctga tctggtcgcg gctgggcacc cagcgccacg agtaccacgt cgacggcatg    1320
ctcggcgcct accccgcggt gcgccgccgg gtcttcgccg aatgggccgc gggcctgacc    1380
atcaccgccg tggccggcat cggtccctg atccgcctgg tggccgccgc cgactggttc    1440
ggtctggccg gctgggtcgg cggggccctg ttcatcccgt ccctggccct caccctgggc    1500
acgctcagcc gtaccatcg cctcttccag gcggtctacc tgccgctctg gtacagcgtc    1560
gccaacggac tgccgatctt cgacttcatg ggcgcgctgc gcgacagcag cgaactggcc    1620
gccgtgcagc gtcggtgac cgtcgtggtt ccgcggccc tgatggccat cgtcttcatg    1680
accggcgtac tccgccgctt cggccgcgac tga                                  1713
```

<210> SEQ ID NO 45  
<211> LENGTH: 570  
<212> TYPE: PRT  
<213> ORGANISM: Streptomyces hygroscopicus

<400> SEQUENCE: 45

```
Val Gly Ser Thr Ala Ala Gly Pro Pro Arg Ala Ser Ala Asn Gly Arg
1               5                   10                  15

Ser Arg His Gly Trp Cys Glu Ala Met Met Arg Met Leu Thr Gly Leu
            20                  25                  30

Ala Val Ala Asp Phe Arg Asp Arg Val Arg Arg Pro Ala Tyr Val Val
        35                  40                  45

Ile Leu Ala Ala Ala Val Ala Leu Gly Tyr Val Ala Val Pro Asp Ser
    50                  55                  60

Asp Ala Lys Trp Met Ile Met Gln Ile Gly Asp His Arg Gly Ile Tyr
65                  70                  75                  80

Asn Ser Ala Tyr Val Gly Met Val Thr Ala Leu Ala Ser Gly Leu Trp
                85                  90                  95

Ile Thr Leu Gly Gly Phe Tyr Ile Val Arg Asn Ser Ile Glu Arg Asp
            100                 105                 110

Arg Ser Thr Arg Val Gly Gln Leu Leu Ala Ala Thr Pro Leu Arg Thr
        115                 120                 125
```

-continued

```
Thr Ala Tyr Met Leu Gly Lys Phe Leu Ser Asn Leu Met Leu Leu Ser
        130                 135                 140

Ser Met Leu Val Val Leu Ala Leu Thr Ala Leu Val Met Gln Leu Ala
145                 150                 155                 160

Arg Gly Glu Ser His Asp Ile Asp Leu Ile Ala Leu Trp Gln Pro Phe
                165                 170                 175

Leu Leu Ile Ala Leu Pro Leu Val Ala Leu Thr Ala Ala Leu Ala Leu
                180                 185                 190

Leu Phe Glu Ser Leu Pro Leu Leu Arg Thr Gly Leu Gly Asn Ile Leu
            195                 200                 205

Trp Phe Cys Ile Trp Met Val Val Ser Thr Ala Gly Gln Gly Pro Gly
        210                 215                 220

Leu Pro Leu Asp Gly Ile Gly Val Asn Ser Val Val Arg Ser Met Tyr
225                 230                 235                 240

Asp Asp Met Val Ala Gln His Ile Asp Val Thr Gly Ala Phe Ser Leu
                245                 250                 255

Gly Leu Thr Tyr Leu Asp Lys Pro Leu Gly Leu Phe Thr Trp Asp Gly
                260                 265                 270

Phe Thr Pro Thr Ala Gly Tyr Val Leu Gly Arg Val Thr Leu Leu Leu
            275                 280                 285

Ile Ala Val Val Ile Ala Met Leu Pro Ala Leu Trp Phe Gly Arg Phe
        290                 295                 300

Asp Pro Ala Arg Thr Trp Leu Gly Gln Gly Arg Thr Pro Glu Gln Ala
305                 310                 315                 320

Pro Ala Asp Gly Val Val Gln Pro Val Phe Ile Asp Glu Val Gly Pro
                325                 330                 335

Gly Thr Pro Pro Leu Ser Val Gln Gly His Gly Gly Ala Ser Pro Ser
                340                 345                 350

Arg Pro Thr Val Ala Thr Leu Leu Arg Thr Arg Pro Glu Pro Gly Ala
            355                 360                 365

Val Thr Leu Arg Val Trp Ala Gly Glu Val Arg Ile Leu Leu Gln Gly
        370                 375                 380

Val Arg Trp Trp Trp Thr Gly Ala Ala Phe Leu Met Ile Ala Ala
385                 390                 395                 400

Leu Ser Ser Pro Gly Ile His Gly Ile Ile Arg Val Met Leu Pro Leu
                405                 410                 415

Ser Trp Ile Trp Pro Val Leu Ile Trp Ser Arg Leu Gly Thr Gln Arg
                420                 425                 430

His Glu Tyr His Val Asp Gly Met Leu Gly Ala Tyr Pro Ala Val Arg
            435                 440                 445

Arg Arg Val Phe Ala Glu Trp Ala Ala Gly Leu Thr Ile Thr Ala Val
450                 455                 460

Ala Gly Ile Gly Pro Leu Ile Arg Leu Val Ala Ala Asp Trp Phe
465                 470                 475                 480

Gly Leu Ala Gly Trp Val Gly Gly Ala Leu Phe Ile Pro Ser Leu Ala
                485                 490                 495

Leu Thr Leu Gly Thr Leu Ser Arg Thr His Arg Leu Phe Gln Ala Val
            500                 505                 510

Tyr Leu Pro Leu Trp Tyr Ser Val Ala Asn Gly Leu Pro Ile Phe Asp
            515                 520                 525

Phe Met Gly Ala Leu Arg Asp Ser Ser Glu Leu Ala Ala Val Gln Pro
530                 535                 540

Ser Val Thr Val Val Val Ser Ala Ala Leu Met Ala Ile Val Phe Met
```

```
                545                 550                 555                 560

Thr Gly Val Leu Arg Arg Phe Gly Arg Asp
                565                 570

<210> SEQ ID NO 46
<211> LENGTH: 855
<212> TYPE: DNA
<213> ORGANISM: Streptomyces hygroscopicus

<400> SEQUENCE: 46
atgcgtctgg aacccggcat gctcggcctg ctgggcccca acggcgccgg caagtcgtcc      60
ctcatgcgga tcgcctccac ggtcacccgg cccaccagcg gaaaggtcct cttccacgga     120
gaggacgcgg tcgccaagcc caacgcgctg cgccgggccc tcggttacct cccgcaggac     180
ttcggcgtct acccgaacct gacctcccgc gagttcctca ggtatctggc ggcggccaag     240
ggcgtctcgg ccaagaccgc caaggcccgt atcgatgagc tcctggagct cgtcaacctc     300
accgaagcgg tcaagcgtcc cctgggcaag tactccggcg gcatgctgcg ccgggtcggc     360
atcgcccagg tgctgctcgc cgaccccgca gtgatcatcg tggacgagcc gaccgcgggg     420
ctggaccccg aggagcgggt caggttccgc aatctgctca gcgatctggc ggccgacaag     480
gtcgtgatgc tctccaccca catcgtctcc gacgtcgagt cggtggcctc cgacatcgcg     540
gtgatggccg gcggccggct gcagcgccgc ggcaccccg aggacctgct cgcgctcggtg     600 gacggccagg tgtgggaggt gctggtcgac ccctcgtccg tagcggcggt gcaggcgcag     660
tacaccgtca gccgcctggt ccgcacgacc gagggcgtcc gtatccggct gctctcgcgc     720
gagctgccgt acgagggcgc cgtccagctg acgcccgacc tggaagacgc ctacctcgcc     780
atcatccgtg gggtcgacgg cggccgggcc gcccagggct cggcgaacg gccgctccag     840 gcacgggtgg tgtga                                                      855

<210> SEQ ID NO 47
<211> LENGTH: 284
<212> TYPE: PRT
<213> ORGANISM: Streptomyces hygroscopicus

<400> SEQUENCE: 47

Met Arg Leu Glu Pro Gly Met Leu Gly Leu Leu Gly Pro Asn Gly Ala
1               5                  10                  15

Gly Lys Ser Ser Leu Met Arg Ile Ala Ser Thr Val Thr Arg Pro Thr
            20                  25                  30

Ser Gly Lys Val Leu Phe His Gly Glu Asp Ala Val Ala Lys Pro Asn
        35                  40                  45

Ala Leu Arg Arg Ala Leu Gly Tyr Leu Pro Gln Asp Phe Gly Val Tyr
    50                  55                  60

Pro Asn Leu Thr Ser Arg Glu Phe Leu Arg Tyr Leu Ala Ala Ala Lys
65                  70                  75                  80

Gly Val Ser Ala Lys Thr Ala Lys Ala Arg Ile Asp Glu Leu Leu Glu
                85                  90                  95

Leu Val Asn Leu Thr Glu Ala Val Lys Arg Pro Leu Gly Lys Tyr Ser
            100                 105                 110

Gly Gly Met Leu Arg Arg Val Gly Ile Ala Gln Val Leu Leu Ala Asp
        115                 120                 125

Pro Gln Val Ile Ile Val Asp Glu Pro Thr Ala Gly Leu Asp Pro Glu
    130                 135                 140

Glu Arg Val Arg Phe Arg Asn Leu Leu Ser Asp Leu Ala Ala Asp Lys
```

```
                145                 150                 155                 160
Val Val Met Leu Ser Thr His Ile Val Ser Asp Val Glu Ser Val Ala
                    165                 170                 175

Ser Asp Ile Ala Val Met Ala Gly Gly Arg Leu Gln Arg Arg Gly Thr
                180                 185                 190

Pro Glu Asp Leu Leu Arg Ser Val Asp Gly Gln Val Trp Glu Val Leu
                195                 200                 205

Val Asp Pro Ser Ser Val Ala Ala Val Gln Ala Gln Tyr Thr Val Ser
                210                 215                 220

Arg Leu Val Arg Thr Thr Glu Gly Val Arg Ile Arg Leu Leu Ser Arg
225                 230                 235                 240

Glu Leu Pro Tyr Glu Gly Ala Val Gln Leu Thr Pro Asp Leu Glu Asp
                245                 250                 255

Ala Tyr Leu Ala Ile Ile Arg Gly Val Asp Gly Arg Ala Ala Gln
                260                 265                 270

Gly Phe Gly Glu Arg Pro Leu Gln Ala Arg Val Val
                275                 280

<210> SEQ ID NO 48
<211> LENGTH: 417
<212> TYPE: DNA
<213> ORGANISM: Streptomyces hygroscopicus

<400> SEQUENCE: 48
gtgactctgg aggaaccgat gttctcaggc accatctcga agcggcccgc cacactcgtc    60
gtcgcggtgg cggccgtcgc cgccaccctc ggcctctccg gctgctccgt ggacgcctcg   120
aaggcgaagc ccgaatcgaa gtcgttcacg tactcgggca gtccctgaa ggtgacgacg    180 cacgaggtcg ccaccaaggt ggtcgccgcc gaccgcaagg acatcaaggt cacccgctgg   240
ttcgactcgg ccgcgggcac cgagcacctg aagtggaccc tcaagggcga caccctggac   300
atcgacgccg gctgcagcgg tatcgcgatc tgcgacgcca agttcaaggt cgaggtcccc   360
aagggcatcg cggtgaccaa ggacggcgag aagaccgacc tgaccgggaa gagctga      417

<210> SEQ ID NO 49
<211> LENGTH: 138
<212> TYPE: PRT
<213> ORGANISM: Streptomyces hygroscopicus

<400> SEQUENCE: 49

Val Thr Leu Glu Glu Pro Met Phe Ser Gly Thr Ile Ser Lys Arg Pro
1               5                   10                  15

Ala Thr Leu Val Val Ala Val Ala Ala Val Ala Ala Thr Leu Gly Leu
                20                  25                  30

Ser Gly Cys Ser Val Asp Ala Ser Lys Ala Lys Pro Glu Ser Lys Ser
            35                  40                  45

Phe Thr Tyr Ser Gly Lys Ser Leu Lys Val Thr Thr His Glu Val Ala
        50                  55                  60

Thr Lys Val Val Ala Ala Asp Arg Lys Asp Ile Lys Val Thr Arg Trp
65                  70                  75                  80

Phe Asp Ser Ala Ala Gly Thr Glu His Leu Lys Trp Thr Leu Lys Gly
                85                  90                  95

Asp Thr Leu Asp Ile Asp Ala Gly Cys Ser Gly Ile Ala Ile Cys Asp
                100                 105                 110

Ala Lys Phe Lys Val Glu Val Pro Lys Gly Ile Ala Val Thr Lys Asp
            115                 120                 125
```

```
Gly Glu Lys Thr Asp Leu Thr Gly Lys Ser
    130                 135
```

<210> SEQ ID NO 50
<211> LENGTH: 1191
<212> TYPE: DNA
<213> ORGANISM: Streptomyces hygroscopicus

<400> SEQUENCE: 50

```
gtgcgtagcc tcgccctcat ggattacgac gttcctcccc ggcaaaagcg ccgccggtgg      60
tgcggggtgg ccgcggcaat gatgctcgcc cccgccgtca tagcgccacc gagcgcctat     120
ctgctggcgg tcatggccgc attgacgctg gccgtatcga tacttgcctg gccgaccggc     180
cggatctccc tggcccaggc ggcgggcggc gtcgcgctgc tctccctcgc cgcggacgtc     240
ggctacttcg gcagcccgg cctggtgatc tctggtacc cgttcgagac ggtcgcgctg      300
ctcgttctcc tggagcgggt ggtacgtcat gtgcccagcc ccgggtggg catcgtcgcc     360
ccgctgaccg gcgcagccgt catcctgctg ccctgcgct tcaccctgca cgcccccacc     420
gccgggctca aggaatcggt cttcgcggcc ttgctggccc tgatcccggc ggcctgcgcg     480
acgggtgtgg ggctctatct gcggtcgctg acaaccgcc gggcgtatgc cgtggtgctg     540
gcgcgccgtg aacagcgcct cgaagtcgcc cgcgatctgc atgacttcgt cgcccacgag     600
gtgaccggca tcgttctgga ggcccaggcc gcccaagtca gcgaggacgc cgggcccgag     660
gagcaccgcg cccttctgca gcgcatcgag aaggccgggc tacggcgct ggactccatg      720
gaccagacgg tgacgacgct gcgcgaggcg gacggccgca agtggggcga ccgccgcccc     780
acccggctct acggcttggc cgacctcccc gagctcgtcg gccgcttctc ctccatggcc     840
gccgccgagg tggcgctgtc cctggaggac gaggtcgccg caccctctc gcgggaggcc     900
gaggacaccg cgtaccgggt ggtacttgaa tcgttgacca atgtccgtcg gcatgcgccg     960
caggccggcc gggtccaggt gttcgccgga cggaccgccg accgggccgt ggaggtctcg    1020
gtcgccgaca cgcagggcc gggggcgtcc gccggcaccc gcagggcgg cggtacgggc    1080
ctggcgggcc tcggcgaacg cgtcagcgcc ctggcggct ccctggaggc gggcccgtac    1140
gagaacgggt ggcgggtcag gtgcctgctg ccggcgcccg ccatccgctg a            1191
```

<210> SEQ ID NO 51
<211> LENGTH: 396
<212> TYPE: PRT
<213> ORGANISM: Streptomyces hygroscopicus

<400> SEQUENCE: 51

```
Val Arg Ser Leu Ala Leu Met Asp Tyr Asp Val Pro Pro Arg Gln Lys
1               5                   10                  15

Arg Arg Arg Trp Cys Gly Val Ala Ala Ala Met Met Leu Ala Pro Ala
            20                  25                  30

Val Ile Ala Pro Pro Ser Ala Tyr Leu Leu Ala Val Met Ala Ala Leu
        35                  40                  45

Thr Leu Ala Val Ser Ile Leu Ala Trp Pro Thr Gly Arg Ile Ser Leu
    50                  55                  60

Ala Gln Ala Ala Gly Gly Val Ala Leu Leu Ser Leu Ala Ala Asp Val
65                  70                  75                  80

Gly Tyr Phe Gly Gln Pro Gly Leu Val Ile Leu Trp Tyr Pro Phe Glu
                85                  90                  95

Thr Val Ala Leu Leu Val Leu Leu Glu Arg Val Val Arg His Val Pro
```

```
                100             105              110
Ser Pro Arg Val Gly Ile Val Ala Pro Leu Thr Gly Ala Ala Val Ile
        115                 120                 125

Leu Leu Pro Leu Arg Phe Thr Leu His Ala Pro Thr Ala Gly Leu Lys
    130                 135                 140

Glu Ser Val Phe Ala Ala Leu Leu Ala Leu Ile Pro Ala Ala Cys Ala
145                 150                 155                 160

Thr Gly Val Gly Leu Tyr Leu Arg Ser Leu Asp Asn Arg Arg Ala Tyr
                165                 170                 175

Ala Val Val Leu Ala Arg Arg Glu Gln Arg Leu Glu Val Ala Arg Asp
            180                 185                 190

Leu His Asp Phe Val Ala His Glu Val Thr Gly Ile Val Leu Glu Ala
        195                 200                 205

Gln Ala Ala Gln Val Ser Glu Asp Ala Gly Pro Glu Glu His Arg Ala
    210                 215                 220

Leu Leu Gln Arg Ile Glu Lys Ala Gly Leu Arg Ala Leu Asp Ser Met
225                 230                 235                 240

Asp Gln Thr Val Thr Thr Leu Arg Glu Ala Asp Gly Arg Lys Trp Gly
                245                 250                 255

Glu Pro Pro Pro Thr Arg Leu Tyr Gly Leu Ala Asp Leu Pro Glu Leu
            260                 265                 270

Val Gly Arg Phe Ser Ser Met Ala Ala Glu Val Ala Leu Ser Leu
        275                 280                 285

Glu Asp Glu Val Ala Gly Thr Leu Ser Arg Glu Ala Glu Asp Thr Ala
    290                 295                 300

Tyr Arg Val Val Leu Glu Ser Leu Thr Asn Val Arg Arg His Ala Pro
305                 310                 315                 320

Gln Ala Gly Arg Val Gln Val Phe Ala Gly Arg Thr Ala Asp Arg Ala
                325                 330                 335

Val Glu Val Ser Val Ala Asp Asn Ala Gly Pro Gly Ala Ser Ala Gly
            340                 345                 350

Thr Arg Gln Gly Gly Gly Thr Gly Leu Ala Gly Leu Gly Glu Arg Val
        355                 360                 365

Ser Ala Leu Gly Gly Ser Leu Glu Ala Gly Pro Tyr Glu Asn Gly Trp
    370                 375                 380

Arg Val Arg Cys Leu Leu Pro Ala Pro Ala Ile Arg
385                 390                 395

<210> SEQ ID NO 52
<211> LENGTH: 681
<212> TYPE: DNA
<213> ORGANISM: Streptomyces hygroscopicus

<400> SEQUENCE: 52
gaattcctgc ccgtgactat tcgcttgctg atcgccgacg accaggagat ggtccgccgc      60
ggaatacgcc gcatcgtgga gagccagccc gacatggaag tggtcggcga ggcggcaaac     120
ggcgtggacg cggtggagat ggggcgcacg ctcaaacccg atgtggcgct ggtcgacatc     180
cggatgccgc ggatggacgg cctggaggtg acccgcctgc tggccgaccc cgccgcggcc     240
aacccggtcc gggtcgtcgt ggtgacgacc ttcgacctgg acgagtacgt gtaccccgcg     300
ctgcgcttcg gcgcctcggg gttcctgctc aagcgctcgg ggccgacgct gctggtcgag     360
gcggtccggg cggcgatggc cggcgacagc ctgatcagcc cgtcgatcac tgtccggctg     420
ctccagcatg tcaccggccc cacgaccggc cgccgccccc gccgccgtga ctcggtgctg     480
```

-continued

```
accgagcggg aggtggagat cgccgggaag gtcgccgagg gcaagaccaa ttccgatatc    540
gcccgcgagt tgttcatctc cgcgggcacg gtcaagaccc atgtcgcgag cattcagcga    600
aagctacagg tacgcaatcg cgtcggggtc gcggtgcggg cctgggagct cggatatgcc    660
accgggcaga ccccggggtg a                                              681
```

<210> SEQ ID NO 53
<211> LENGTH: 226
<212> TYPE: PRT
<213> ORGANISM: Streptomyces hygroscopicus

<400> SEQUENCE: 53

```
Glu Phe Leu Pro Val Thr Ile Arg Leu Leu Ile Ala Asp Asp Gln Glu
1               5                   10                  15

Met Val Arg Arg Gly Ile Arg Arg Ile Val Glu Ser Gln Pro Asp Met
                20                  25                  30

Glu Val Val Gly Glu Ala Ala Asn Gly Val Asp Ala Val Glu Met Gly
            35                  40                  45

Arg Thr Leu Lys Pro Asp Val Ala Leu Val Asp Ile Arg Met Pro Arg
        50                  55                  60

Met Asp Gly Leu Glu Val Thr Arg Leu Leu Ala Asp Pro Ala Ala Ala
65                  70                  75                  80

Asn Pro Val Arg Val Val Val Thr Thr Phe Asp Leu Asp Glu Tyr
                85                  90                  95

Val Tyr Pro Ala Leu Arg Phe Gly Ala Ser Gly Phe Leu Leu Lys Arg
            100                 105                 110

Ser Gly Pro Thr Leu Leu Val Glu Ala Val Arg Ala Ala Met Ala Gly
        115                 120                 125

Asp Ser Leu Ile Ser Pro Ser Ile Thr Val Arg Leu Leu Gln His Val
130                 135                 140

Thr Gly Pro Thr Thr Gly Arg Arg Pro Arg Arg Arg Asp Ser Val Leu
145                 150                 155                 160

Thr Glu Arg Glu Val Glu Ile Ala Gly Lys Val Ala Glu Gly Lys Thr
                165                 170                 175

Asn Ser Asp Ile Ala Arg Glu Leu Phe Ile Ser Ala Gly Thr Val Lys
            180                 185                 190

Thr His Val Ala Ser Ile Gln Arg Lys Leu Gln Val Arg Asn Arg Val
        195                 200                 205

Gly Val Ala Val Arg Ala Trp Glu Leu Gly Tyr Ala Thr Gly Gln Thr
    210                 215                 220

Pro Gly
225
```

NON-RIBOSOMAL PEPTIDE SYNTHETASES AND ASSOCIATED BIOSYNTHETIC GENES

This application is a division of U.S. application Ser. No. 10/402,842, filed on Mar. 28, 2003, now abandoned which claims priority from U.S. Provisional Patent Application Ser. No. 60/368,713 filed on Mar. 29, 2002, each of which is herein incorporated by reference in its entirety.

FIELD OF THE INVENTION

The present invention relates to non-ribosomal peptide synthetases and associated biosynthetic genes. The present invention further relates to methods for generating novel compounds, such as antibiotics, with these synthetases and associated genes.

BACKGROUND OF THE INVENTION

Bioactive molecules that are isolated from plants, bacteria, and fungi are often referred to as natural products. These molecules are synthesized by primary or secondary pathways within the organism or may even be degradation products of another molecule. Many of these molecules have shown a variety of therapeutic uses in humans and other animal species. One of the best known examples is taxol, which was originally isolated from the bark of the Pacific Yew tree. Taxol has been shown to have anti-cancer properties and is currently used in the treatment of breast cancer. Actinomycetes are prolific producers of bioactive small molecules. These molecules may be used chemically as immunosuppressants, antibiotics, and cancer therapeutics. Actinomycetes are Gram-positive bacteria that form long, thread-like branched filaments. The term actinomycetes is used to indicate organisms belonging to *Actinomycetales*, an Order of the domain *Bacteria*. The *Actinomycetales* are divided into 34 Families including *Streptomyceteae*, to which belongs the Genus *Streptomyces* (Bergey's Manual of Systematic Bacteriology, Second Edition, 2001; George M. Garrity, Editor-in-Chief, Springer Verlag, New York).

Natural products derived from microbial sources primarily belong to three metabolic families: peptides, polyketides, and terpenes. Peptide natural products can be further classified based on their mode of synthesis: ribosomal and non-ribosomal. Non-ribosomal peptides are synthesized on enzymatic thiotemplates termed non-ribosomal peptide synthetases (NRPS). The non-ribosomal peptides encompass a wide range of compounds having diverse activities including, but not limited to, immunosupressive (such as cyclosporin), surfactant (such as surfactin), siderophores (such as enterobactin), virulence factors (such as yersinabactin), antibacterial (such as penicillin and vancomycin), and anti-cancer (such as actinomycin and bleomycin) activities (Weber et al., Current Genomics 1994; 26:120-25; Ehmann et al., Proc. Nat. Acad. Sci. 2000; 97:2509-14; Gehring et al., Biochemistry 1998; 37:11637; Kallow et al., Biochemistry 1998; 37:5947-52; Trauger et al., Proc. Nat. Acad. Sci. 2000; 97:3112-17; Schauweker et al., J. Bacteriology 1999; 27:2468-74; and Shen et al., Bioorganic Chem 1999; 27:155-71). Non-ribosomal peptides typically range in size from 1-11 amino acids and are produced by a variety of microbes including cyanobacteria, actinomycetes and fungi.

In many cases the non-ribosomal peptides contain non-proteogenic amino acids such as norleucine, β-alanine, ornithine, etc., for which biogenesis pathways, which are secondary to primary metabolism, are required and are post-synthetically modified (e.g., hydroxylated or methylated) by tailoring enzymes. As used herein, the term "proteogenic" indicates that the amino acid can be incorporated into a protein in a cell through well-known metabolic pathways. The choice of including a (D)- or (L)-amino acid into a peptide of the present invention depends, in part, on the desired characteristics of the peptide. For example, the incorporation of one or more (D)-amino acids can confer increasing stability on the peptide in vitro or in vivo. As used herein, the term "amino acid equivalent" refers to compounds which depart from the structure of the naturally occurring amino acids, but which have substantially the structure of an amino acid, such that they can be substituted within a peptide that retains biological activity. Thus, for example, amino acid equivalents can include amino acids having side chain modifications and/or substitutions, and also include related organic acids, amides or the like. The term "amino acid" is intended to include amino acid equivalents. The term "residues" refers both to amino acids and amino acid equivalents.

The genes required to make a NRPS and the necessary tailoring enzymes have been shown in all cases to be localized to the chromosome of the producing microbe. NRPSs are modular in nature, where a module may be defined as a segment of the NRPS necessary to catalyze the activation of a specific amino acid and result in the incorporation of that amino acid into a non-ribosomal peptide. A minimal module contains three domains: (1) adenylation domains (about 60 kDa), responsible for selecting and activating an amino acid and transferring the aminoacyl adenylate to a peptidyl carrying center; (2) thiolation domains, also referred to as peptidyl carrier proteins (8-10 kDa), containing a serine residue which is post-translationally modified with a 4-phosphopantetheine group (Ppant) which acts as an acceptor for the aminoacyl adenylate; and (3) condensation domains (50-60 kDa) which catalyze peptide bond-forming chain-translocating steps between an upstream peptidyl-s-Ppant and the downstream aminoacyl-Ppant of the adjacent module (Doekel, S. and Marahiel, M. A. 2000; Chem. Biol. 7:373-384). This minimal module for chain extension is typically repeated within a synthetase and a co-linear relationship exists between the number of modules present and the number of amino acids in the final product with the order of the modules in the synthetase determining the order of the amino acids in the peptide.

There is a continuing need in the art to determine the genes encoding NRPS complexes.

SUMMARY OF THE INVENTION

The present invention provides the nucleic acid and amino acid sequences of a non-ribosomal peptide synthetase (NRPS) complex from *Streptomyces hygroscopicus*. The NRPS described herein is comprised of two components, designated mppA and mppB, and contains the sequences required for the biosynthesis of the peptide core of lipoglycopeptide antibiotic AC98.

The present invention also provides characterization of mppA and mppB, including the number of modules in each component and the functional domains contained within each module. In particular, mppA is comprised of three modules, each containing an adenylation, thiolation, and condensation domain, and mppB is comprised of two modules, two epimerization domains, and a partial module comprised only of a condensation domain and thiolation domain.

Further provided by the present invention are expression vectors comprising the genes encoding mppA and mppB, and host cells transfected with such mppA and/or mppB-encoding vectors.

The present invention also provides nucleic acid and amino acid sequences for several open reading frames (ORFs) encoding associated gene products that modify the amino acids of the core peptide post-biosynthesis, as well as host cells comprising the ORFs.

In yet a further embodiment, the present invention provides a method for producing the NRPS described herein, which method comprises culturing an NPRS-transformed host cell under conditions that provide for expression of mppA and mppB.

The present invention further provides a method of producing a cyclic peptide synthesized by of the NRPS comprised of mppA and mppB, which peptide is an antibiotic. In a preferred embodiment, the antibiotic is AC98.

Also provided by the present invention are methods of modifying the adenylation domains of NRPS in order to produce an antibiotic having a modified peptide core, and a method for evaluating the structural regions of the modified peptide.

BRIEF DESCRIPTION OF DRAWINGS

FIG. 4A shows the serine-specific binding pocket of the adenylation domain of module 1 within mppA. FIG. 4B shows the glycine-specific binding pocket of the adenylation domain of module 2 within mppA. FIG. 4C shows the phenylalanine-specific binding pocket of the adenylation domain of module 3 within mppA. FIG. 4D shows the tyrosine-specific binding pocket of the adenylation domain of module 1 within mppB. FIG. 4E shows the cyclo-arginine-specific binding pocket of the adenylation domain of module 2 within mppB.

DETAILED DESCRIPTION OF THE INVENTION

The following definitions are The following definitions are provided for the full understanding of terms and abbreviations used in this specification.

The abbreviations in the specification correspond to units of measure, techniques, properties or compounds as follows: "min" means minutes, "h" means hour(s), "µL" means microliter(s), "mL" means milliliter(s), "mM" means millimolar, "M" means molar, "mmole" means millimole(s), "kb" means kilobase, "bp" means base pair(s), and "IU" means International Units. "Polymerase chain reaction" is abbreviated PCR; "Reverse transcriptase polymerase chain reaction" is abbreviated RT-PCR; "Estrogen receptor" is abbreviated ER; "DNA binding domain" is abbreviated DBD; "Ligand binding domain" is abbreviated LBD; "Untranslated region" is abbreviated UTR; "Sodium dodecyl sulfate" is abbreviated SDS; and "High Pressure Liquid Chromatography" is abbreviated HPLC.

*Streptomyces hygroscopicus* NS 17 is a terrestrial actinomycete which produces a novel lipoglycopeptide antibiotic complex (AC98; See FIG. 1). This strain has been deposited with the Agricultural Research Service Culture Collection, 1815 North University St., Peoria, Ill. 61604, Deposit No. NRRL 30439. This antibiotic has been shown to be active against Gram-positive pathogens including, but not limited to, vancomycin resistant enterococci (VRE), methicillin resistant *Staphlococcus aureus* (MRSA) and *Streptococcus pneumoniae*. The present invention is based on the isolation of the genes encoding a novel NRPS complex from this *Streptomyces* strain that is demonstrated to be the minimal biosynthetic machinery responsible for the biosynthesis of the peptide core of AC98 (see FIG. 2).

Figure 3:
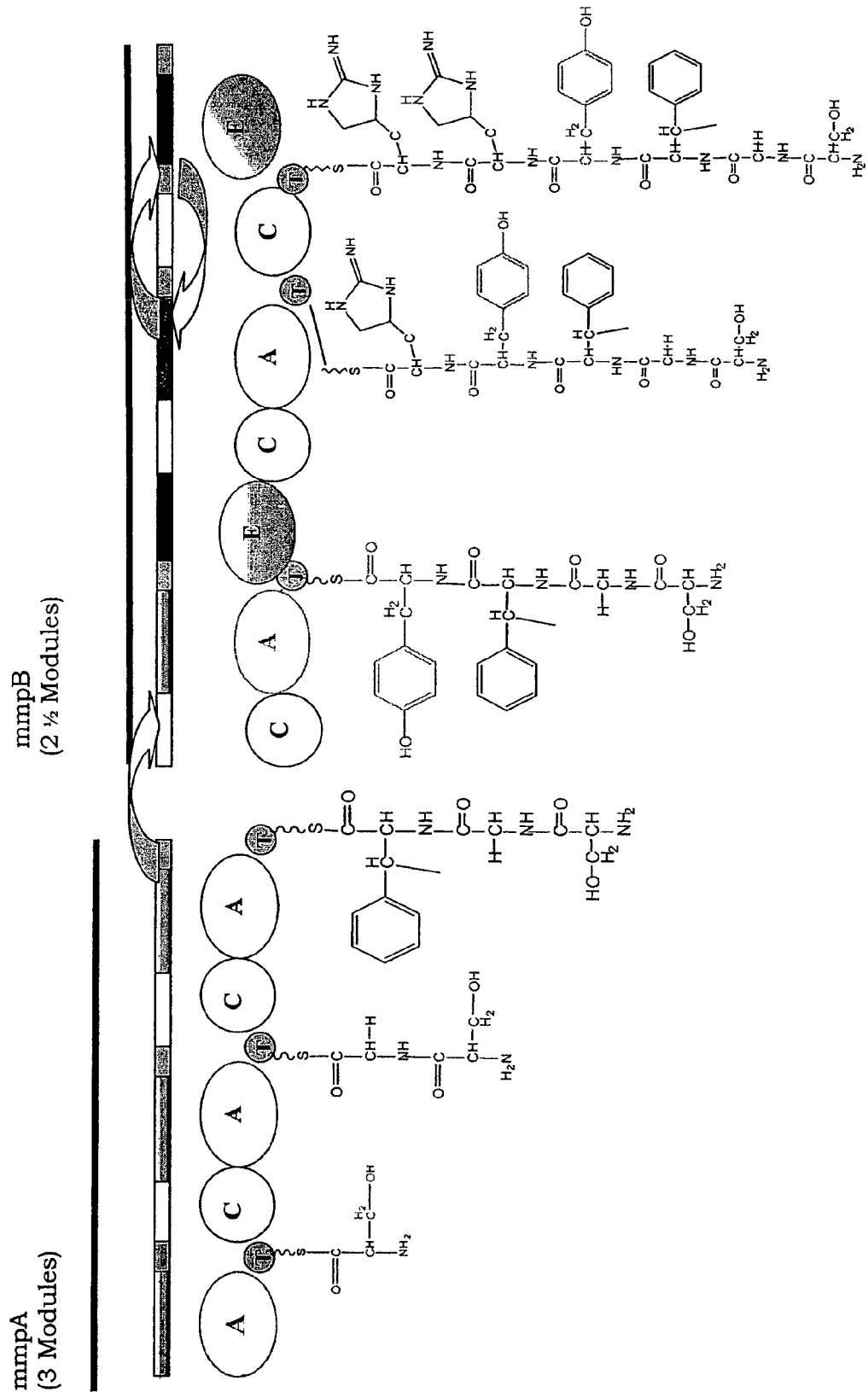
FIG. 3 is a pictorial representation of the biosynthesis of the AC98 peptide core by the novel NRPS described herein.
Figure 4A:
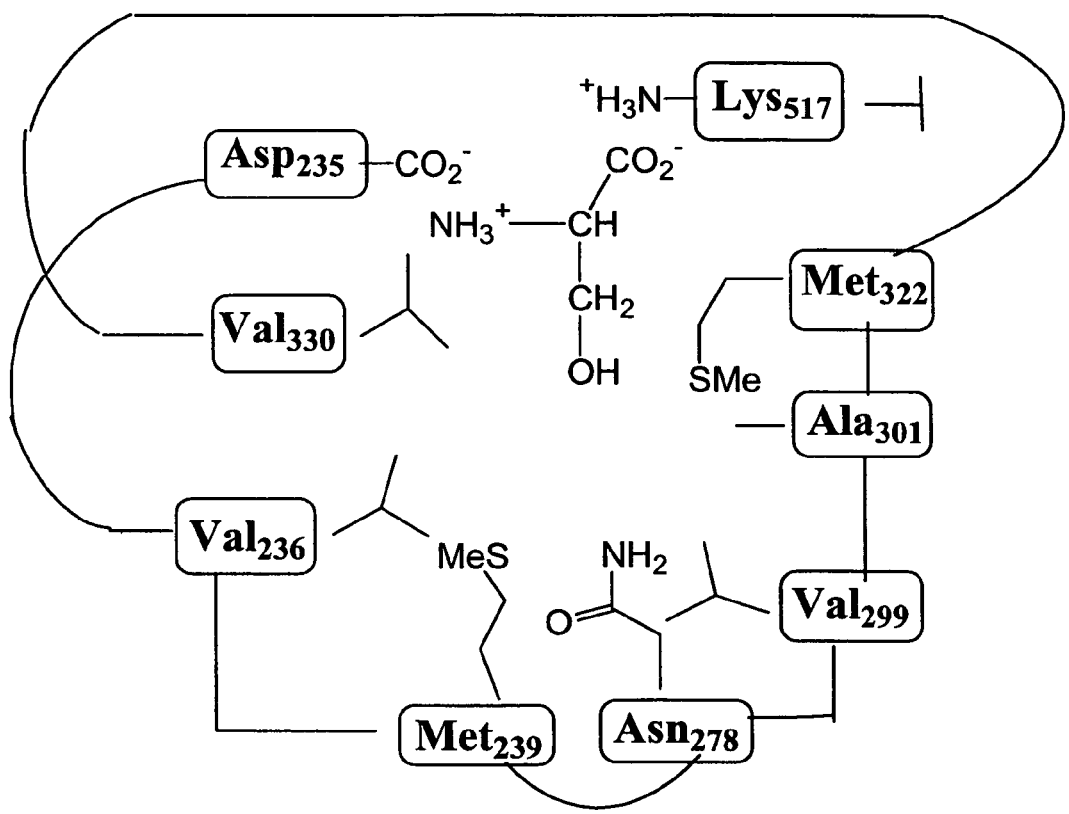
FIG. 4A-E depicts the two-dimensional representation of the binding pockets of adenylation domains within modules of the NRPS of the invention. Amino acid residues 235, 236, 239, 278, 299 & 301, are those that determine the specificity of the binding pocket.
Figure 4B:
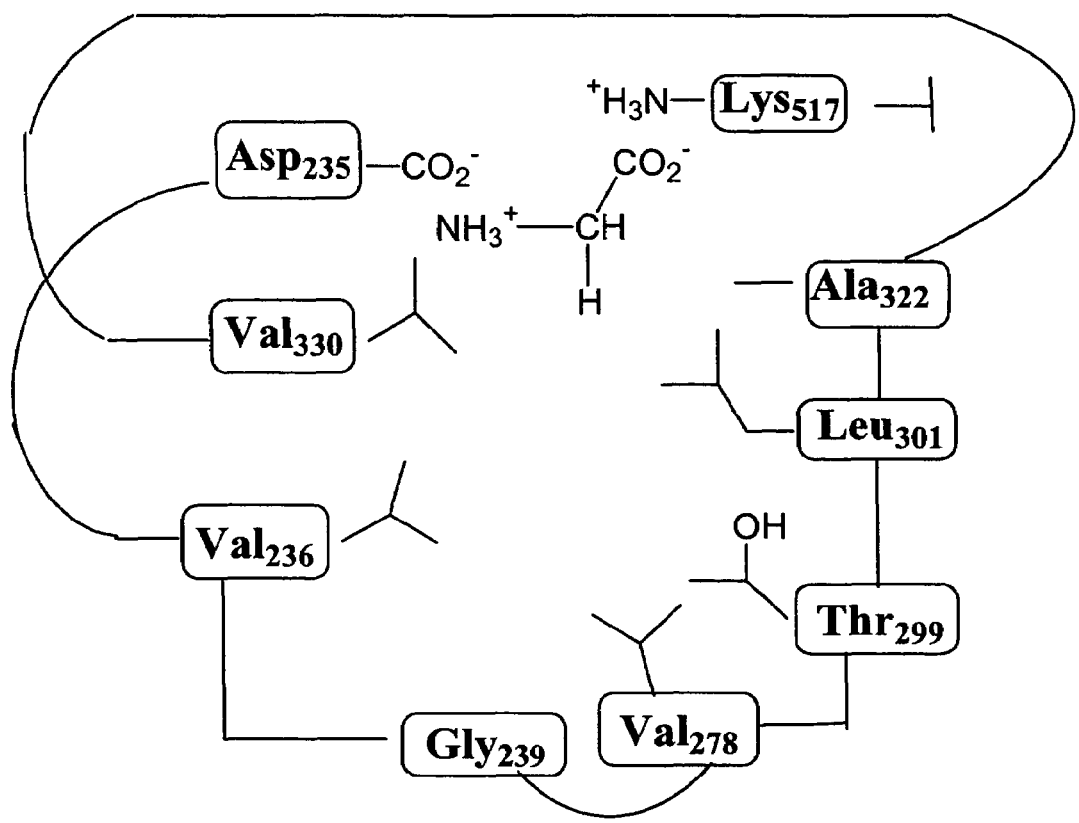
Figure 4C:
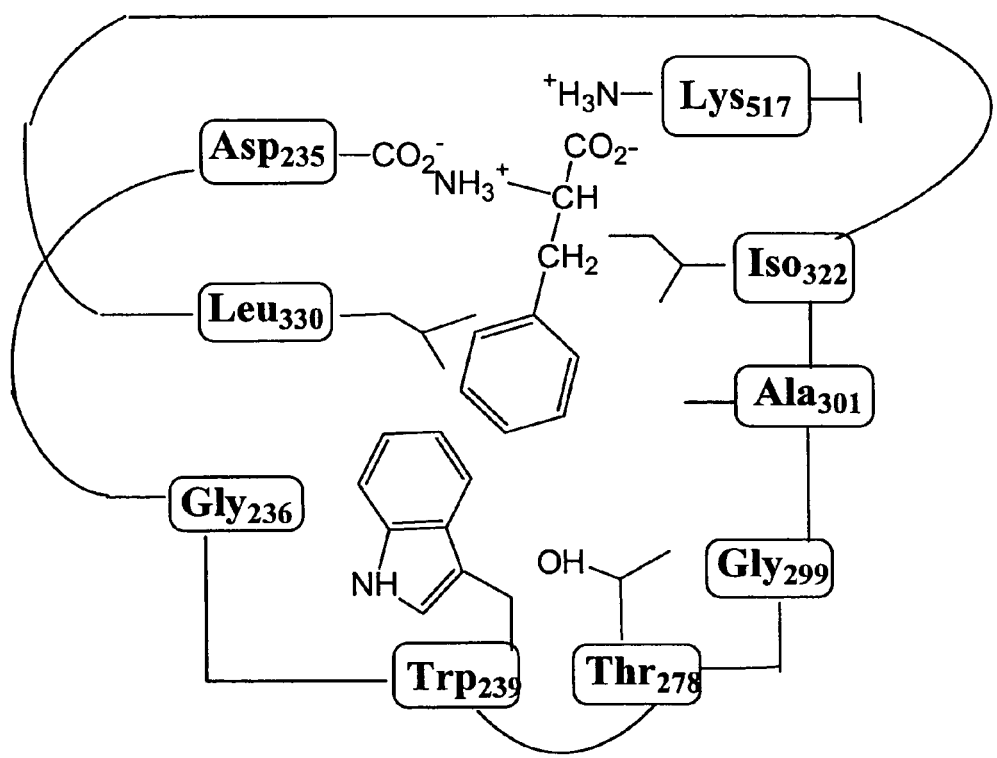
Figure 4D:
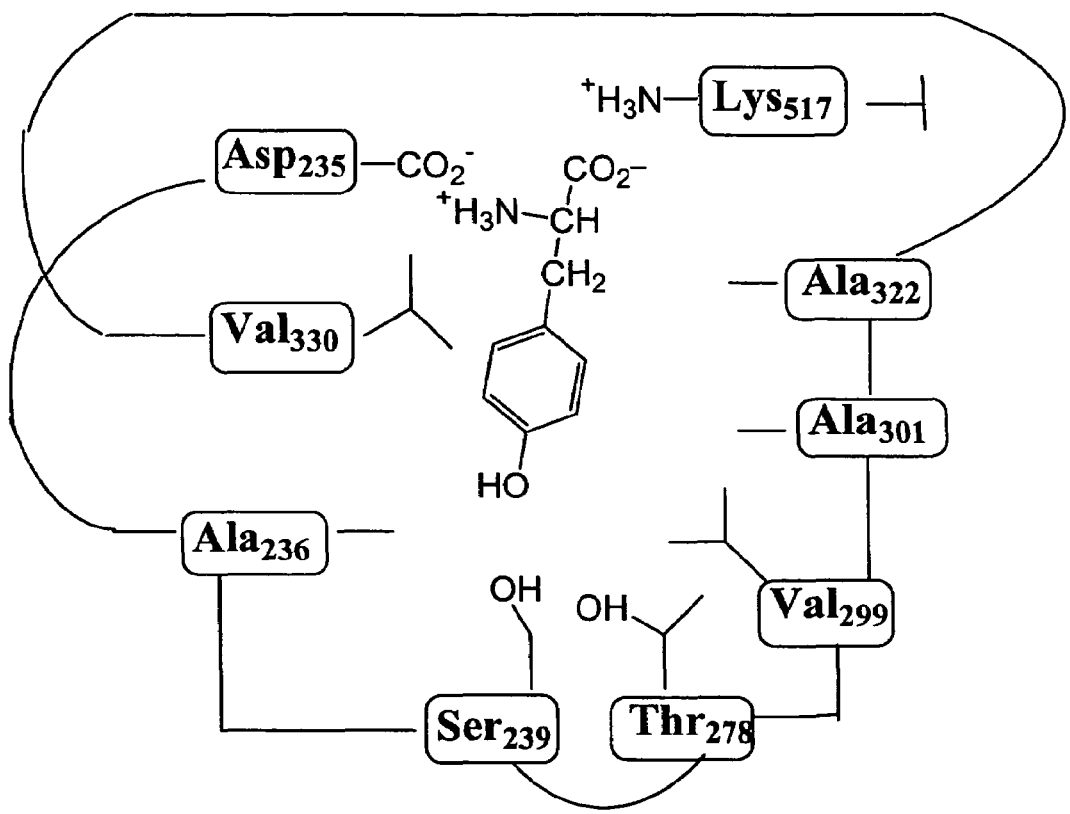
Figure 4E:
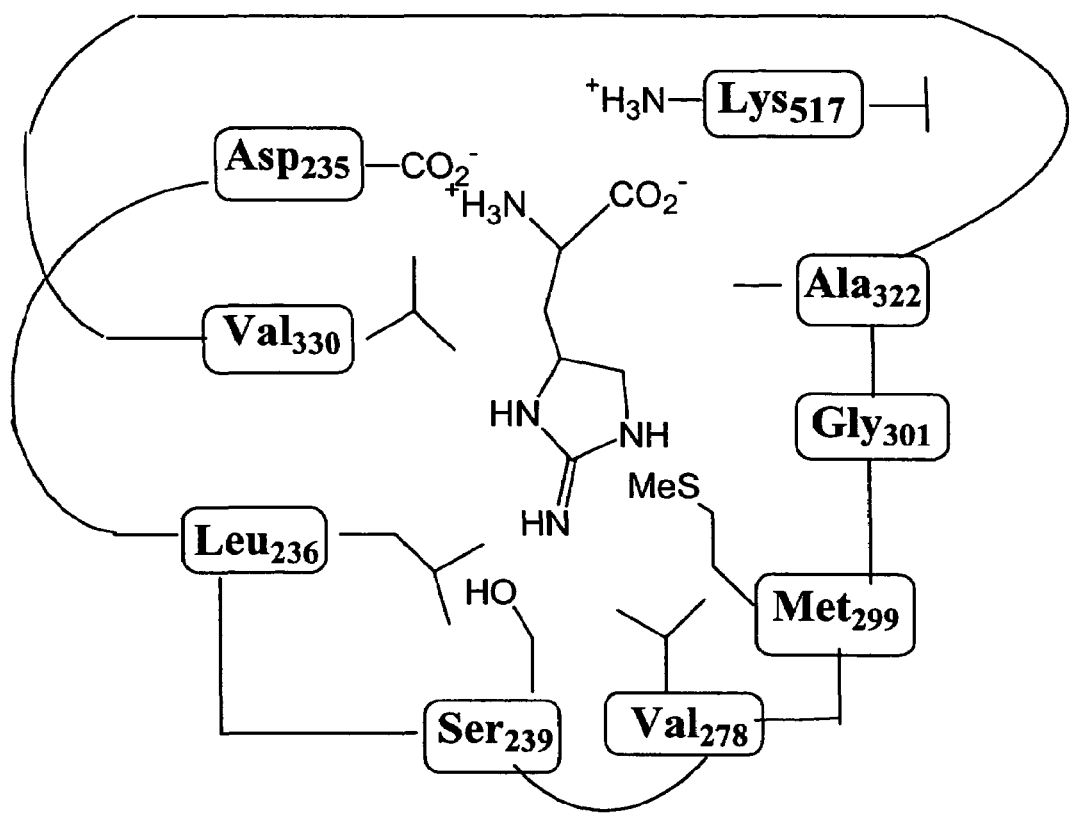

A number of open reading frames (ORFs), that are predicted to play a role in the biosynthesis of AC98, have been isolated and characterized by sequence analysis. Sequence comparisons of specific ORFs indicate that the proteins that are encoded by the ORFs are tailoring enzymes that are involved in such modifications of the peptide core as glycosylation, methylation and acylation. Other ORFs putatively encode enzymes that may be involved in resistance. A detailed description of the NRPS and its function in biosynthesis of the AC98 peptide core is presented in FIG. 3. The genes required to make the NRPS and the necessary tailoring enzymes are localized to the chromosome of the producing microbe.

NRPS

The NRPS enzymes are generally composed of modules where a minimal module contains three domains, an adenylation domain, a thiolation domain, and a condensation domain.

The adenylation domain is typically about 60 kDa. The main function of this domain is to select and activate a specific amino acid as an aminoacyl adenylate. Based on its function, the adenylation domain regulates the sequence of the peptide being produced. Once charged (as an amino acyl adenylate moiety), the amino acid is transferred to a thiolation domain (peptidyl carrying center).

The second domain is the thiolation domain, also referred to as a peptidyl carrier protein. This domain is typically 8-10 kDa and contains a serine residue that is post-translationally modified with a 4-phosphopantetheine group. This group acts as an acceptor for the aminoacyl adenylate moiety on the amino acid. A nucleophilic reaction leads to the release of the aminoacyl adenylate and conjugation of the amino acid to thiolation domain via a thioester bond.

The third domain is the condensation domain. This domain is typically about 50-60 kDa in size. The main function of this domain is to catalyze the formation of a peptide bond between two amino acids. In this reaction an upstream tethered peptidyl group is translocated to the downstream aminoacyl-s-Ppant and linked to the amino acid by peptide bond formation.

This minimal module for chain extension is typically repeated within a synthetase. Additionally, and typically, a co-linear relationship exists between the number of modules present and the number of amino acids in the final product with the order of the modules in the synthetase determining the order of the amino acids in the peptide. This 1:1 relationship, with every amino acid in the product having one module within the enzyme, is referred to as the co-linearity rule. Examples have been found that violate this rule, and in such cases, the NRPS contains more modules than one would expect based on the number of amino acids incorporated in the peptide product (Challis et al., Chem. Biol. 2000; 7:211-24). In some cases the minimal module also is supplemented with additional domains (epimerization, N- or C-methylation, or cyclization domain), with their position in the synthetase determining the substrate upon which they can act. In addition, it has been observed that NRPSs contain inter-domain spacers or linker regions. It has been proposed that these spacers may play a critical role in communication between domains, modules, and even entire synthetases.

There are highly conserved motifs in the catalytic domains of peptide synthetases including: 10 conserved motifs in the adenylation domain; 1 conserved motif in the thiolation domain; 7 conserved motifs in the condensation domain; 1 conserved motif in the thioesterase domain; 7 conserved motifs in the epimerization domains; and 3 conserved motifs in the N-methylation domains. These are detailed in Marahiel et al., Chemical Rev. 1997; 97:2651-73. In addition to modifications such as epimerization, methylation and cyclization during peptide synthesis, post-translational modifications including methylation, hydroxylation, oxidative cross-linking and glycosylation can occur (Walsh et al., Curr. Opin. Chem. Biol. 2001; 5:525-34).

In the present invention, a biosynthetic pathway containing the genes for a NRPS from *Streptomyces hygroscopicus* NS17 has been isolated and characterized (SEQ ID NO:1). The NRPS exists as two separate components that have been termed mppA and mppB. These components both are involved in the synthesis of the core of AC98.

MppA is composed of three minimal modules, where each module is comprised of an adenylation, thiolation, and condensation domain. MppA conjugates a serine amino acid to a glycine amino acid to produce a peptide. This peptide is then conjugated (through the glycine) to a phenylalanine amino acid. Each amino acid is incorporated into the peptide chain by a unique module. In one embodiment, mppA is about 295 kDa. In another embodiment, mppA is about 2747 amino acids in length. In one embodiment, mppA has an amino acid sequence as depicted in SEQ ID NO:2. In another embodiment, the mppA protein is encoded by a nucleic acid sequence as depicted in SEQ ID NO:3. After addition of the phenylalanine, the peptide chain is then transferred to the mppB component.

The specificity of each AC98 adenylation domain in the NRPS of the present invention was predicted based on the method described in Challis et al., Chem. Biol. 2000; 7:211-24. Amino acid residues 235, 236, 239, 278, 299 & 301 lining the binding pocket of each adenylation domain were found to define domain specificity (the adenylation domains of mppA and mppB modules are depicted in FIG. 4) and, in turn, the order of amino acid incorporation into the growing AC98 peptide chain (See FIG. 3).

MppB is composed of 2½ modules and two epimerization domains. In other words, mppB is comprised of 2 complete minimal modules (as described above for mppA) and an additional condensation and thiolation domain (which constitutes the ½ module). The peptide chain synthesized by mppA is transferred to mppB where a tyrosine amino acid is added to the chain. Prior to the condensation domain, an epimerization enzyme alters the chirality of the tyrosine residue from an L-amino acid to a D-amino acid. The peptide chain is then transferred to a module where a first cycloarginine moiety is added to the peptide. The module which incorporates the first cycloarginine moiety into the peptide is then reused to incorporate a second cycloarginine moiety. A second epimerization domain then alters the chirality of the second cycloarginine from an L-amino acid to a D-amino acid. The terminal module of mppB is unique in that there is only one adenylation domain used for the addition of two cycloarginine residues to the peptide core.

In one embodiment, mppB is about 394 kDa. In another embodiment, mppB is about 3668 amino acids in length. In one embodiment, mppB has an amino acid sequence as depicted in SEQ ID NO:4. In another embodiment, the mppB protein is encoded by a nucleic acid sequence as depicted in SEQ ID NO: 5. After epimerization, the peptide sequence is then modified by tailoring enzymes including, but not limited to, glycosylation enzymes, methylation enzymes and acylation enzymes.

Tailoring Enzymes

After production of the core of the peptide, the sequence may then be modified by additional enzymes which are herein termed "tailoring enzymes". These enzymes alter the amino acids in the compound without altering the number or the specific amino acids present within the compound. Such tailoring enzymes may include, but are not limited to, arginine cyclase, an O-mannosyltransferase, a phenylalanine C-methyltransferase, a first isovaleryl transferase, and a second isovaleryl transferase.

In the present invention, these tailoring enzymes have been determined to be ORFs present on the AC98 biosynthetic gene cluster and have been termed ORF1-ORF23. Sequence comparison of these ORFs with homologs provide preliminary information about the function of the enzymes. Table 1 below provides a correlation between the ORF, its location within SEQ ID NO: 1, and its proposed function.

The present invention permits specific changes to be made to the ORFs that encode the tailoring enzymes, either by site directed mutagenesis or replacement, to genetically modify the peptide core. The modifications may be made in a rational manner to improve the biological activity of the antibiotic produced by the bacterial strain or to direct synthesis of compounds that are structurally related to AC98. The invention also allows for the ORFs encoding tailoring enzymes to be isolated and used for biotransformation experiments to produce enzymes to modify and possibly improve other useful compounds.

The determination of the entire biosynthetic pathway of AC98 also enables one of ordinary skill in the art to clone and express the pathway into a heterologous organism. Any organism may be used; preferably a bacterial strain is used. The choice of organism is dependent upon the needs of the skilled artisan. For example, a strain that is amenable to genetic manipulation may be used in order to facilitate modification and production of AC98.

The present invention advantageously permits specific changes to be made to individual modules of NRPS, either by site directed mutagenesis or replacement, to genetically modify the peptide core. Additionally, the NRPS modules can be used to modify other NRPSs that direct the synthesis of other useful peptides through module swapping. For example, the module in NRPS that incorporates tyrosine into the peptide core of the antibiotic may be modified so as to incorporate a serine in its place.

TABLE 1

ORF Correlation

| ORF | Position (bp) | No. Amino Acids | Sequence Homolog Accession No.* | Percent Identity | Proposed Function |
|---|---|---|---|---|---|
| ORF1 (SEQ ID NO: 6) | 77-1048 | 323 (SEQ ID NO: 21) | BAB69251 Pfam PF00583 | 68% | Acetyltransferase |
| ORF2 (SEQ ID NO: 7) | 1045-2460 | 471 (SEQ ID NO: 22) | BAB69250 Pfam PF01574 | 61% | ABC transporter |
| ORF3 (SEQ ID NO 8) | 2495-3406 | 303 (SEQ ID NO: 23) | BAB69249 Pfam PF00528 | 70% | ABC transporter |
| ORF4 (SEQ ID NO 9) | 3403-4293 | 296 (SEQ ID NO: 24) | BAB69248 Pfam PF00528 | 67% | ABC transporter |
| ORF5 (SEQ ID NO: 10) | 4359-5635 | 402 (SEQ ID NO: 25) | G75191 Pfam PF00535 | 34% | Mannosyltransferase |
| ORF6 (SEQ ID NO: 11) | 5822-7234 | 467 (SEQ ID NO: 26) | AE007470 | 20% | Unknown |
| ORF7 (SEQ ID NO: 12) | 7293-8822 | 509 (SEQ ID NO: 27) | X91736 | 29% | Unknown |
| ORF8 (SEQ ID NO: 13) | 9012-10025 | 318 (SEQ ID NO: 28) | X79146 Pfam PF00891 | 27% | methyltransferase |
| ORF9 (SEQ ID NO: 14) | 29319-30638 | 450 (SEQ ID NO: 29) | Z13972 | 32% | D-aminoacyl hydrolase superfamily |
| ORF10 (SEQ ID NO: 15) | 30658-32010 | 450 (SEQ ID NO: 30) | BAB69335 | 29% | efflux protein |
| ORF11 (SEQ ID NO: 16) | 32181-33407 | 408 (SEQ ID NO: 31) | AF263245 Pfam PF01757 | 38% | isovaleryl transferase |
| ORF12 (SEQ ID NO: 17) | 33422-34792 | 456 (SEQ ID NO: 32) | AF263245 Pfam PF01757 | 31% | isovaleryl transferase |
| ORF13 (SEQ ID NO: 18) | 34905-35939 | 344 (SEQ ID NO: 33) | AJ271405 | 41% | argenine cyclase |
| ORF14 (SEQ ID NO: 34) | 36386-37267 | 293 (SEQ ID NO: 35) | AF110468 | 31% | Transaminase |
| ORF15 (SEQ ID NO: 36) | 37267-38514 | 415 (SEQ ID NO: 37) | AE001954 | 30% | Transaminase |
| ORF16 (SEQ ID NO: 38) | 38547-40382 | 637 (SEQ ID NO: 39) | AL589164 | 34% | Regulatory Protein |
| ORF17 (SEQ ID NO: 40) | 40444-40659 | 71 (SEQ ID NO: 41) | AL035654 | 69% | cda-ORFX homolog |
| ORF18 (SEQ ID NO: 42) | 42554-41100 | 484 (SEQ ID NO: 43) | AE005887 | 36% | putative secreted protein |
| ORF19 (SEQ ID NO: 44) | 44648-42936 | 570 (SEQ ID NO: 45) | AL939114 | 33% | hypothetical protein |
| ORF20 (SEQ ID NO: 46) | 45435-44581 | 285 (SEQ ID NO: 47) | AE006014 | 44% | ABC transporter |
| ORF21 (SEQ ID NO: 48) | 45920-45504 | 138 (SEQ ID NO: 49) | AL356892 | 37% | putative lipoprotein |
| ORF22 (SEQ ID NO: 50) | 47181-45991 | 396 (SEQ ID NO: 51) | AL096872 | 35% | two component sensor kinase |
| ORF23 (SEQ ID NO: 52) | 47988-47308 | 226 (SEQ ID NO: 53) | AL132648 | 47% | two component response regulator |
| mppA (SEQ ID NO: 3) | 10069-18309 | 2747 (SEQ ID NO: 2) | AL035640 | N/A | NRPS |
| mppB (SEQ ID NO: 5) | 18309-29312 | 3668 (SEQ ID NO: 4) | AL035640 | N/A | NRPS |

*SeqWeb ™, which uses Wisconsin [GCG] Package version 10

Methods of Modifying Bacterial Proteins

The role of the proteins encoded by mppA, mppB, or ORF1-ORF23 may be evaluated using any method known in the art. For example, specific modifications to a protein sequence may be produced to alter the final product. Other non-limiting examples of studies that may be conducted with these proteins include (i) evaluation of the biological activity of a protein and (ii) manipulation of a synthetic pathway to alter the final product from bacteria. More detailed discussion of these proposed uses follows.

Genetic manipulations and expression of the proteins discussed herein may be conducted by any method known in the art. For example, the effect of point mutations may be evaluated. The mutations may be produced by any method known in the art. In one specific method the manipulations and protein expression may be conducted using a vector that comprises at least one Gram-negative and at least one Gram-positive origin of replication. The origins of replication allow for replication of the nucleic acid encoded by the vector, in either a Gram-negative or a Gram-positive cell line. In one embodiment, the vector comprises one Gram-negative and one Gram-positive origin of replication. Additionally, the vector comprises a multiple cloning site that allows for the insertion of a heterologous nucleic acid that may be replicated and transcribed by a host cell.

The most evolved mechanism of transfer of nucleic acids is conjugation. As used herein, the term "conjugation" refers to the direct transfer of nucleic acid from one prokaryotic cell to another via direct contact of cells. The origin of transfer is determined by a vector, so that both donor and recipient cells obtain copies of the vector. Transmissibility by conjugation is controlled by a set of genes in the tra region, which also has the ability to mobilize the transfer of chromosomes when the origin of transfer is integrated into them (Pansegrau et al., *J. Mol. Biol.*, 239:623-663, 1994; Fong and Stanisich, *J. Bact.*, 175:448-456, 1993).

Evaluation of the Biological Activity of a Protein

Evaluation of the mechanism of a protein and role the protein plays in the synthesis of a compound has traditionally been determined using sequence homology techniques. However, such techniques may not be accurate and better methods of evaluating novel proteins need to be developed. The vector described previously may be used to assess the biological activity of an unknown protein. The vector may be used to disrupt a protein, either by partial or complete removal of the gene encoding the protein, or by disruption of that gene. Evaluation of the products produced when the altered protein is present is useful in determining the function of the protein.

Manipulation of a Synthetic Pathway to Alter the Final Product

As discussed above, many compounds obtained from organisms have complex stereochemistries. These compounds are not amenable to production or manipulation by conventional synthetic methods. Therefore, new methods are needed to produce altered products.

Specific proteins within the biochemical pathway of the product may be modified to assess the activity of the compounds produced by these altered proteins and to determine which sections of the product are important for activity and function.

The present invention contemplates any method of altering any of the proteins of the present invention. More specifically, the invention contemplates any method that would insert amino acids, delete amino acids or replace amino acids in the proteins of the invention. Additionally, a whole domain in a module in mppA or mppB may be replaced. Therefore, for example, the acylation domain that incorporates tyrosine into the final product may be replaced with a domain that incorporates serine. The modifications may be performed at the nucleic acid level. These modifications are performed by standard techniques and are well known within the art.

Upon production of the nucleic acid encoding the modified protein, the protein can be expressed in a host cell. Then the host cell can be cultured under conditions that permit production of a product of the altered pathway.

Once the product is isolated, the activity of the product may be assessed using any method known in the art. The activity can be compared to the product of the non-modified biosynthetic pathway and to products produced by other modifications. Correlations may be drawn between specific alterations and activity. For example, it may be determined that an active residue at a specific position may increase activity. These types of correlations will allow one of ordinary skill to determine the most preferred product structure for specified activity.

The present invention also contemplates a method for using an intergeneric vector, described infra in the examples, to manipulate, modify, or isolate a protein involved in the synthesis of a specific product. For example, the vector of the present invention may be used to alter an enzyme which is involved in incorporation of an alanine residue into a peptide, so that a tyrosine residue is incorporated instead. The effect of this modification on peptide function may be then be evaluated for biological efficacy. In the above example, modifications to the enzyme may include, but are not limited to, removal of amino acids and/or sequences that specifically recognize alanine and/or incorporation of amino acids and/or sequences that specifically recognize tyrosine.

Therefore, in general terms, the vector of the present invention may be used to alter a gene sequence by insertion of nucleic acid sequences, deletion of nucleic acid sequences, or alteration of specific bases within a nucleic acid sequence to alter the sequence of a protein of interest; thereby producing a modified protein of interest. Preferably, the protein of interest is involved in the synthesis of a compound of interest. The method of modifying a protein comprises (i) transfecting a first bacterial cell with the vector of the present invention, (ii) culturing the first bacterial cell under conditions that allow for replication of the vector, (iii) conjugating the first bacterial cell with a second bacterial cell under conditions that allow for the direct transfer of the vector from the first bacterial cell to the second bacterial cell, and (iv) isolating the second bacterial cell transformed with the vector. In a preferred embodiment, the first cell is a Gram-negative bacterial cell and the second cell is a Gram-positive cell.

Molecular Biology

In accordance with the present invention there may be employed conventional molecular biology, microbiology, and recombinant DNA techniques within the skill of the art. Such techniques are explained fully in the literature. See, e.g., Sambrook, Fritsch & Maniatis, *Molecular Cloning: A Laboratory Manual*, Second Edition (1989) Cold Spring Harbor Laboratory Press, Cold Spring Harbor, N.Y. (herein "Sambrook et al., 1989"); *DNA Cloning: A Practical Approach*, Volumes I and II (D. N. Glover ed. 1985); *Oligonucleotide Synthesis* (M. J. Gait ed. 1984); *Nucleic Acid Hybridization* (B. D. Hames & S. J. Higgins eds. (1985)); *Transcription And Translation* (B. D. Hames & S. J. Higgins, eds. (1984)); *Animal Cell Culture* (R. I. Freshney, ed. (1986)); *Immobilized Cells And Enzymes* (IRL Press, (1986)); B. Perbal, *A Practical Guide To Molecular Cloning* (1984); F. M. Ausubel et al. (eds.), *Current Protocols in Molecular Biology*, John Wiley & Sons, Inc. (1994).

"Amplification" of DNA as used herein denotes the use of polymerase chain reaction (PCR) to increase the concentration of a particular DNA sequence within a mixture of DNA sequences. For a description of PCR see Saiki et al., Science 1988, 239:487.

A "nucleic acid molecule" refers to the phosphate ester polymeric form of ribonucleosides (adenosine, guanosine, uridine or cytidine; "RNA molecules") or deoxyribonucleosides (deoxyadenosine, deoxyguanosine, deoxythymidine, or deoxycytidine; "DNA molecules"), or any phosphoester analogs thereof, such as phosphorothioates and thioesters, in either single stranded form, or a double-stranded helix. Double stranded DNA-DNA, DNA-RNA and RNA-RNA helices are possible. The term nucleic acid molecule, and in particular DNA or RNA molecule, refers only to the primary and secondary structure of the molecule, and does not limit it to any particular tertiary forms. Thus, this term includes double-stranded DNA found, inter alia, in linear (e.g., restriction fragments) or circular DNA molecules, plasmids, and chromosomes. In discussing the structure of particular double-stranded DNA molecules, sequences may be described herein according to the normal convention of giving only the sequence in the 5' to 3' direction along the non-transcribed strand of DNA (i.e., the strand having a sequence homologous to the mRNA). A "recombinant DNA molecule" is a DNA molecule that has undergone a molecular biological manipulation.

A "polynucleotide" or "nucleotide sequence" is a series of nucleotide bases (also called "nucleotides") in a nucleic acid, such as DNA and RNA, and means any chain of two or more nucleotides. A nucleotide sequence typically carries genetic information, including the information used by cellular machinery to make proteins and enzymes. These terms include double or single stranded genomic and cDNA, RNA, any synthetic and genetically manipulated polynucleotide, and both sense and anti-sense polynucleotide (although only sense stands are being represented herein). This includes single- and double-stranded molecules, i.e., DNA-DNA, DNA-RNA and RNA-RNA hybrids, as well as "protein nucleic acids" (PNA) formed by conjugating bases to an amino acid backbone. This also includes nucleic acids containing modified bases, for example thio-uracil, thio-guanine and fluoro-uracil.

The nucleic acids herein may be flanked by natural regulatory (expression control) sequences, or may be associated with heterologous sequences, including promoters, internal ribosome entry sites (IRES) and other ribosome binding site sequences, enhancers, response elements, suppressors, signal sequences, polyadenylation sequences, introns, 5'- and 3'-non-coding regions, and the like. The nucleic acids may also be modified by many means known in the art. Non-limiting examples of such modifications include methylation, "caps", substitution of one or more of the naturally occurring nucleotides with an analog, and internucleotide modifications such as, for example, those with uncharged linkages (e.g., methyl phosphonates, phosphotriesters, phosphoroamidates, carbamates, etc.) and with charged linkages (e.g., phosphorothioates, phosphorodithioates, etc.). Polynucleotides may contain one or more additional covalently linked moieties, such as, for example, proteins (e.g., nucleases, toxins, antibodies, signal peptides, poly-L-lysine, etc.), intercalators (e.g., acridine, psoralen, etc.), chelators (e.g., metals, radioactive metals, iron, oxidative metals, etc.), and alkylators. The polynucleotides may be derivatized by formation of a methyl or ethyl phosphotriester or an alkyl phosphoramidate linkage. Furthermore, the polynucleotides herein may also be modified with a label capable of providing a detectable signal, either directly or indirectly. Exemplary labels include radioisotopes, fluorescent molecules, biotin, and the like.

A "promoter" or "promoter sequence" is a DNA regulatory region capable of binding RNA polymerase in a cell and initiating transcription of a downstream (3' direction) coding sequence. For purposes of defining the present invention, the promoter sequence is bounded at its 3' terminus by the transcription initiation site and extends upstream (5' direction) to include the minimum number of bases or elements necessary to initiate transcription at levels detectable above background. Within the promoter sequence will be found a transcription initiation site (conveniently defined for example, by mapping with nuclease S1), as well as protein binding domains (consensus sequences) responsible for the binding of RNA polymerase. The promoter may be operatively associated with other expression control sequences, including enhancer and repressor sequences.

A "coding sequence" or a sequence "encoding" an expression product, such as a RNA, polypeptide, protein, or enzyme, is a nucleotide sequence that, when expressed, results in the production of that RNA, polypeptide, protein, or enzyme, i.e., the nucleotide sequence encodes an amino acid sequence for that polypeptide, protein or enzyme. A coding sequence for a protein may include a start codon (usually ATG) and a stop codon.

The term "gene", also called a "structural gene" means a DNA sequence that codes for or corresponds to a particular sequence of amino acids which comprise all or part of one or more proteins or enzymes, and may or may not include regulatory DNA sequences, such as promoter sequences, which determine for example the conditions under which the gene is expressed. Some genes, which are not structural genes, may be transcribed from DNA to RNA, but are not translated into an amino acid sequence. Other genes may function as regulators of structural genes or as regulators of DNA transcription.

A coding sequence is "under the control of" or "operatively associated with" expression control sequences in a cell when RNA polymerase transcribes the coding sequence into RNA, particularly mRNA, which is then trans-RNA spliced (if it contains introns) and translated into the protein encoded by the coding sequence.

The term "expression control sequence" refers to a promoter and any enhancer or suppression elements that combine to regulate the transcription of a coding sequence. In a preferred embodiment, the element is an origin of replication.

The terms "vector", "cloning vector" and "expression vector" refer to the vehicle by which DNA can be introduced into a host cell, resulting in expression of the introduced sequence. In one embodiment, vectors comprise a promoter and one or more control elements (e.g., enhancer elements) that are heterologous to the introduced DNA but are recognized and used by the host cell. In another embodiment, the sequence that is introduced into the vector retains its natural promoter that may be recognized and expressed by the host cell (Bormann et al., J. Bacteriol 1996; 178:1216-1218).

An "intergeneric vector" is a vector that permits intergeneric conjugation, i.e., utilizes a system of passing DNA from E. coli to actinomycetes directly (Keiser, T. et al., Practical Streptomyces Genetics (2000) John Innes Foundation, John Innes Centre (England)). Intergeneric conjugation has fewer manipulations than transformation.

Vectors typically comprise the DNA of a transmissible agent, into which foreign DNA is inserted. A common way to insert one segment of DNA into another segment of DNA involves the use of enzymes called restriction enzymes that cleave DNA at specific sites (specific groups of nucleotides) called restriction sites. A "cassette" refers to a DNA coding sequence or segment of DNA that codes for an expression product that can be inserted into a vector at defined restriction sites. The cassette restriction sites are designed to ensure insertion of the cassette in the proper reading frame. Generally, foreign DNA is inserted at one or more restriction sites of the vector DNA, and then is carried by the vector into a host cell along with the transmissible vector DNA. A segment or sequence of DNA having inserted or added DNA, such as an expression vector, can also be called a "DNA construct". A common type of vector is a "plasmid", which generally is a self-contained molecule of double-stranded DNA, usually of bacterial origin, that can readily accept additional (foreign) DNA and which can readily introduced into a suitable host cell. A plasmid vector often contains coding DNA and promoter DNA and has one or more restriction sites suitable for inserting foreign DNA. Coding DNA is a DNA sequence that encodes a particular amino acid sequence for a particular protein or enzyme. Promoter DNA is a DNA sequence which initiates, regulates, or otherwise mediates or controls the expression of the coding DNA. Promoter DNA and coding DNA may be from the same gene or from different genes, and may be from the same or different organisms. Recombinant cloning vectors will often include one or more replication systems for cloning or expression, one or more markers for selection in the host, e.g. antibiotic resistance, and one or more expression cassettes. Vector constructs may be produced using conventional molecular biology and recombinant DNA techniques within the skill of the art. Such techniques are explained fully in the literature. See, e.g., Sambrook, Fritsch & Maniatis, Molecular Cloning: A Laboratory Manual, Second Edition (1989) Cold Spring Harbor Laboratory Press, Cold Spring Harbor, N.Y. (herein "Sambrook et al., 1989"); DNA Cloning: A Practical Approach, Volumes I and II (D. N. Glover ed. 1985); F. M. Ausubel et al. (eds.), Current Protocols in Molecular Biology, John Wiley & Sons, Inc. (1994).

The terms "express" and "expression" mean allowing or causing the information in a gene or DNA sequence to become manifest, for example producing a protein by activating the cellular functions involved in transcription and translation of a corresponding gene or DNA sequence. A DNA sequence is expressed in or by a cell to form an "expression product" such as a protein. The expression product itself, e.g,. the resulting protein, may also be said to be "expressed" by the cell. An expression product can be characterized as intracellular, extracellular or secreted. The term "intracellular" means something that is inside a cell. The term "extracellular" means something that is outside a cell. A substance is "secreted" by a cell if it appears in significant measure outside the cell, from somewhere on or inside the cell.

The term "transfection" means the introduction of a foreign nucleic acid into a cell. The term "transformation" means the introduction of a "foreign" (i.e. extrinsic or extracellular) gene, DNA or RNA sequence to a cell, so that the host cell will express the introduced gene or sequence to produce a desired substance, typically a protein or enzyme coded by the introduced gene or sequence. The introduced gene or sequence may also be called a "cloned" or "foreign" gene or sequence, may include regulatory or control sequences, such as start, stop, promoter, signal, secretion, or other sequences used by a cells genetic machinery. The gene or sequence may include nonfunctional sequences or sequences with no known function. A host cell that receives and expresses introduced DNA or RNA has been "transformed" and is a "transformant" or a "clone." The DNA or RNA introduced to a host cell can come from any source, including cells of the same genus or species as the host cell, or cells of a different genus or species.

The term "host cell" means any cell of any organism that is selected, modified, transformed, grown or used or manipulated in any way for the production of a substance by the cell. For example, a host cell may be one that is manipulated to express a particular gene, a DNA or RNA sequence, a protein or an enzyme. Host cells can further be used for screening or other assays that are described infra. Host cells may be cultured in vitro or one or more cells in a non-human animal (e.g., a transgenic animal or a transiently transfected animal). For the present invention, host cells include but are not limited to *Streptomyces* species and *E. Coli*.

The term "expression system" means a host cell and compatible vector under suitable conditions, e.g. for the expression of a protein coded for by foreign DNA carried by the vector and introduced to the host cell. In a specific embodiment, the host cell of the present invention is a Gram-negative or Gram-positive bacteria. These bacteria include, but are not limited to, *E. coli* and *Streptomyces* species. An example of a *Streptomyces* species that may be used includes, but is not limited to, *Streptomyces hygroscopicus*.

The term "heterologous" refers to a combination of elements not naturally occurring. For example, heterologous DNA refers to DNA not naturally located in the cell, or in a chromosomal site of the cell. Preferably, the heterologous DNA includes a gene foreign to the cell. For example, the present invention includes chimeric DNA molecules that comprise a DNA sequence and a heterologous DNA sequence which is not part of the DNA sequence. In this context, the heterologous DNA sequence refers to an DNA sequence that is not naturally located within the NRPS sequence. Alternatively, the heterologous DNA sequence may be naturally located within the NRPS sequence, but is found at a location in the NRPS sequence where it does not naturally occur. A heterologous expression regulatory element is such an element is operatively associated with a different gene than the one it is operatively associated with in nature. In the context of the present invention, a gene encoding a protein of interest is heterologous to the vector DNA in which it is inserted for cloning or expression, and it is heterologous to a host cell containing such a vector, in which it is expressed.

The terms "mutant" and "mutation" mean any detectable change in genetic material, e.g. DNA, or any process, mechanism, or result of such a change. This includes gene mutations, in which the structure (e.g. DNA sequence) of a gene is altered, any gene or DNA arising from any mutation process, and any expression product (e.g. protein or enzyme) expressed by a modified gene or DNA sequence.

The term "variant" may also be used to indicate a modified or altered gene, DNA sequence, enzyme, cell, etc., i.e., any kind of mutant. Two specific types of variants are "sequence-conservative variants", a polynucleotide sequence where a change of one or more nucleotides in a given codon position results in no alteration in the amino acid encoded at that position, and "function-conservative variants", where a given amino acid residue in a protein or enzyme has been changed without altering the overall conformation and function of the polypeptide. Amino acids with similar properties are well known in the art. Amino acids other than those indicated as conserved may differ in a protein or enzyme so that the percent protein or amino acid sequence similarity between any two proteins of similar function may vary and may be, for example, from 70% to 99% as determined according to an alignment scheme such as by the Clustal Method, wherein similarity is based on the algorithms available in MEGALIGN. A "function-conservative variant" also includes a polypeptide or enzyme which has at least 60% amino acid identity as determined by BLAST or FASTA alignments, preferably at least 75%, more preferably at least 85%, and most preferably at least 90%, and which has the same or substantially similar properties or functions as the native or parent protein or enzyme to which it is compared.

As used herein, the terms "homologous" and "homology" refer to the relationship between proteins that possess a "common evolutionary origin," including proteins from superfamilies (e.g., the immunoglobulin superfamily) and homologous proteins from different species (e.g., myosin light chain, etc.) (Reeck et al., Cell 50:667, 1987). Such proteins (and their encoding genes) have sequence homology, as reflected by their sequence similarity, whether in terms of percent similarity or the presence of specific residues or motifs at conserved positions.

Accordingly, the term "sequence similarity" refers to the degree of identity or correspondence between nucleic acid or amino acid sequences of proteins that may or may not share a common evolutionary origin (see Reeck et al., supra). However, in common usage and in the instant application, the term "homologous," when modified with an adverb such as "highly," may refer to sequence similarity and may or may not relate to a common evolutionary origin.

In a specific embodiment, two DNA sequences are "substantially homologous" or "substantially similar" when at least about 80%, and most preferably at least about 90% or 95% of the nucleotides match over the defined length of the DNA sequences, as determined by sequence comparison algorithms, such as BLAST, FASTA, DNA Strider, etc. An example of such a sequence is an allelic or species variant of the specific genes of the invention. Sequences that are substantially homologous can be identified by comparing the sequences using standard software available in sequence data banks, or in a Southern hybridization experiment under, for example, stringent conditions as defined for that particular system.

Similarly, in a particular embodiment, two amino acid sequences are "substantially homologous" or "substantially similar" when greater than 80% of the amino acids are identical, or greater than about 90% are similar. Preferably, the amino acids are functionally identical. Preferably, the similar or homologous sequences are identified by alignment using, for example, the GCG (Genetics Computer Group, Program Manual for the GCG Package, Version 10, Madison, Wis.) pileup program, or any of the programs described above (BLAST, FASTA, etc.).

A nucleic acid molecule is "hybridizable" to another nucleic acid molecule, such as a cDNA, genomic DNA, or RNA, when a single stranded form of the nucleic acid molecule can anneal to the other nucleic acid molecule under the appropriate conditions of temperature and solution ionic strength (see Sambrook et al., supra). The conditions of temperature and ionic strength determine the "stringency" of the hybridization. For preliminary screening for homologous nucleic acids, low stringency hybridization conditions, corresponding to a $T_m$ (melting temperature) of 55° C., can be used, e.g., 5×SSC, 0.1% SDS, 0.25% milk, and no formamide; or 30% formamide, 5×SSC, 0.5% SDS). Moderate stringency hybridization conditions correspond to a higher $T_m$, e.g., 40% formamide, with 5× or 6×SCC. High stringency hybridization conditions correspond to the highest $T_m$, e.g., 50% formamide, 5× or 6×SCC. SCC is a 0.15M NaCl, 0.015M Na-citrate. Hybridization requires that the two nucleic acids contain complementary sequences, although depending on the stringency of the hybridization, mismatches between bases are possible. The appropriate stringency for hybridizing nucleic acids depends on the length of the nucleic acids and the degree of complementation, variables well known in the art. The greater the degree of similarity or homology between two nucleotide sequences, the greater the value of $T_m$ for hybrids of nucleic acids having those sequences. The relative stability (corresponding to higher $T_m$) of nucleic acid hybridizations decreases in the following order: RNA:RNA, DNA:RNA, DNA:DNA. For hybrids of greater than 100 nucleotides in length, equations for calculating $T_m$ have been derived (see Sambrook et al., supra, 9.50-9.51). For hybridization with shorter nucleic acids, i.e., oligonucleotides, the position of mismatches becomes more important, and the length of the oligonucleotide determines its specificity (see Sambrook et al., supra, 11.7-11.8). A minimum length for a hybridizable nucleic acid is at least about 10 nucleotides; preferably at least about 15 nucleotides; and more preferably the length is at least about 20 nucleotides.

In a specific embodiment, the term "standard hybridization conditions" refers to a $T_m$ of 55° C., and utilizes conditions as set forth above. In a preferred embodiment, the $T_m$ is 60° C.; in a more preferred embodiment, the $T_m$ is 65° C. In a specific embodiment, "high stringency" refers to hybridization and/or washing conditions at 68° C. in 0.2× SSC, at 42° C. in 50% formamide, 4×SSC, or under conditions that afford levels of hybridization equivalent to those observed under either of these two conditions.

Suitable hybridization conditions for oligonucleotides (e.g., for oligonucleotide probes or primers) are typically somewhat different than for full-length nucleic acids (e.g., full-length cDNA), because of the oligonucleotides' lower melting temperature. Because the melting temperature of oligonucleotides will depend on the length of the oligonucleotide sequences involved, suitable hybridization temperatures will vary depending upon the oligoncucleotide molecules used. Exemplary temperatures may be 37° C. (for 14-base oligonucleotides), 48° C. (for 17-base oligoncucleotides), 55° C. (for 20-base oligonucleotides) and 60° C. (for 23-base oligonucleotides). Exemplary suitable hybridization conditions for oligonucleotides include washing in 6×SSC/0.05% sodium pyrophosphate, or other conditions that afford equivalent levels of hybridization.

EXAMPLES

The present invention will be better understood by reference to the following Examples, which are provided as exemplary of the invention, and not by way of limitation.

Example 1

Identification and Cloning of the Non-Ribosomal Peptide Synthetase Complex Responsible for Antibiotic Production (AC98) in S. hygroscopicus Methods Isolation of genomic DNA from S. hygroscopicus. Streptomyces hygroscopicus strain designated NS17 was cultured by inoculation of 25 ml of sterile tryptone soya broth (TSB) (Oxoid, Ogdensberg, N.Y.) prepared by combining 30 g of TSB in 1 L of distilled water) with 100 µl of a frozen glycerol stock of NS17. Cultures were grown at 28° C. while shaking at 200 rpm for 2 days. Cells were harvested by centrifugation at 3000×g for 10 min, followed by resuspension of the pelleted cells in 2 ml lysis buffer (2% Triton X-200, 1% SDS, 100 mM NaCl, 10 mM Tris, pH 8.0, 1 mm EDTA) and vortexing. After vortexing, 2 ml of phenol/chloroform/isoamyl alcohol (25/24/1 v/v) was added and the suspension was vortexed again for about 1 min to ensure lysis. The sample was then centrifuged for 5 min at 3000×g and the aqueous phase was added to 2 volumes of 95% ethanol to precipitate the genomic DNA. The precipitate was collected by centrifugation or by spooling, washed once with 70% ethanol, and air dried. DNA was resuspended in 100 µl of TE buffer (10 mM Tris, 1 mM EDTA, pH 8.0).

Isolation of a peptide synthetase probe and Southern hybridization. Degenerate PCR primers were designed based on the highly conserved core motifs of peptide synthetase adenylation domains A3 and A8 (Marahiel et al., 1997).

```
forward    5'-AC_{G/C}TC_{G/C}GGC_{T/A}CGCACCGGCCIGCC_{G/C}AAG-3'
primer     (SEQ ID NO: 19)

reverse    5'AGCTC_{G/C}A_{T/CG/C}CG_{G/C}TAGCC_{G/C}CG_{G/C}A_{T/C}CTT_{G/C}
primer     ACCTG-3' (SEQ ID NO: 20)
```

$_{G/C}$ or $_{T/A}$ or $_{T/C}$ denote either base at that position

NS17 genomic DNA was used as a template to synthesize a fragment of about 800 bp in length by PCR using a Perkin Elmer DNA Thermal Cycler 480 (Boston, Mass.-30 cycles: 95° C.-1 min, 55° C.-1 min, 72° C.-1 min). This fragment was subjected to end sequencing using an Applied Biosystems, Inc. ABI3700 sequencer (Foster City, Calif.) to determine that it corresponded to a portion of peptide synthetase adenylation domain, and used to as a probe in Southern hybridization of NS17 genomic DNA under standard conditions (Sambrook et al., 1989).

Identification of a functional NS17 peptide synthetase module. A 3 kb fragment containing a putative peptide synthetase module identified from the Southern hybridization was sequenced as described above for confirmation, and used in a biosynthetic assay to determine whether the putative peptide synthetase module was part of the AC98 biosynthetic cluster. Specifically, the method described under Example 2, below, was used to insertionally inactivate the putative peptide synthetase, which was then used to replace the endogenous peptide synthetase in *S. hygroscopicus* NS17, by homologous recombination. If the 3 kb fragment was part of the AC98 biosynthetic gene cluster, replacement of the endogenous gene with the insertionally inactivated 3 kb fragment would inhibit antibiotic production if the peptide synthetase encoded by 3 kb fragment is part of the AC98 biosynthetic cluster.

To evaluate antibiotic production, samples were removed from 50 ml cultures NS17 carrying the disrupted gene. Cultures were grown at 28° C. in PharmaMedia (Chrysalis PharmaMedia, N.J.: 10 g/L PharmaMedia, 5 g/L $CaCO_3$, 40 g/L glucose) and were analyzed by HPLC. 20 µl aliquots were loaded onto a Waters 4 mm×50 mm YMC ods-a-column (Milford, Mass.) and eluted with a gradient of 10% acetonitrile/90% TFA (20%) in water to 34% acetonitrile/66% TFA in water over 15 minutes. AC98 related compounds were detected by UV-DAD at 226 nm. Chromatograms were compared to chromatograms of samples taken from a similarly treated culture of the parental strain.

Preparation and Screening of an NS17 Cosmid Library. Genomic DNA isolated from NS17 as described above was used for the construction of a cosmid library. Optimal conditions for partial digestion of the DNA by restriction enzymes, to produce DNA fragments of about 35 kb, was determined using published techniques (Sambrook et al., 1989). The digested DNA fragments were dephosphorylated with calf intestinal alkaline phosphatase (New England Biolabs, Beverly, Mass.) according to the protocol provided by the manufacturer, and ligated into the commercial vector, pWE 15 (Stratagene, La Jolla, Calif.) according to the manufacturer's instructions. Packaging of the ligated mixture was accomplished using Gigapack III XL packaging extract (Stratagene), and the resulting library was titered and amplified according to the manufacturer's instructions.

The cosmid library was screened using the 3 kb peptide synthetase fragment, identified as described above, according to standard colony hybridization protocols (Sambrook et al., 1989). One cosmid, designated pNWA117, was selected for further study.

Cosmid analysis and identification of ORFs 1-13. Cosmid pNWA117 was digested with EcoRI, subjected to agarose gel electrophoresis and used in a Southern hybridization with the 3 kb fragment, identified as described above, as a probe. Following confirmation that the pNWA117 contained the 3 kb fragment, the cosmid was sequenced (MWG Biotech, Highpoint, N.C.).

Nucleotide BLAST analysis (SeqWeb™, which uses Wisconsin [GCG]Package version 10) was performed to identify individual ORFs and their putative function, according to their homology with known sequences. Results are presented in Table 1.

Cosmid analysis and identification of ORFs 14-23. Genomic DNA downstream of pNWA117 was isolated from a cosmid library by using a fragment of DNA from ORF12 of the analyzed sequence to select cosmids containing stretches of genomic DNA encoding that region of AC98 biosynthetic pathway. This process is commonly referred to as chromosomal walking. One such cosmid, pNWA105, was selected after restriction analysis indicated that it contained approximately 12 Kb of DNA downstream of ORF13. Nucleotide BLAST analysis of sequence data obtained was performed to identify nine complete ORFs (ORF14, ORF15, ORF16, ORF17, ORF18, ORF19, ORF20, ORF21, and ORF22) and one partial ORF (ORF23) and their putative function in AC98 biosynthesis, according to their homology with known sequences. Results are presented in Table 1.

Results

Isolation of an NRPS in NC17 responsible for the production of AC98. Results from the experiments described above demonstrate that cosmid pNWA117 contains the genes encoding a NRPS required for the synthesis of the peptide core of the novel antibiotic complex AC98, which is produced by the terrestrial actinomycete *Streptomyces hygroscopicus*. pNWA117 also contains 13 additional ORFs proposed to be involved in the synthesis of the AC98 complex. PNWA105 contains at least 4 additional ORFs that are proposed to be involved in AC98 biosynthesis. The NRPS complex exists as two separate components, mppA and mppB. mppA is encoded within bp 10069 and 18309 of the sequence listed in SEQ ID. NO: 1, and is comprised of about 2747 amino acids (SEQ ID NO: 2). mppB is encoded within bp 18309 and 29312 of the sequence listed in SEQ ID NO: 1, and is comprised of about 3668 amino acids (SEQ ID NO: 3). Additional description and characterization of mppA and mppB is described infra, under the heading DETAILED DESCRIPTION.

Table 1 lists the 23 ORFs and corresponding SEQ ID NO's that were identified and determined to be tailoring enzymes involved in the production of the protein core of AC98 (column 1). Column 2 lists the bp position of each ORF according to the sequence contained within cosmid pNWA117 (SEQ ID NO: 1), along with the number of the amino acids encoded by each ORF (column 3). Column 4 identifies the public sequence with which each ORF is most homologous, according to BLAST analysis, and column 5 lists the proposed function of each polypeptide encoded by the individual ORFs based on the sequence homology.

Example 2

Preparation of an Intergeneric Vector

Materials

DNA restriction and modification enzymes and T4 DNA ligase were obtained from New England Biolabs. Plasmid DNA was isolated using commercial kits (Qiagen) and DNA fragments were purified using commercial kits (Tetra Link International). Competent *E. coli* cells were obtained from Stratagene. All were used according to manufacturer's specifications and with buffers and reagents supplied by the manufacturer. *Streptomyces* chromosomal DNA was prepared according to published protocols (Keisser et al. Practical *Streptomyces* Genetics, John Innes Centre, Norwich, England, 2000). Antibiotics were purchased from Sigma.

Methods pNWA200 vector preparation. A purified PstI fragment containing oriT from the R plasmid, RP4, was ligated to pFD666 (Denis & Brzezinski, *Gene*, 111:115, 1992), which was then linearized by digestion with PstI and dephosphorylated with calf intestinal phosphatase. This ligation mixture was transformed into competent XL-10 *E. coli* cells (Stratagene) following manufacturer's directions. The transformed cells were then plated onto nutrient agar plates containing 50 µg/ml kanamycin and incubated at 37° C. for 1 day. The incubation resulted in about 150 colonies. The colonies were replica plated onto a second kanamycin containing agar plate covered by a positively charged nylon filter, and after 6 hours incubation, the nylon filter containing the embedded colonies was treated with 0.5M NaOH (in 1M NaCl) to lyse the bacteria and denature their DNA according to standard Southern blotting procedures (Southern et al., *J Mol Biol.*, 98:503, 1975). The nylon filter was probed with a radioactively labeled 0.76 kb PstI fragment and one colony was selected on the basis of its hybridizing signal. The recombinant plasmid was then extracted from a fresh culture of the original hybridizing colony. Digestion of the plasmid with PstI produced two DNA fragments which electrophoresed to positions of 5.25 kb and 0.76 kb, corresponding to linear pFD666 (5.25 kb) and the 0.76 kb oriT containing Pst1 fragment. This recombinant vector replicated stably in *E coli* strains and did not show genetic rearrangement upon repeated subculturing and further isolation.

Example 3

Methods for the Modification of the NRPS AC98 Peptide Core

Based on the sequence data of mppA and mppB describe above, and available data defining the critical binding pocket features, i.e., amino acid residues in the adenylation domain that determine the specificity of the amino acid that is accepted by the domain, those skilled in the art will be able to modify any of the adenylation domains of the NRPS and change the primary amino acid sequence in the peptide core of AC98, thus, modifying the properties of the molecule. This Example provides two methods for modifying the peptide core.

Preparation of an engineered bacterial strain that produces AC98. Preparation of an AC98-producing host strain for use for the production of modified AC98 described by the methods below, is done according to the following steps:

1. Clone a fragment of the adenylation domain from and NRPS of choice (e.g., using *E. coli*).
2. Insert an antibiotic resistance determinant, such as apramycin, within the cloned fragment from step 1, above. This insertion inactivates adenylation domain after it is inserted into a host genome.
3. Clone the construct in an intergeneric conjugation vector, such as pNWA200, which contains a second antibiotic resistance determinant, such as kanamycin.
4. Introduce the vector containing the cloned construct into an AC98-producing strain.
5. Select for a strain that has the construct integrated into the homologous region of the host's genomic DNA by screening for conjugates that are apramycin-resistant and kanamycin-sensitive.

6. Confirm integration of the apramycin resistance determinant at the desired location by southern hybridization and fermentation.

Once the proper host strain is selected, the insertionally inactivated module in the host genome can be replaced by either the same module that has been modified by site-directed mutagenesis, or by a module that has an adenylation domain that specifies acceptance of a different amino acid.

Method 1

Modification of the adenylation domain for the production of modified AC98. The cloned module of choice, e.g., the adenylation domain, is modified by introducing nucleotide changes that will alter the codons that specify the incorporation of the amino acids critical to the biding pocket. The nucleotide changes can be introduced using any method known in the art, such as site-directed mutagenesis. For example, changing the triplet codon for Ser239 in the tyrosine binding pocket of mppB from TCC to TGG, and changing the triplet codon for Valine299 from GTC to ATC, would change the amino acids at those sites to tryptophan and isoleucine, respectively. According to published data, one would expect that these changes would alter the specificity of the module from tyrosine to phenylalanine (Stachelhaus et al., Chemistry and Biol. 1999; 6:493-505).

The mutated module is then introduced, by conjugation, into a host strain that has been modified, as outlined above, to be resistant to an antibiotic, such as apramycin. Selection for the presence of a recombinant strain is two-fold. First, exconjugates are selected that are able to grown in the presence of kanamycin and apramycin. These strains represent those that have taken up the vector construct. Second, clones are selected that have lost resistance to both kanamycin and apramycin. This indicates that the susceptible clones have lost the apramycin resistance due to homologous recombination between the insertionally inactivated host tyrosine domain and the site-directed mutant version of the tyrosine domain. This loss of resistance further indicates that the vector is no longer in the host strain, and the mutated version of the tyrosine domain (i.e., the one specific for phenylalanine) replaced the insertionally inactivated tyrosine domain of the host (engineered as described above). Southern hybridization is then performed to confirm the insertion of the correct construct. Fermentation of the strain will result in the production of modified AC98 products where the cyclic peptide core contains phenylalanine in place of tyrosine.

Method 2

Module replacement or swapping for the production of modified AC98. For this method, two regions of approximately 1 kb flanking the module selected for replacement are cloned by PCR (the □arms□). The two arms are engineered so that the ends closest to the module (i.e., the 3' end on one arm and the 5' arm on the other) have appropriate restriction sites for subsequent insertion of the module in the correct orientation between the flanking arms. Next, the module of choice for insertion from another peptide synthetase (e.g., the threonine module from the CDA NRPS of S. coelicolor) is amplified by PCR. This PCR product is also engineered to contain the appropriate restriction sites compatible with those present in the cloned arms, in order for insertion between the two arms. After ligation of the arms and the module, the construct is transferred to the intergeneric conjugation vector, and introduced into a antibiotic-resistant host strain (e.g., the apramycin-resistant strain as described above). Selection of the conjugates is then performed as described above for the mutated module method. Those strains expressing the threonine module from the CDA NRPS instead of the tyrosine module of the AC98 NRPS are identified as being the result of homologous recombination between the arms of the vector and the homologous regions on the host NRPS that flank the insertionally inactivated tyrosine module. Production of the modified AC98, where the cyclic peptide core contains threonine, is achieved by fermentation.

Appropriate steps should be taken to ensure maintenance of the integrity of the ORFs during the processes described above. For example, sequencing of all PCR products is preferred to confirm that no inadvertent mutations are introduced into the sequences that will be used for cloning.

In addition or as an alternative to the peptide synthetase module of the NRPS, tailoring enzymes, such as those indicated in Table 1, may also be modified according to these methods in order to produce antibiotic molecules having a modified peptide core. As one example, inactivation of a methyltransferase enzyme will result in an antibiotic lacking specific methyl groups, which then may be evaluated for improved antibiotic activity.

The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims.

It is further to be understood that values are approximate, and are provided for description.

Patents, patent applications, publications, procedures, and the like are cited throughout this application, the disclosures of which are incorporated herein by reference in their entireties.

What is claimed:

1. An isolated nucleic acid having a nucleotide sequence selected from the group consisting of:
   (a) a nucleotide sequence as set forth in SEQ ID NO: 1; and,
   (c) an isolated nucleic acid fragment having a nucleotide sequence complementary to the nucleotide sequence of (a).

2. An isolated nucleic acid according to claim 1, wherein the nucleic acid has a nucleotide sequence that is complementary to the sequence set forth in SEQ ID NO: 1.

3. A chimeric nucleic acid construct comprising a nucleic acid of claim 1 or 2, wherein said nucleic acid is operatively associated with an expression control sequence.

4. An expression vector comprising the nucleic acid of claim 1 or 2, wherein the nucleic acid is operatively associated with an expression control sequence.

5. An isolated host cell genetically modified to express the nucleic acid of claim 1 or 2.

6. An isolated host cell genetically modified to express the nucleic acid of claim 1.

7. An isolated host cell comprising the expression vector of claim 4.

8. The isolated nucleic acid of claim 1, wherein the nucleic acid sequence encodes a non-ribosomal peptide synthetase (NRPS), and wherein the NRPS produces antibiotic AC98.

Figure 1:
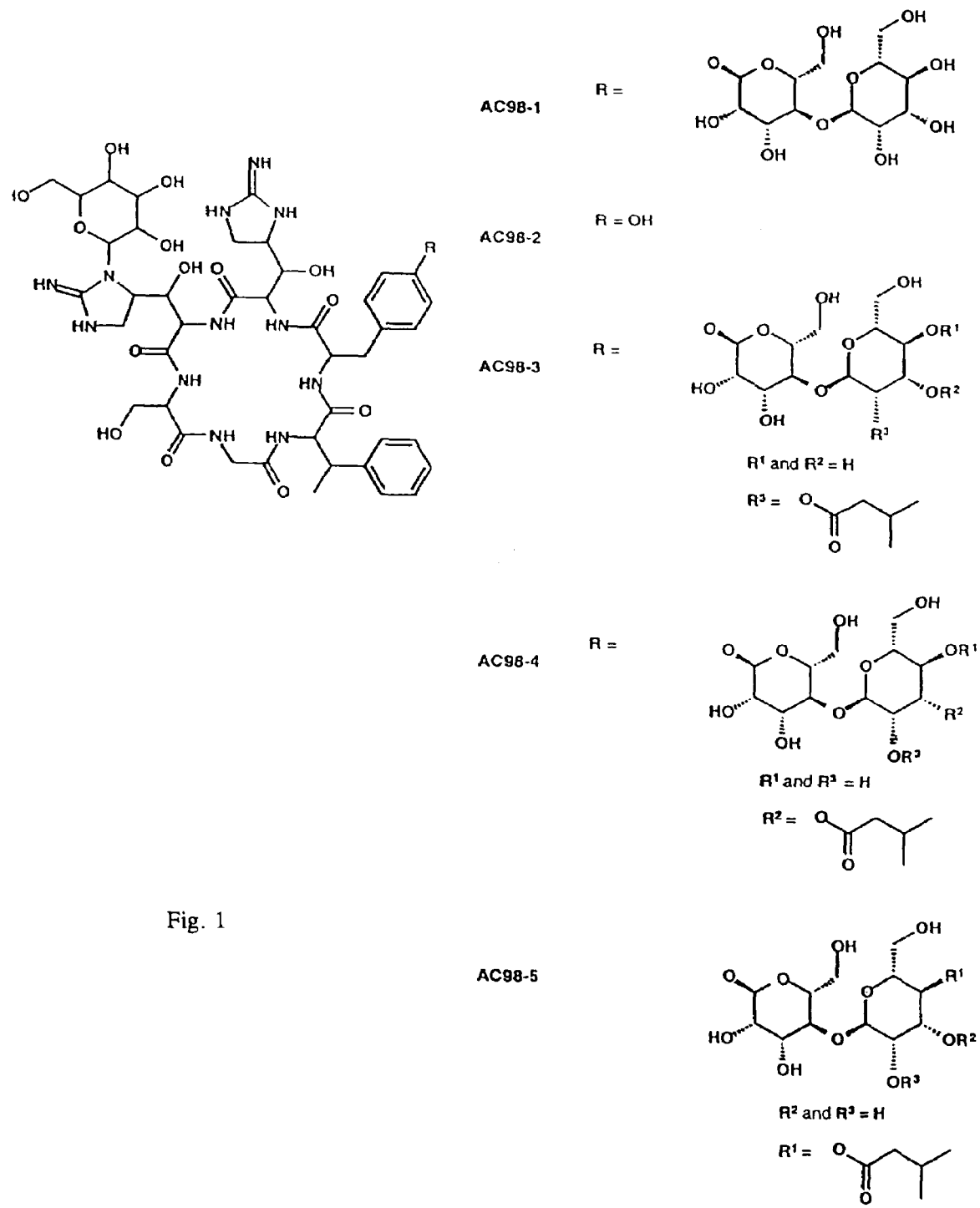
FIG. 1 depicts the chemical structures of the lipoglycopeptide antibiotic AC98.
Figure 2:
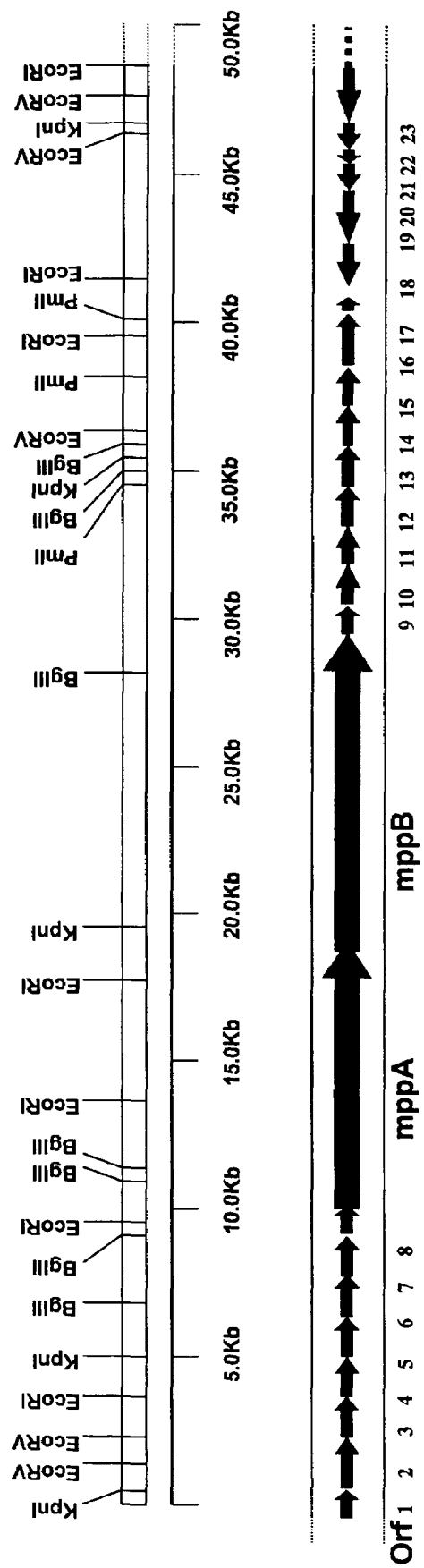
FIG. 2 shows a representation of the NRPS complex from this *Streptomyces hygroscopicus* strain NS17 that is demonstrated to be the minimal biosynthetic machinery responsible for the biosynthesis of the peptide core of AC98.

9. The isolated nucleic acid of claim 8, wherein said antibiotic has the structure as depicted in FIG. 1.

10. An isolated host cell genetically modified to express the nucleic acid having a nucleotide sequence as depicted in SEQ ID NO. 1.

11. An isolated nucleic acid which encodes a non-ribosomal peptide synthetase (NRPS), wherein the NRPS produces antibiotic AC98, wherein the nucleic acid sequence has a nucleotide sequence set forth in SEQ ID NO: 1.

12. The isolated nucleic acid of claim 11, wherein said antibiotic is a lipoglycopeptide antibiotic with activity against Gram-positive pathogens.

13. The isolated nucleic acid of claim 11, wherein said antibiotic has the structure as depicted in FIG. 1.

* * * * *